US011147789B2

(12) United States Patent
Elmer et al.

(10) Patent No.: US 11,147,789 B2
(45) Date of Patent: *Oct. 19, 2021

(54) CELL-PERMEABLE SUCCINATE COMPOUNDS

(71) Applicant: NEUROVIVE PHARMACEUTICAL AB, Lund (SE)

(72) Inventors: Eskil Elmer, Lund (SE); Magnus Joakim Hansson, Landskrona (SE); Karl Henrik Johannes Ehinger, Lund (SE); Steven Moss, Balsham (GB)

(73) Assignee: ABLIVA AB, Lund (SE)

( * ) Notice: Subject to any disclaimer, the term of this patent is extended or adjusted under 35 U.S.C. 154(b) by 183 days.

This patent is subject to a terminal disclaimer.

(21) Appl. No.: 15/128,480

(22) PCT Filed: Apr. 8, 2015

(86) PCT No.: PCT/EP2015/057606
§ 371 (c)(1),
(2) Date: Sep. 23, 2016

(87) PCT Pub. No.: WO2015/155231
PCT Pub. Date: Oct. 15, 2015

(65) Prior Publication Data
US 2017/0105961 A1    Apr. 20, 2017

(30) Foreign Application Priority Data

Apr. 8, 2014  (DK) .................. PA 2014 70190

(51) Int. Cl.
| A61K 31/265 | (2006.01) |
| C07C 327/28 | (2006.01) |
| C07C 327/34 | (2006.01) |
| C07C 327/32 | (2006.01) |
| A61K 45/06 | (2006.01) |
| C07C 327/30 | (2006.01) |
| A61K 31/155 | (2006.01) |
| A61K 31/22 | (2006.01) |
| C07D 211/76 | (2006.01) |
| A61P 11/00 | (2006.01) |
| A61P 9/00 | (2006.01) |
| A61P 21/00 | (2006.01) |

(52) U.S. Cl.
CPC .......... *A61K 31/265* (2013.01); *A61K 31/155* (2013.01); *A61K 31/22* (2013.01); *A61K 45/06* (2013.01); *A61P 9/00* (2018.01); *A61P 11/00* (2018.01); *A61P 21/00* (2018.01); *C07C 327/28* (2013.01); *C07C 327/30* (2013.01); *C07C 327/32* (2013.01); *C07C 327/34* (2013.01); *C07D 211/76* (2013.01); *C07C 2601/14* (2017.05); *Y02A 50/30* (2018.01)

(58) Field of Classification Search
None
See application file for complete search history.

(56) References Cited

U.S. PATENT DOCUMENTS 9,670,175 B2 *  6/2017  Fliri ................. C07C 69/40

FOREIGN PATENT DOCUMENTS

| CA | 1058168 | 7/1979 |
| EP | D583480 | 2/1994 |
| GB | 756422 | * 9/1956 |
| GB | 1506934 A | 4/1978 |
| JP | 07-331262 A | 12/1995 |
| JP | 2014024772 | 2/2014 |
| KR | 100791844 | 1/2008 |
| WO | 97/47584 | 12/1997 |
| WO | 1997/047584 A1 | 12/1997 |
| WO | 00/01838 A2 | 1/2000 |
| WO | 02/28345 | 4/2002 |
| WO | 2008/054059 | 5/2008 |
| WO | 2008/118948 | 10/2008 |
| WO | 2012/011063 | 1/2012 |
| WO | 2014/053857 | 4/2014 |
| WO | 2015/155230 | 10/2015 |
| WO | 2015/155238 | 10/2015 |

OTHER PUBLICATIONS

Chemical Abstract Registry No. 477766-64-6, indexed in the Registry File on STN CAS Online Dec. 30, 2002.*
Ito et al., A medium-term rat liver bioassay for rapid in vivo detection of carcinogenic potential of chemicals. Cancer Science, 2003, 94, 3-8.*
Chemical Abstract Registry No. 501358-19-6, indexed in the Registry File on STN CAS Online Apr. 2, 2003.*
An updated "Chemical Abstract Registry No. 477766-64-6, indexed in the Registry File on STN CAS Online Dec. 30, 2002."*
Globa, O.V., et al., "Succinate Treatment in Children with Lactic Acidosis," European Collaboration: Towards Drug Development and Rational Drug Therapy, Proceedings of the Sixth Congress of the European Association for Clinical Pharmacology and Therapeutics, Istanbul, Jun. 24-28, 2003, Eds. Tulunay and Orme, Springer-Verlag Berlin Heidelberg GmbH, 2003, p. 130.

(Continued)

*Primary Examiner* — Po-Chih Chen
(74) *Attorney, Agent, or Firm* — Robert C. Netter, Jr.; Dann, Dorfman, Herrell & Skillman

(57) ABSTRACT

The present invention provides novel cell-permeable succinates and cell permeable precursors of succinateaimed at increasing ATP-production in mitochondria. The main part of ATP produced and utilized in the eukaryotic cell originates from mitochondrial oxidative phosphorylation, a process to which high-energy electrons are provided by the Kreb's cycle. Not all Kreb's cycle intermediates are readily permeable to the cellular membrane, one of them being succinate. The provision of the novel cell permeable succinates is envisaged to allow passage over the cellular membrane and thus the cell permeable succinates can be used to enhance mitochondrial ATP-output.

21 Claims, 10 Drawing Sheets

(56) References Cited

OTHER PUBLICATIONS

Figure 1:
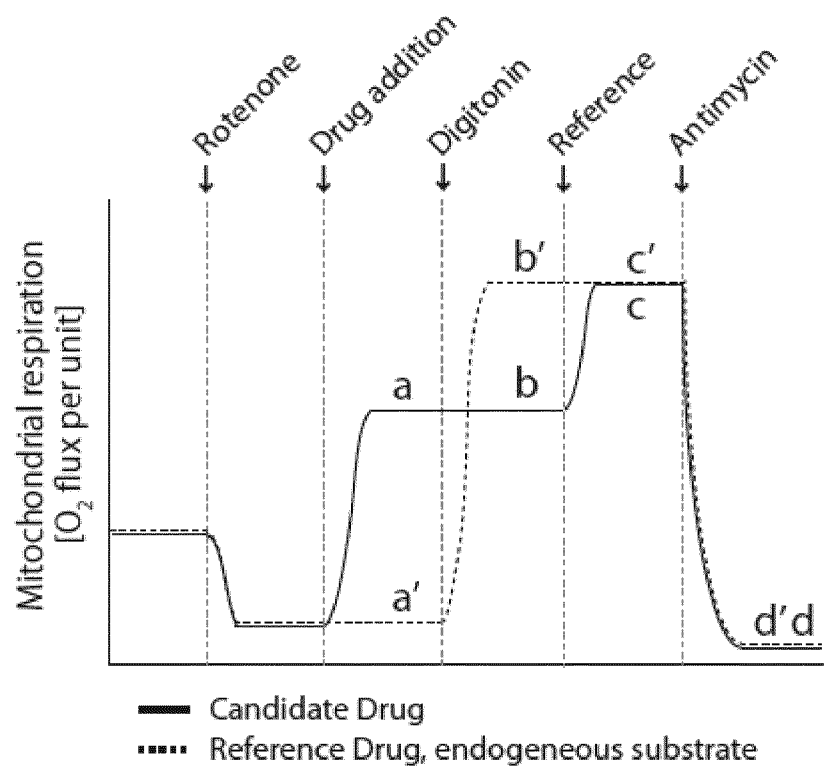

Klug, E., et al., "AGI-1067 Improves Glycemic Control when Added to Current Regimens in Patients with Type 2 Diabetes" Diabetes (2008) 57(S1):A132 [Abstract].

Kruidering, M., et al., "Cispltain-Induced Nephrotoxicity in Porcine Proximal Tubular Cells: Mitochondruial Dysfunction by Inhibition of Complexes I to IV of the Respiratory Chain," J. Pharmacol. Exper. Therap. (1997) 280:638-649.

Moore, S.A., et al., "Model Reactions for CoA Transferase Involving Thiol Transfer. Anhydride Formation from Thiol Esters and Carboxylic Acids," J. Biol Chem. (1982) 257:10882-10892.

Nudelman, A., et al.,"The Role of Intracellularly Released Formaldehyde and Butyric Acid in the Anticancer Activity at Acyloxyalkyl Esters," J. Med. Chem. (2005) 48:1042-1054.

Eggerer, H., et al., "On the Role of Acetyl Cyanide in the Cyanide-Induced Acetylation of Amino Acids by Enzymes of Clostridium Kluyveri" Arch. Biochem. Biophys. (1962) 98:432-443.

Loontjens, T., et al., "Synthesis of 1,2-bis(2-oxazolinyl-2)ethane and its application as chain extender for poly ethylene terephthalate)" Polymer Bulletin (1993) 30:13-18.

Xu, J., et al., "Amidoamine dendron-based co-adsorbents: improved performance in dye-sensitized solar cells" J. Mater. Chem. A (2013) 1:14524-14531.

Pohl, N.L., et al., "Synthesis and Incorporation of an N-Acetylcysteamine Analogue of Methylmalonyl-CoA by a Modular Polyketide Synthase" J. Am. Chem. Soc. (1998) 120(43):11206-11207.

Registry No. 57753-01-2, Chemical Abstract Registry on STN (1984) Columbus, Ohio.

Murli, S., et al., "Chemobiosynthesis of novel 6-deoxyerythronolide B analogues by mutation of the loading module of 6-deoxyerythronolide B synthase 1" Appl. Environ. Microbiol. (2005) 71(8):4503-9.

Hughes, A., et al., "Employing a polyketide synthase module and thioesterase in the semipreparative biocatalysis of diverse triketide pyrones" Med Chem. Commun. (2012) 3:956-959.

Zhang, J., et al., "Synthesis of O-acyl-L-serine and S-acyl-L-cysteine derivatives" Zhongguo Yaowu Huaxue Zazhi (2003) 13(2):93-96 [Abstract].

Registry No. 862466-70-4, Chemical Abstract Registry (2005) Columbus, Ohio.

\* cited by examiner

CELL-PERMEABLE SUCCINATE COMPOUNDS

This application is a § 371 application of PCT/EP2015/057606, filed Apr. 8, 2015, which in turn claims priority to DK Application PA 2014 70190, filed Apr. 8, 2014.

FIELD OF THE INVENTION

The present invention provides novel cell-permeable succinates and cell permeable precursors of succinate aimed at increasing ATP-production in mitochondria. The main part of ATP produced and utilized in the eukaryotic cell originates from mitochondrial oxidative phosphorylation, a process to which high-energy electrons are provided by the Kreb's cycle. Not all Kreb's cycle intermediates are readily permeable to the cellular membrane, one of them being succinate. The provision of the novel cell permeable succinates is envisaged to allow passage over the cellular membrane and thus the cell permeable succinates can be used to enhance mitochondrial ATP-output.

Moreover, present invention also provides for cell permeable succinates or equivalents to succinates which in addition to being cell permeable and releasing succinate in the cytosol are also potentially able to provide additional energy to the organism by the hydrolytic products resulting from either chemical or enzymatic hydrolysis of the succinate derivatives.

The present invention also provides methods for preparing compounds of the invention that have improved properties for use in medicine and/or in cosmetics. Notably, the compounds of the invention are useful in the prevention or treatment of mitochondria-related disorders, in maintaining normal mitochondrial function, enhancing mitochondrial function, i.e. producing more ATP than normally, or in restoring defects in the mitochondrial respiratory system.

BACKGROUND OF THE INVENTION

Mitochondria are organelles in eukaryotic cells. They generate most of the cell's supply of adenosine triphosphate (ATP), which is used as an energy source. Thus, mitochondria are indispensable for energy production, for the survival of eukaryotic cells and for correct cellular function. In addition to supplying energy, mitochondria are involved in a number of other processes such as cell signalling, cellular differentiation, cell death as well as the control of the cell cycle and cell growth. In particular, mitochondria are crucial regulators of cell apoptosis and they also play a major role in multiple forms of nonapoptotic cell death such as necrosis.

In recent years many papers have been published describing mitochondrial contributions to a variety of diseases. Some diseases may be caused by mutations or deletions in the mitochondrial or nuclear genome, while others may be caused by primary or secondary impairment of the mitochondrial respiratory system or other mechanisms related to mitochondrial dysfunction. At present there is no available treatment that can cure mitochondrial diseases.

In view of the recognized importance of maintaining or restoring a normal mitochondrial function or of enhancing the cell's energy production (ATP), there is a need to develop compounds which have the following properties: Cell permeability of the parent, the ability to liberate intracellular succinate or a precursor of succinate, low toxicity of the parent compound and released products, and physico-chemical properties consistent with administration to a patient.

Succinate compounds have been prepared as prodrugs of other active agents, for example WO 2002/28345 describes succinic acid bis (2,2-dimethylpropionyloxymethyl) ester, succinic acid dibutyryloxymethyl ester and succinic acid bis-(1-butyryloxyethyl)ester. These compounds are prepared as agents to deliver formaldehyde, and are aimed at different medical uses to the current compounds.

Prior art compounds include WO9747584, which describes a range of polyol succinates.

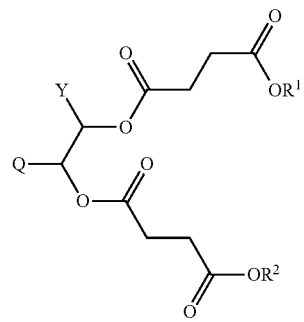

In the example given therein, Y is an H or alkyl group. Each succinate compound contains multiple succinate moieties linked by a group of structure C(Y)—C(Q), and each ester acid is therefore directly linked to a moiety containing at least two carbon atoms in the form of an ethyl group O—C—C. Each compound disclosed contains more than one succinate moiety, and the succinate moiety is not protected by a moiety of type O—C—X where X is a heteroatom.

Various succinate ester compounds are known in the art. Diethyl succinate, monomethyl succinate and dimethyl succinate are shown to be inactive in the assays exemplified below, and fall outside the scope of the invention.

Moreover, U.S. Pat. No. 5,871,755 relates to dehydroalanine derivatives of succinamides for use as agents against oxidative stress and for cosmetic purposes.

DESCRIPTION OF THE INVENTION

A compound according to the invention is given by Formula (I)

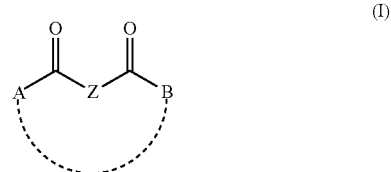

or a pharmaceutically acceptable salt thereof, wherein the dotted bond between A and B denotes an optional bond so as to form a ring closed structure, and wherein Z is selected from —CH$_2$—CH$_2$— or >CH(CH$_3$),
A is selected from —SR, —OR and NHR, and R is

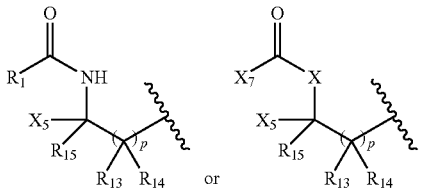

B is selected from —O—R', —NHR", —SR''' or —OH; and R' is selected from the formula (II) to (IX) below:

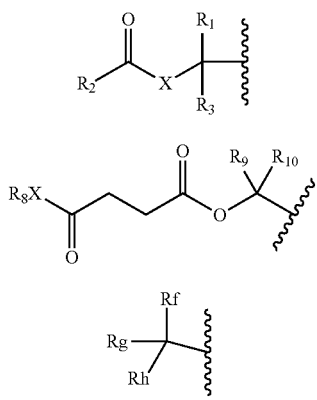

(II)

(V)

(IX)

R', R" and R''' are independently different or identical and is selected from formula (IV-VIII) below:

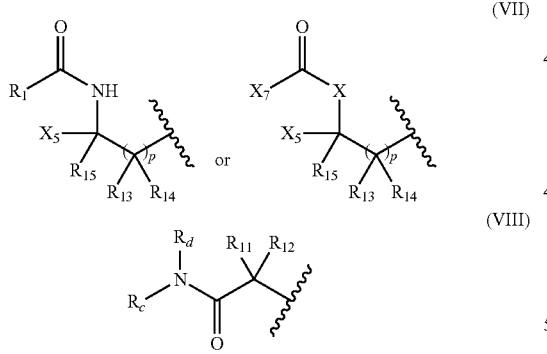

(VII)

(VIII)

R$_1$ and R$_3$ are independently different or identical and are selected from H, Me, Et, propyl, i-propyl, butyl, iso-butyl, t-butyl, O-acyl, O-alkyl, N-acyl, N-alkyl, Xacyl, CH$_2$Xalkyl, CH$_2$X-acyl, F, CH$_2$COOH, CH$_2$CO$_2$alkyl,
X is selected from O, NH, NR$_6$, S,
R$_2$ is selected from Me, Et, propyl, i-propyl, butyl, iso-butyl, t-butyl, C(O)CH$_3$, C(O)CH$_2$C(O)CH$_3$, C(O)CH$_2$CH(OH)CH$_3$,
p is an integer and is 1 or 2
R$_6$ is selected from H, Me, Et, propyl, i-propyl, butyl, iso-butyl, t-butyl, acetyl, acyl, propionyl, benzoyl, or formula (II), or formula (VIII)
X$_5$ is selected from —H, Me, Et, propyl, i-propyl, butyl, iso-butyl, t-butyl, —COOH, —C(═O)XR$_6$, CONR$_1$R$_3$ or is formula

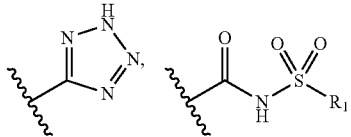

X$_7$ is selected from R$_1$, —NR$_1$R$_3$,
R$_9$ is selected from H, Me, Et or O$_2$CCH$_2$CH$_2$COXR$_8$
R$_{10}$ is selected from Oacyl, NHalkyl, NHacyl, or O$_2$CCH$_2$CH$_2$COX$_6$R$_8$
X$_6$ is selected from O, NR$_8$, NR$_6$R$_8$, wherein R$_6$ and R$_8$ are independently different or identical and are is selected from H, alkyl, Me, Et, propyl, i-propyl, butyl, iso-butyl, t-butyl, acetyl, acyl, propionyl, benzoyl, or formula (II), or formula (VIII),
R$_{11}$ and R$_{12}$ are independently different or identical and are selected from H, Me, Et, propyl, i-propyl, butyl, iso-butyl, t-butyl, acetyl, propionyl, benzoyl, —CH$_2$Xalkyl, —CH$_2$Xacyl, where X is O, NR$_6$ or S,
R$_c$ and R$_d$ are independently different or identical and are selected from CH$_2$Xalkyl, CH$_2$Xacyl, where X═O, NR$_6$ or S,
R$_{13}$, R$_{14}$ and R$_{15}$ are independently different or identical and are selected from H, Me, Et, propyl, i-propyl, butyl, iso-butyl, t-butyl, —COOH, O-acyl, O-alkyl, N-acyl, N-alkyl, Xacyl, CH$_2$Xalkyl;
Substituents on R13 and R14 or R13 and R15 may bridge to form a cyclic system to form cycloalkyl, heterocycloalkyl, lactone or lactams.
R$_f$, R$_g$ and R$_h$ are independently different or identical and are selected from Xacyl, —CH$_2$Xalkyl, —CH$_2$X-acyl and R$_9$,
alkyl is selected from Me, Et, propyl, i-propyl, butyl, iso-butyl, t-butyl,
acyl is selected from formyl, acetyl, propionyl, isopropionyl, buturyl, tert-butyryl, pentanoyl, benzoyl, succinyl.
acyl and/or alkyl may be optionally substituted, and
when the dotted bond between A and B is present, the compound according to formula (I) is

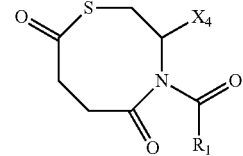

wherein X$_4$ is selected from —COOH, —C(═O)XR$_6$,

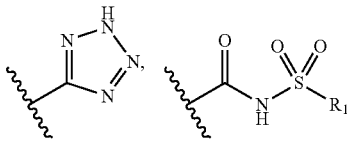

The compounds of formula (I) (and any pharmaceutically acceptable salts thereof) is referred to hereinafter as "compound of the invention", "compounds of the invention" or as "compounds of the invention".
Compounds of the invention of particular interest are those compounds wherein Z is —CH$_2$CH$_2$— and A is —SR.

Compounds of the invention of particular interest are those compounds, wherein Z is —CH₂CH₂—, A is SR, and B is OH or B is SR'''.

Compounds of the invention of particular interest are those compounds, wherein Z is —CH₂CH₂—, A is SR, B is OH or B is SR''', where R''' is

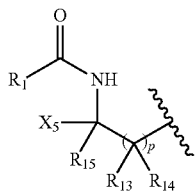

Compounds of the invention of particular interest are those compounds, wherein Z is —CH₂CH₂— and A is SR and B is OH.

Compounds of the invention of particular interest are those compounds, wherein Z is —CH₂CH₂—, A is SR, B is OH or B is SR, where R is

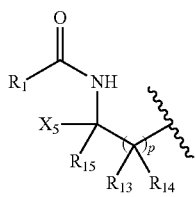

Compounds of the invention of particular interest are those compounds, wherein Z is —CH₂CH₂—, A is NR, B is OH and R is

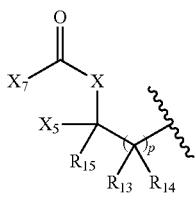

and X is S.

Preferably, and with respect to formula (II), at least one of $R_1$ and $R_3$ is —H, such that formula II is:

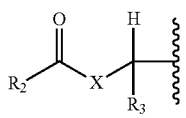

(II)

Preferably, and with respect to formula (VII), p=1 and $X_5$ is —H such that formula (VII) is

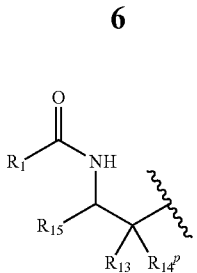

(VII)

Preferably, and with respect to formula (VII), p=1 and $X_5$ is $COXR_6$ such that formula (VII) is

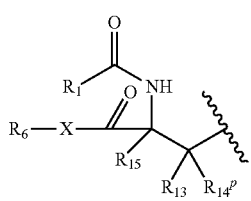

(VII)

Preferably, and with respect to formula (VII), p=1 and $X_5$ is $CONR_1R_3$ such that formula (VII) is

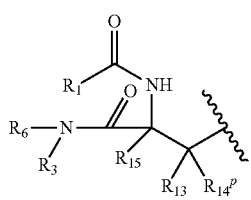

(VII)

A compound according to formula (I) may be

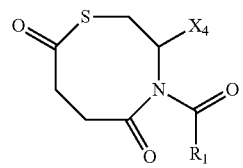

wherein $X_4$ is selected from —COOH, —C(=O)XR₆,

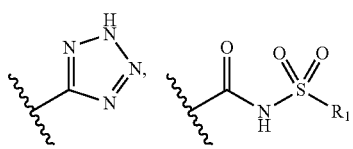

Notably, a compound according to the invention is given by Formula (IA)

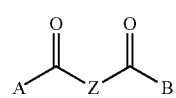

(IA)

or a pharmaceutically acceptable salt thereof, wherein
Z is —CH$_2$—CH$_2$—,
A is selected from —SR, —OR and NHR, and R is

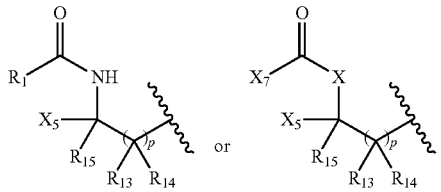

B is selected from —O—R', —NHR", —SR'" or —OH; and
R', R" and R'" are independently different or identical and is selected from one or the formulas below:

(VII)

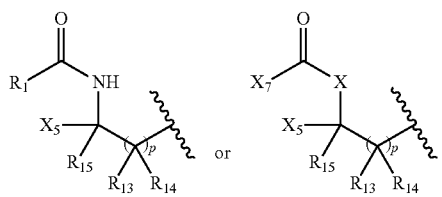

R$_1$ and R$_3$ are independently different or identical and selected from H, Me, Et, propyl, O-Me, O-Et, O-propyl,
X is selected from O, NH, S,
p is an integer and is 1,
R$_6$ is selected from H, Me, Et,
X$_5$ is selected from —H, Me, Et, —COOH, —C(=O)XR$_6$, CONR$_1$R$_3$
X$_7$ is selected from R$_1$, —NR$_1$R$_3$,
R$_{13}$, R$_{14}$ and R$_{15}$ are independently different or identical and are selected from H, Me, Et, propyl, i-propyl, butyl, iso-butyl, t-butyl, —COOH, O-acyl, O-alkyl, N-acyl, N-alkyl, Xacyl, CH$_2$Xalkyl, wherein alkyl and acyl are as defined herein before.

A compound of particular interest is given by Formula (IA)

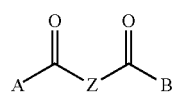

(IA)

or a pharmaceutically acceptable salt thereof, wherein
Z is —CH$_2$—CH$_2$—,
A is selected from —SR, —OR and NHR, and R is

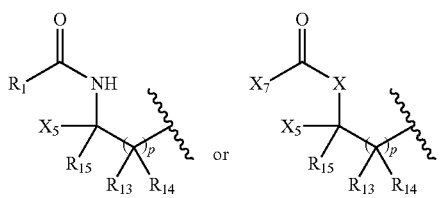

B is selected from —O—R', —NHR", —SR'" or —OH; and

R', R" and R'" are independently different or identical and is selected from one or the formulas below:

(VII)

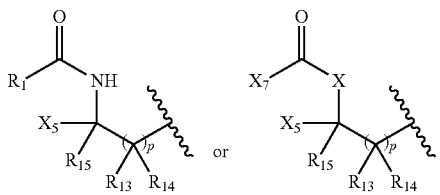

R$_1$ and R$_3$ are independently different or identical and are selected from H, Me, Et, propyl, O-Me, O-Et, O-propyl,
X is selected from O, NH, S,
p is an integer and is 1,
R$_6$ is selected from H, Me, Et,
X$_5$ is selected from —H, Me, Et, —COOH, —C(=O)OR$_6$, CONR$_1$R$_3$,
X$_7$ is selected from R$_1$, —NR$_1$R$_3$,
R$_{13}$, R$_{14}$ and R$_{15}$ are independently different or identical and are selected from H, Me, Et, —COOH.

The following compound is known from Moore et al. J. Biol. Chem., 1982, 257, pp. 10882-10892

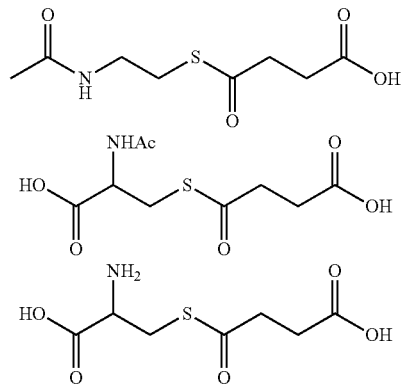

However, the invention may or may not include these compounds for use in treatment of mitochondrial related diseases as discussed herein or for the manufacture of a medicament for/in the treatment of mitochondrial related diseases as discussed herein.

Specific compounds according to the invention are:

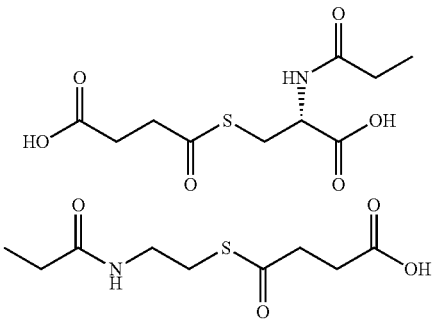

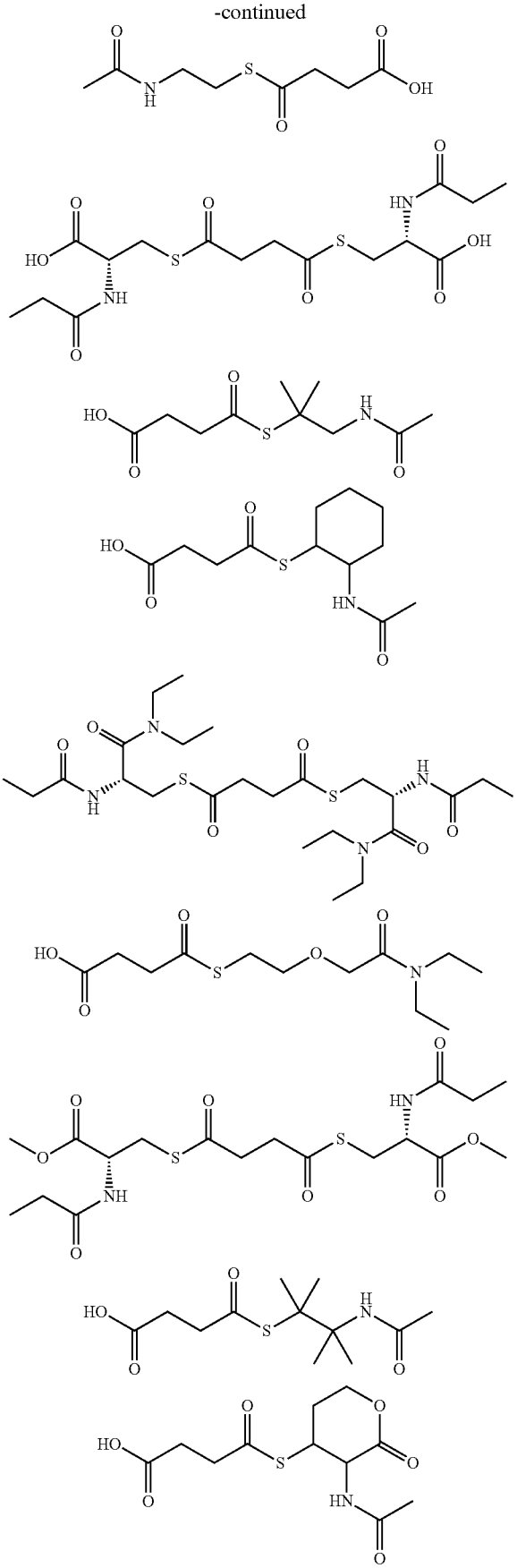
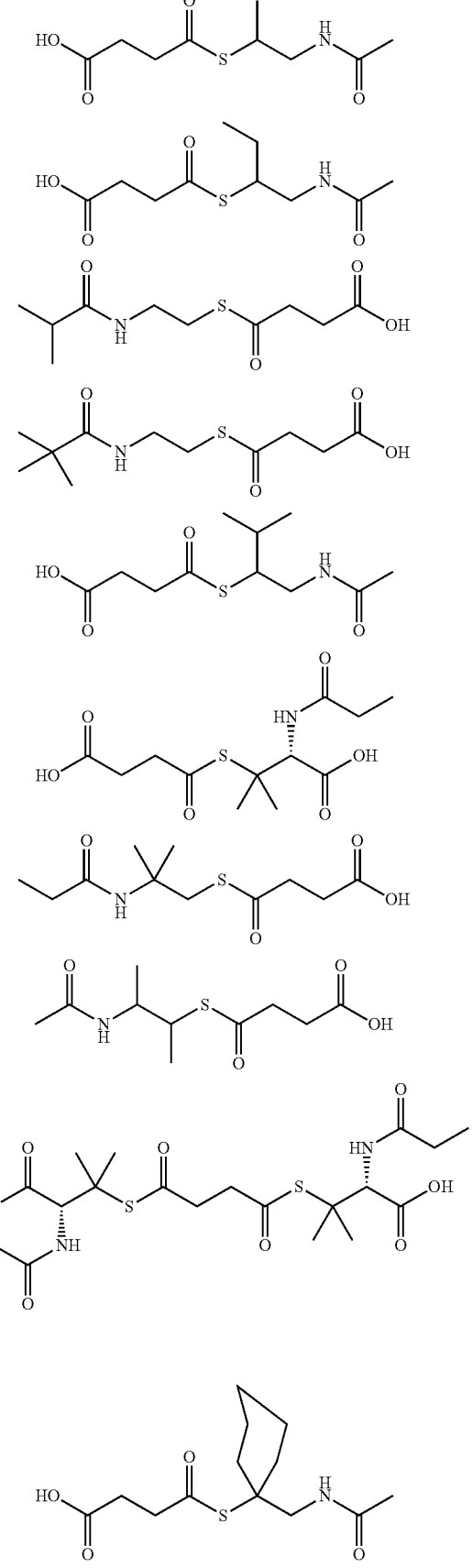

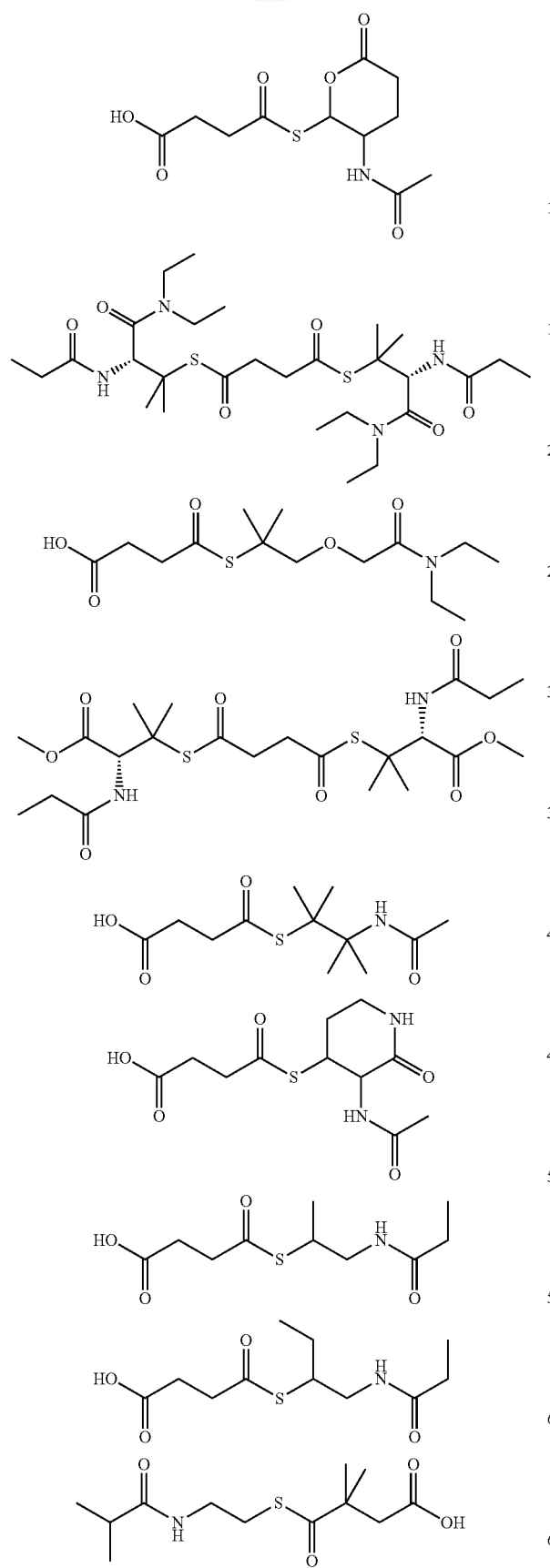
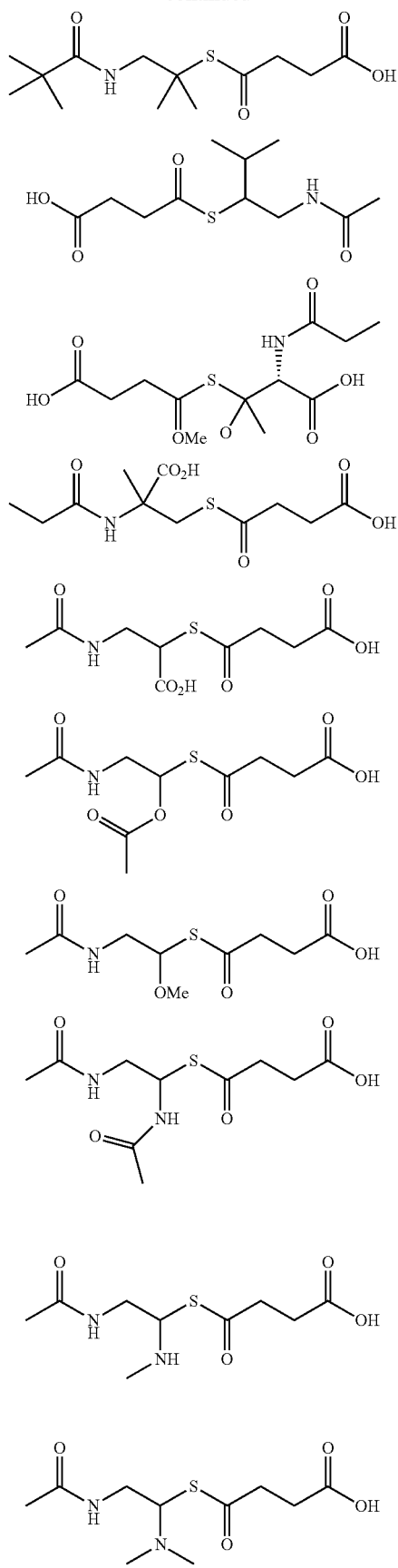

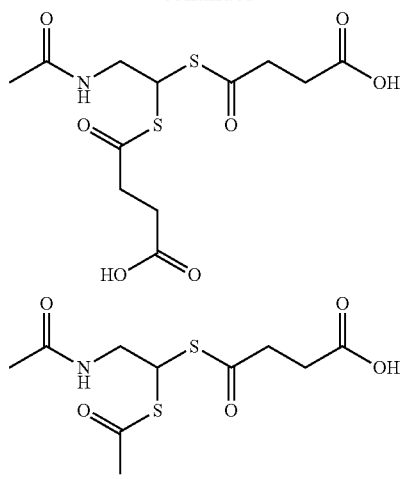

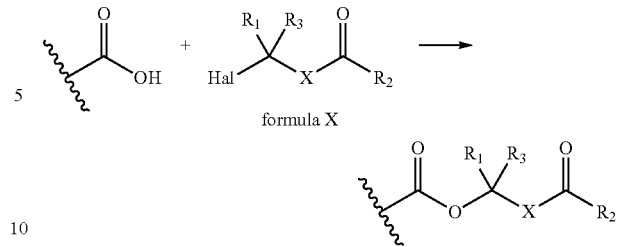

General Chemistry Methods

The skilled person will recognise that the compounds of the invention may be prepared, in known manner, in a variety of ways. The routes below are merely illustrative of some methods that can be employed for the synthesis of compounds of formula (I). Compounds of the invention may be made by starting with succinic acid, a mono-protected succinic acid, a mono-activated methylmalonic acid a mono-protected methylmalonic acid or a mono-activated methylmalonic acid.

Protecting groups include but are not limited to benzyl and tert-butyl. Other protecting groups for carbonyls and their removal are detailed in 'Greene's Protective Groups in Organic Synthesis' (Wuts and Greene, Wiley, 2006). Protecting groups may be removed by methods known to one skilled in the art including hydrogenation in the presence of a heterogenous catalyst for benzyl esters and treatment with organic or mineral acids, preferably trifluoroacetic acid or dilute HCl, for tert-butyl esters.

Activating groups includes but is not limited to mixed anhydrides and acyl chlorides.

Thus, were compounds of formula (I) are symmetrical then a symmetrical starting material is selected. Either a symmetrical dicarboxylic acid is selected or a di-activated carboxylic acid is selected. Preferably the compound selected is succinic acid or succinyl chloride.

When the compound of formula (I) is asymmetric then the starting material selected is asymmetric. That includes "acid-protected acid", "acid-activated acid", and "protected acid-activated acid". Preferably this includes succinic acid mono-benzyl ester, succinic acid mono-tert butyl ester, 4-chloro-4-oxobutyric acid.

Alternatively for an asymmetric compound of formula (I) a symmetric starting material is selected, preferable succinic acid, and less derivatising starting material is employed. The following general methods are not exhaustive and it will be apparent to one skilled in the art that other methods may be used to generate compounds of the invention. The methods may be used together or separately.

Compounds of formula (I) that contain formula (II) may be made by reacting a carboxylic acid with a suitable alkyl halide (formula (X)). E.g.

wherein Hal represents a halogen (e.g. F, Cl, Br or I) and R1, R2 and R3 are as defined in formula (II). The reaction may conveniently be carried out in a solvent such as dichloromethane, acetone, acetonitrile or N,N-dimethylformamide with a suitable base such as triethylamine, diisopropylethylamine or caesium carbonate at a temperature, for example, in the range from −10° C. to 80° C., particularly at room temperature. The reaction may be performed with optional additives such as sodium iodide or tetraalkyl ammonium halides (e.g. tetrabutyl ammonium iodide).

Compounds of formula X are either commercially available or may be conveniently prepared by literature methods such as those outlined in Journal of the American Chemical Society, 43, 660-7; 1921 or Journal of medicinal chemistry (1992), 35(4), 687-94.

Compounds of formula (I) that contain formula (VII) may be made by reacting an activated carboxylic acid with a compound of formula XIV, optionally in the presence of an activating species.

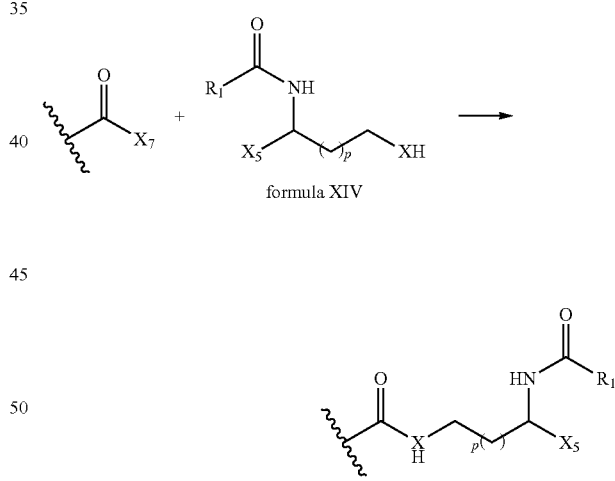

wherein $X_5$ and $R_1$ are as defined in formula (VII) and $X_7$ is Hal (Cl, F, Br) or mixed anhydride. Preferably $X_7$=Cl. The reaction may conveniently be carried out in a solvent such as dichloromethane, acetone, THF, acetonitrile or N,N-dimethylformamide, with a suitable base such as triethylamine, diisopropylethylamine or caesium carbonate with at a temperature, for example, in the range from −10° C. to 80° C., particularly at room temperature.

Compounds of formula (I) that contain formula (VIII) may be made by reacting an activated carboxylic acid with a compound of formula XIV, optionally in the presence of an activating species

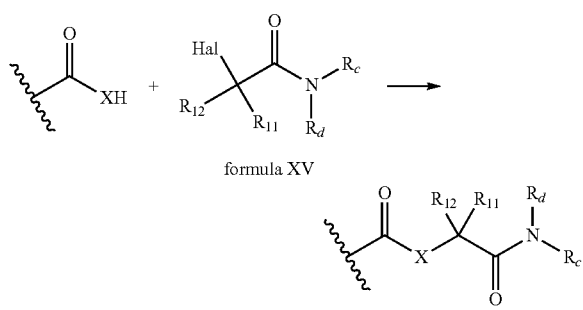

formula XV wherein Hal represents a halogen (e.g. F, Cl, Br or I) and $R_{11}$, $R_{12}$ and $R_c$ and $R_d$ are as defined in formula (VIII). The reaction may conveniently be carried out in a solvent such as dichloromethane, acetone, acetonitrile or N,N-dimethylformamide with a suitable base such as triethylamine, diisopropylethylamine or caesium carbonate at a temperature, for example, in the range from −10° C. to 80° C., particularly at 80° C. The reaction may be performed with optional additives such as sodium iodide or tetraalkyl ammonium halides (e.g. tetrabutyl ammonium iodide).

Compounds of formula X are either commercially available or may be conveniently prepared by literature methods whereby an amine is reacted with an acyl chloride.

Compounds of formula (I) that contain formula (IX) may be made by combining the methods describe above and by other methods known to one skilled in the art.

General Use of the Compounds of the Invention

Compounds as described herein can be used in medicine or in cosmetics, or in the manufacture of a composition for such use. The medicament can be used in any situation where an enhanced or restored energy production (ATP) is desired, such as in the treatment of metabolic diseases, or in the treatment of diseases or conditions of mitochondrial dysfunction, treating or suppressing of mitochondrial disorders. The compounds may be used in the stimulation of mitochondrial energy production and in the restoration of drug-induced mitochondrial dysfunction such as e.g. sensineural hearing loss or tinnitus (side effect of certain antibiotics due to mitochondrial toxicity) or lactic acidosis. The compounds may be used in the treatment of cancer, diabetes, acute starvation, endotoxemia, sepsis, systemic inflammatory response syndrome, multiple organ dysfunction syndrome and following hypoxia, ischemia, stroke, myocardial infarction, acute angina, an acute kidney injury, coronary occlusion and atrial fibrillation, or to avoid or counteract reperfusion injuries. Moreover, it is envisaged that the compounds of the invention may be beneficial in treatment of male infertility.

It is envisaged that the compounds of the invention will provide cell-permeable precursors of components of the Kreb's cycle and optionally glycolysis pathways. It is envisaged that following entry into the cell, enzymatic or chemical hydrolysis will liberate succinate or methylmalonate optionally along with other energy-providing materials, such as acetate and glucose.

The compounds of the invention can be used to enhance or restore energy production in mitochondria. Notably the compounds can be used in medicine or in cosmetics. The compounds can be used in the prevention or treatment of disorders or diseases having a component relating to mitochondrial dysfunction and/or to a component of energy (ATP) deficiency.

Enhancement of energy production is e.g. relevant in subjects suffering from a mitochondrial defect, disorder or disease. Mitochondrial diseases result from dysfunction of the mitochondria, which are specialized compartments present in every cell of the body except red blood cells. When mitochondrial function decreases, the energy generated within the cell reduces and cell injury or cell death will follow. If this process is repeated throughout the body the life of the subject is severely compromised.

Diseases of the mitochondria appear most often in organs that are very energy demanding such as retina, the cochlea, the brain, heart, liver, skeletal muscles, kidney and the endocrine and respiratory system.

Symptoms of a mitochondrial disease may include loss of motor control, muscle weakness and pain, seizures, visual/hearing problems, cardiac diseases, liver diseases, gastrointestinal disorders, swallowing difficulties and more.

A mitochondrial disease may be inherited or may be due to spontaneous mutations, which lead to altered functions of the proteins or RNA molecules normally residing in the mitochondria.

Many diseases have been found to involve a mitochondrial deficiency such as a Complex I, II, III or IV deficiency or an enzyme deficiency like e.g. pyruvate dehydrogenase deficiency. However, the picture is complex and many factors may be involved in the diseases.

Up to now, no curative treatments are available. The only treatments available are such that can alleviate the symptoms and delay the progression of the disease. Accordingly, the findings by the present inventors and described herein are very important as they demonstrate the beneficial effect of the cell permeable compounds of succinic acid on the energy production in the mitochondria.

In addition, in comparison with known succinate prodrugs (such as e.g. mentioned in WO 97/47584), they show improved properties for treatment of these and related diseases, including better cell permeability, longer plasma half-life, reduced toxicity, increased energy release to mitochondria, and improved formulation (due to improved properties including increased solubility). In some cases, the compounds are also orally bioavailable, which allows for easier administration.

Thus the advantageous properties of the compound of the invention may include one or more of the following:
Increased cell permeability
Longer half-life in plasma
Reduced toxicity
Increased energy release to mitochondria
Improved formulation
Increased solubility
Increased oral bioavailability The present invention provides the compound of the invention for use as a pharmaceutical, in particular in the treatment of cellular energy (ATP)-deficiency.

A compound of the invention may be used in the treatment of complex I impairment, either dysfunction of the complex itself or any condition or disease that limits the supply of NADH to Complex I, e.g. dysfunction of Krebs cycle, glycolysis, beta-oxidation, pyruvate metabolism and even transport of glucose or other Complex-I-related substrates).

The present invention also provides a method of treatment of mitochondrial complex I related disorders such as but not limited to, Leigh Syndrome, Leber's hereditary optic neuropathy (LHON), MELAS (mitochondrial encephalomyopathy, lactic acidosis, and stroke-like episodes) and MERRF (myoclonic epilepsy with ragged red fibers), which comprises administering to a subject in need thereof an effective amount of the compound of the invention.

The present invention also provides the use of the compound of the invention for the manufacture of a medicament for the treatment of drug-induced lactic acidosis.

A compound of the invention may also be useful in any condition where extra energy production would potentially be beneficial such as, but not limited to, prolonged surgery and intensive care.

Mitochondria

Mitochondria are organelles in eukaryotic cells, popularly referred to as the "powerhouse" of the cell. One of their primary functions is oxidative phosphorylation. The molecule adenosine triphosphate (ATP) functions as an energy "currency" or energy carrier in the cell, and eukaryotic cells derive the majority of their ATP from biochemical processes carried out by mitochondria. These biochemical processes include the citric acid cycle (the tricarboxylic acid cycle, or Kreb's cycle), which generates reduced nicotinamide adenine dinucleotide (NADH) from oxidized nicotinamide adenine dinucleotide ($NAD^+$) and reduced flavin adenine dinucleotide (FADH2) from oxidized flavin adenine dinucleotide (FAD), as well as oxidative phosphorylation, during which NADH and FADH2 is oxidized back to $NAD^+$ and FAD.

The electrons released by oxidation of NADH are shuttled down a series of protein complexes (Complex I, Complex II, Complex III, and Complex IV) known as the respiratory chain. The oxidation of succinate occurs at Complex II (succinate dehydrogenase complex) and FAD is a prosthetic group in the enzyme complex succinate dehydrogenase (complex II). The respiratory complexes are embedded in the inner membrane of the mitochondrion. Complex IV, at the end of the chain, transfers the electrons to oxygen, which is reduced to water. The energy released as these electrons traverse the complexes is used to generate a proton gradient across the inner membrane of the mitochondrion, which creates an electrochemical potential across the inner membrane. Another protein complex, Complex V (which is not directly associated with Complexes I, II, III and IV) uses the energy stored by the electrochemical gradient to convert ADP into ATP.

The citric acid cycle and oxidative phosphorylation are preceded by glycolysis, in which a molecule of glucose is broken down into two molecules of pyruvate, with net generation of two molecules of ATP per molecule of glucose. The pyruvate molecules then enter the mitochondria, where they are completely oxidized to $CO_2$ and $H_2O$ via oxidative phosphorylation (the overall process is known as aerobic respiration). The complete oxidation of the two pyruvate molecules to carbon dioxide and water yields about at least 28-29 molecules of ATP, in addition to the 2 molecules of ATP generated by transforming glucose into two pyruvate molecules. If oxygen is not available, the pyruvate molecule does not enter the mitochondria, but rather is converted to lactate, in the process of anaerobic respiration.

The overall net yield per molecule of glucose is thus approximately at least 30-31 ATP molecules. ATP is used to power, directly or indirectly, almost every other biochemical reaction in the cell. Thus, the extra (approximately) at least 28 or 29 molecules of ATP contributed by oxidative phosphorylation during aerobic respiration are critical to the proper functioning of the cell. Lack of oxygen prevents aerobic respiration and will result in eventual death of almost all aerobic organisms; a few organisms, such as yeast, are able to survive using either aerobic or anaerobic respiration.

When cells in an organism are temporarily deprived of oxygen, anaerobic respiration is utilized until oxygen again becomes available or the cell dies. The pyruvate generated during glycolysis is converted to lactate during anaerobic respiration. The build-up of lactic acid is believed to be responsible for muscle fatigue during intense periods of activity, when oxygen cannot be supplied to the muscle cells. When oxygen again becomes available, the lactate is converted back into pyruvate for use in oxidative phosphorylation.

Mitochondrial dysfunction contributes to various disease states. Some mitochondrial diseases are due to mutations or deletions in the mitochondrial genome or nuclear. If a threshold proportion of mitochondria in the cell are defective, and if a threshold proportion of such cells within a tissue have defective mitochondria, symptoms of tissue or organ dysfunction can result. Practically any tissue can be affected, and a large variety of symptoms may be present, depending on the extent to which different tissues are involved.

Use of the Compounds of the Invention

The compounds of the invention may be used in any situation where an enhanced or restored energy production (ATP) is desired. Examples are e.g. in all clinical conditions where there is a potential benefit of increased mitochondrial ATP-production or a restoration of mitochondrial function, such as in the restoration of drug-induced mitochondrial dysfunction or lactic acidosis and the treatment of cancer, diabetes, acute starvation, endotoxemia, sepsis, reduced hearing visual acuity, systemic inflammatory response syndrome and multiple organ dysfunction syndrome. The compounds may also be useful following hypoxia, ischemia, stroke, myocardial infarction, acute angina, an acute kidney injury, coronary occlusion, atrial fibrillation and in the prevention or limitations of reperfusion injuries.

In particular, the compounds of the invention can be used in medicine, notably in the treatment or prevention of a mitochondria-related condition, disease or disorder or in cosmetics.

Dysfunction of mitochondria is also described in relation to renal tubular acidosis; motor neuron diseases; other neurological diseases; epilepsy; genetic diseases; Huntington's Disease; mood disorders; schizophrenia; bipolar disorder; age-associated diseases; cerebral vascular accidents, macular degeneration; diabetes; and cancer.

Compounds of the Invention for Use in Mitochondrial Related Disorders or Diseases The compounds according to the invention may be used in the prevention or treatment a mitochondria-related disease selected from the following:

Alpers Disease (Progressive Infantile Poliodystrophy)

Amyotrophic lateral sclerosis (ALS)

Autism

Barth syndrome (Lethal Infantile Cardiomyopathy)

Beta-oxidation Defects

Bioenergetic metabolism deficency

Carnitine-Acyl-Carnitine Deficiency

Carnitine Deficiency

Creatine Deficiency Syndromes (Cerebral Creatine Deficiency Syndromes (CCDS) includes: Guanidinoaceteate Methyltransferase Deficiency (GAMT Deficiency), L-Arginine:Glycine Amidinotransferase Deficiency (AGAT Deficiency), and SLC6A8-Related Creatine Transporter Deficiency (SLC6A8 Deficiency).

Co-Enzyme Q10 Deficiency

Complex I Deficiency (NADH dehydrogenase (NADH-CoQ reductase) deficiency)

Complex II Deficiency (Succinate dehydrogenase deficiency)
Complex III Deficiency (Ubiquinone-cytochrome c oxidoreductase deficiency)
Complex IV Deficiency/COX Deficiency (Cytochrome c oxidase deficiency is caused by a defect in Complex IV of the respiratory chain)
Complex V Deficiency (ATP synthase deficiency)
COX Deficiency
CPEO (Chronic Progressive External Ophthalmoplegia Syndrome)
CPT I Deficiency
CPT II Deficiency
Friedreich's ataxia (FRDA or FA)
Glutaric Aciduria Type II
KSS (Kearns-Sayre Syndrome)
Lactic Acidosis
LCAD (Long-Chain Acyl-CoA Dehydrogenase Deficiency)
LCHAD
Leigh Disease or Syndrome (Subacute Necrotizing Encephalomyelopathy)
LHON (Leber's hereditary optic neuropathy)
Luft Disease
MCAD (Medium-Chain Acyl-CoA Dehydrogenase Deficiency)
MELAS (Mitochondrial Encephalomyopathy Lactic Acidosis and Stroke like Episodes)
MERRF (Myoclonic Epilepsy and Ragged-Red Fiber Disease)
MIRAS (Mitochondrial Recessive Ataxia Syndrome)
Mitochondrial Cytopathy
Mitochondrial DNA Depletion
Mitochondrial Encephalopathy includes: Encephalomyopathy, Encephalomyelopathy
Mitochondrial Myopathy
MNGIE (Myoneurogastointestinal Disorder and Encephalopathy)
NARP (Neuropathy, Ataxia, and Retinitis Pigmentosa)
Neurodegenerative disorders associated with Parkinson's, Alzheimer's or Huntington's disease
Pearson Syndrome
Pyruvate Carboxylase Deficiency
Pyruvate Dehydrogenase Deficiency
POLG Mutations
Respiratory Chain Deficiencies
SCAD (Short-Chain Acyl-CoA Dehydrogenase Deficiency)
SCHAD (Short Chain L-3-Hydroxyacyl-CoA Dehydrogenase (SCHAD) Deficiency, also referred to as 3-Hydroxy Acyl CoA Dehydrogenase Deficiency HADH
VLCAD (Very Long-Chain Acyl-CoA Dehydrogenase Deficiency)
Diabetes
Acute starvation
Endotoxemia
Sepsis
Systemic inflammation response syndrome (SIRS)
Multiple organ failure With reference to information from the web-page of United Mitochondrial Disease Foundation (www.umdf.org), some of the above-mentioned diseases are discussed in more details in the following:

Complex I deficiency: Inside the mitochondrion is a group of proteins that carry electrons along four chain reactions (Complexes I-IV), resulting in energy production. This chain is known as the Electron Transport Chain. A fifth group (Complex V) churns out the ATP. Together, the electron transport chain and the ATP synthase form the respiratory chain and the whole process is known as oxidative phosphorylation or OXPHOS.

Complex I, the first step in this chain, is the most common site for mitochondrial abnormalities, representing as much as one third of the respiratory chain deficiencies. Often presenting at birth or in early childhood, Complex I deficiency is usually a progressive neurodegenerative disorder and is responsible for a variety of clinical symptoms, particularly in organs and tissues that require high energy levels, such as brain, heart, liver, and skeletal muscles. A number of specific mitochondrial disorders have been associated with Complex I deficiency including: Leber's hereditary optic neuropathy (LHON), MELAS, MERRF, and Leigh Syndrome (LS). MELAS stands for (mitochondrial encephalomyopathy, lactic acidosis, and stroke-like episodes) and MERRF stand for myoclonic epilepsy with ragged red fibers.

LHON is characterized by blindness which occurs on average between 27 and 34 years of age; blindness can develop in both eyes simultaneously, or sequentially (one eye will develop blindness, followed by the other eye two months later on average). Other symptoms may also occur, such as cardiac abnormalities and neurological complications.

There are three major forms of Complex I deficiency:
i) Fatal infantile multisystem disorder—characterized by poor muscle tone, developmental delay, heart disease, lactic acidosis, and respiratory failure.
ii) Myopathy (muscle disease)—starting in childhood or adulthood, and characterized by weakness or exercise intolerance.
iii) Mitochondrial encephalomyopathy (brain and muscle disease)—beginning in childhood or adulthood and involving variable symptom combinations which may include: eye muscle paralysis, pigmentary retinopathy (retinal color changes with loss of vision), hearing loss, sensory neuropathy (nerve damage involving the sense organs), seizures, dementia, ataxia (abnormal muscle coordination), and involuntary movements. This form of Complex I deficiency may cause Leigh Syndrome and MELAS.

Most cases of Complex I deficiency result from autosomal recessive inheritance (combination of defective nuclear genes from both the mother and the father). Less frequently, the disorder is maternally inherited or sporadic and the genetic defect is in the mitochondrial DNA.

Treatment: As with all mitochondrial diseases, there is presently no cure for Complex I deficiency. A variety of treatments, which may or may not be effective, can include such metabolic therapies as: riboflavin, thiamine, biotin, co-enzyme Q10, carnitine, and ketogenic diet. Therapies for the infantile multisystem form have been unsuccessful.

The clinical course and prognosis for Complex I patients is highly variable and may depend on the specific genetic defect, age of onset, organs involved, and other factors.

Complex III Deficiency: The symptoms include four major forms:
i) Fatal infantile encephalomyopathy, congenital lactic acidosis, hypotonia, dystrophic posturing, seizures, and coma. Ragged-red fibers in muscle tissue are common.
ii) Encephalomyopathies of later onset (childhood to adult life): various combinations of weakness, short stature, ataxia, dementia, hearing loss, sensory neuropathy, pigmentary retinopathy, and pyramidal signs. Ragged-red fibers are common. Possible lactic acidosis.

iii) Myopathy, with exercise intolerance evolving into fixed weakness. Ragged-red fibers are common. Possible lactic acidosis.

iv) Infantile histiocytoid cardiomyopathy.

Complex IV Deficiency/COX Deficiency: The symptoms include two major forms:
1. Encephalomyopathy: Typically normal for the first 6 to 12 months of life and then show developmental regression, ataxia, lactic acidosis, optic atrophy, ophthalmoplegia, nystagmus, dystonia, pyramidal signs, and respiratory problems. Frequent seizures. May cause Leigh Syndrome
2. Myopathy: Two main variants:
   1. Fatal infantile myopathy: may begin soon after birth and accompanied by hypotonia, weakness, lactic acidosis, ragged-red fibers, respiratory failure, and kidney problems.
   2. Benign infantile myopathy: may begin soon after birth and accompanied by hypotonia, weakness, lactic acidosis, ragged-red fibers, respiratory problems, but (if the child survives) followed by spontaneous improvement.

KSS (Kearns-Sayre Syndrome): KSS is a slowly progressive multi-system mitochondrial disease that often begins with drooping of the eyelids (ptosis). Other eye muscles eventually become involved, resulting in paralysis of eye movement. Degeneration of the retina usually causes difficulty seeing in dimly lit environments.

KSS is characterized by three main features:
typical onset before age 20 although may occur in infancy or adulthood
paralysis of specific eye muscles (called chronic progressive external ophthalmoplegia—CPEO)
degeneration of the retina causing abnormal accumulation of pigmented (colored) material (pigmentary retinopathy).

In addition, one or more of the following conditions is present:
block of electrical signals in the heart (cardiac conduction defects)
elevated cerebrospinal fluid protein
incoordination of movements (ataxia).

Patients with KSS may also have such problems as deafness, dementia, kidney dysfunction, and muscle weakness. Endocrine abnormalities including growth retardation, short stature, or diabetes may also be evident.

KSS is a rare disorder. It is usually caused by a single large deletion (loss) of genetic material within the DNA of the mitochondria (mtDNA), rather than in the DNA of the cell nucleus. These deletions, of which there are over 150 species, typically arise spontaneously. Less frequently, the mutation is transmitted by the mother.

As with all mitochondrial diseases, there is no cure for KSS.

Treatments are based on the types of symptoms and organs involved, and may include: Coenzyme Q10, insulin for diabetes, cardiac drugs, and a cardiac pacemaker which may be life-saving. Surgical intervention for drooping eyelids may be considered but should be undertaken by specialists in ophthalmic surgical centers.

KSS is slowly progressive and the prognosis varies depending on severity. Death is common in the third or fourth decade and may be due to organ system failures.

Leigh Disease or Syndrome (Subacute Necrotizing Encephalomyelopathy): Symptoms: Seizures, hypotonia, fatigue, nystagmus, poor reflexes, eating and swallowing difficulties, breathing problems, poor motor function, ataxia.

Causes: Pyruvate Dehydrogenase Deficiency, Complex I Deficiency, Complex II Deficiency, Complex IV/COX Deficiency, NARP.

Leigh's Disease is a progressive neurometabolic disorder with a general onset in infancy or childhood, often after a viral infection, but can also occur in teens and adults. It is characterized on MRI by visible necrotizing (dead or dying tissue) lesions on the brain, particularly in the midbrain and brainstem.

The child often appears normal at birth but typically begins displaying symptoms within a few months to two years of age, although the timing may be much earlier or later. Initial symptoms can include the loss of basic skills such as sucking, head control, walking and talking. These may be accompanied by other problems such as irritability, loss of appetite, vomiting and seizures. There may be periods of sharp decline or temporary restoration of some functions. Eventually, the child may also have heart, kidney, vision, and breathing complications.

There is more than one defect that causes Leigh's Disease. These include a pyruvate dehydrogenase (PDHC) deficiency, and respiratory chain enzyme defects—Complexes I, II, IV, and V. Depending on the defect, the mode of inheritance may be X-linked dominant (defect on the X chromosome and disease usually occurs in males only), autosomal recessive (inherited from genes from both mother and father), and maternal (from mother only). There may also be spontaneous cases which are not inherited at all.

There is no cure for Leigh's Disease. Treatments generally involve variations of vitamin and supplement therapies, often in a "cocktail" combination, and are only partially effective. Various resource sites include the possible usage of: thiamine, coenzyme Q10, riboflavin, biotin, creatine, succinate, and idebenone. Experimental drugs, such as dichloroacetate (DCA) are also being tried in some clinics. In some cases, a special diet may be ordered and must be monitored by a dietitian knowledgeable in metabolic disorders.

The prognosis for Leigh's Disease is poor. Depending on the defect, individuals typically live anywhere from a few years to the mid-teens. Those diagnosed with Leigh-like syndrome or who did not display symptoms until adulthood tend to live longer.

MELAS (Mitochondrial Encephalomyopathy Lactic Acidosis and Stroke-like Episodes): Symptoms: Short statue, seizures, stroke-like episodes with focused neurological deficits, recurrent headaches, cognitive regression, disease progression, ragged-red fibers.

Cause: Mitochondrial DNA point mutations: A3243G (most common)

MELAS—Mitochondrial Myopathy (muscle weakness), Encephalopathy (brain and central nervous system disease), Lactic Acidosis (build-up of a product from anaerobic respiration), and Stroke-like episodes (partial paralysis, partial vision loss, or other neurological abnormalities).

MELAS is a progressive neurodegenerative disorder with typical onset between the ages of 2 and 15, although it may occur in infancy or as late as adulthood. Initial symptoms may include stroke-like episodes, seizures, migraine headaches, and recurrent vomiting.

Usually, the patient appears normal during infancy, although short stature is common. Less common are early infancy symptoms that may include developmental delay, learning disabilities or attention-deficit disorder. Exercise intolerance, limb weakness, hearing loss, and diabetes may also precede the occurrence of the stroke-like episodes.

Stroke-like episodes, often accompanied by seizures, are the hallmark symptom of MELAS and cause partial paralysis, loss of vision, and focal neurological defects. The gradual cumulative effects of these episodes often result in variable combinations of loss of motor skills (speech, movement, and eating), impaired sensation (vision loss and loss of body sensations), and mental impairment (dementia). MELAS patients may also suffer additional symptoms including: muscle weakness, peripheral nerve dysfunction, diabetes, hearing loss, cardiac and kidney problems, and digestive abnormalities. Lactic acid usually accumulates at high levels in the blood, cerebrospinal fluid, or both.

MELAS is maternally inherited due to a defect in the DNA within mitochondria. There are at least 17 different mutations that can cause MELAS. By far the most prevalent is the A3243G mutation, which is responsible for about 80% of the cases.

There is no cure or specific treatment for MELAS. Although clinical trials have not proven their efficacy, general treatments may include such metabolic therapies as: CoQ10, creatine, phylloquinone, and other vitamins and supplements. Drugs such as seizure medications and insulin may be required for additional symptom management. Some patients with muscle dysfunction may benefit from moderate supervised exercise. In select cases, other therapies that may be prescribed include dichloroacetate (DCA) and menadione, though these are not routinely used due to their potential for having harmful side effects.

The prognosis for MELAS is poor. Typically, the age of death is between 10 to 35 years, although some patients may live longer. Death may come as a result of general body wasting due to progressive dementia and muscle weakness, or complications from other affected organs such as heart or kidneys.

MERRF is a progressive multi-system syndrome usually beginning in childhood, but onset may occur in adulthood. The rate of progression varies widely. Onset and extent of symptoms can differ among affected siblings.

The classic features of MERRF include:
Myoclonus (brief, sudden, twitching muscle spasms)—the most characteristic symptom
Epileptic seizures
Ataxia (impaired coordination)
Ragged-red fibers (a characteristic microscopic abnormality observed in muscle biopsy of patients with MERRF and other mitochondrial disorders) Additional symptoms may include: hearing loss, lactic acidosis (elevated lactic acid level in the blood), short stature, exercise intolerance, dementia, cardiac defects, eye abnormalities, and speech impairment.

Although a few cases of MERRF are sporadic, most cases are maternally inherited due to a mutation within the mitochondria. The most common MERRF mutation is A8344G, which accounted for over 80% of the cases. Four other mitochondrial DNA mutations have been reported to cause MERRF. While a mother will transmit her MERRF mutation to all of her offspring, some may never display symptoms.

As with all mitochondrial disorders, there is no cure for MERRF. Therapies may include coenzyme Q10, L-carnitine, and various vitamins, often in a "cocktail" combination. Management of seizures usually requires anticonvulsant drugs. Medications for control of other symptoms may also be necessary.

The prognosis for MERRF varies widely depending on age of onset, type and severity of symptoms, organs involved, and other factors.

Mitochondrial DNA Depletion: The symptoms include three major forms:
1. Congenital myopathy: Neonatal weakness, hypotonia requiring assisted ventilation, possible renal dysfunction. Severe lactic acidosis. Prominent ragged-red fibers. Death due to respiratory failure usually occurs prior to one year of age.
2. Infantile myopathy: Following normal early development until one year old, weakness appears and worsens rapidly, causing respiratory failure and death typically within a few years.
3. Hepatopathy: Enlarged liver and intractable liver failure, myopathy. Severe lactic acidosis. Death is typical within the first year.

Friedreich's Ataxia

Friedreich's ataxia (FRDA or FA) an autosomal recessive neurodegenerative and cardiodegenerative disorder caused by decreased levels of the protein frataxin. Frataxin is important for the assembly of iron-sulfur clusters in mitochondrial respiratory-chain complexes. Estimates of the prevalence of FRDA in the United States range from 1 in every 22,000-29,000 people (see www.nlm.nih.gov/medlineplus/ency/article/001411.htm) to 1 in 50,000 people. The disease causes the progressive loss of voluntary motor coordination (ataxia) and cardiac complications. Symptoms typically begin in childhood, and the disease progressively worsens as the patient grows older; patients eventually become wheelchair-bound due to motor disabilities.

In addition to congenital disorders involving inherited defective mitochondria, acquired mitochondrial dysfunction has been suggested to contribute to diseases, particularly neurodegenerative disorders associated with aging like Parkinson's, Alzheimer's, and Huntington's Diseases. The incidence of somatic mutations in mitochondrial DNA rises exponentially with age; diminished respiratory chain activity is found universally in aging people. Mitochondrial dysfunction is also implicated in excitotoxicity, neuronal injury, cerebral vascular accidents such as that associated with seizures, stroke and ischemia.

Pharmaceutical Compositions Comprising a Compound of the Invention

The present invention also provides a pharmaceutical composition comprising the compound of the invention together with one or more pharmaceutically acceptable diluents or carriers.

The compound of the invention or a formulation thereof may be administered by any conventional method for example but without limitation it may be administered parenterally, orally, topically (including buccal, sublingual or transdermal), via a medical device (e.g. a stent), by inhalation or via injection (subcutaneous or intramuscular). The treatment may consist of a single dose or a plurality of doses over a period of time.

The treatment may be by administration once daily, twice daily, three times daily, four times daily etc. The treatment may also be by continuous administration such as e.g. administration intravenous by drop.

Whilst it is possible for the compound of the invention to be administered alone, it is preferable to present it as a pharmaceutical formulation, together with one or more acceptable carriers. The carrier(s) must be "acceptable" in the sense of being compatible with the compound of the invention and not deleterious to the recipients thereof. Examples of suitable carriers are described in more detail below.

The formulations may conveniently be presented in unit dosage form and may be prepared by any of the methods well known in the art of pharmacy. Such methods include the step of bringing into association the active ingredient (compound of the invention) with the carrier which constitutes one or more accessory ingredients. In general the formulations are prepared by uniformly and intimately bringing into association the active ingredient with liquid carriers or finely divided solid carriers or both, and then, if necessary, shaping the product.

The compound of the invention will normally be administered intravenously, orally or by any parenteral route, in the form of a pharmaceutical formulation comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

For example, the compound of the invention can also be administered orally, buccally or sublingually in the form of tablets, capsules, ovules, elixirs, solutions or suspensions, which may contain flavouring or colouring agents, for immediate-, delayed- or controlled-release applications.

Formulations in accordance with the present invention suitable for oral administration may be presented as discrete units such as capsules, cachets or tablets, each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Solutions or suspensions of the compound of the invention suitable for oral administration may also contain excipients e.g. N,N-dimethylacetamide, dispersants e.g. polysorbate 80, surfactants, and solubilisers, e.g. polyethylene glycol, Phosal 50 PG (which consists of phosphatidylcholine, soya-fatty acids, ethanol, mono/diglycerides, propylene glycol and ascorbyl palmitate). The formulations according to present invention may also be in the form of emulsions, wherein a compound according to Formula (I) may be present in an aqueous oil emulsion. The oil may be any oil-like substance such as e.g. soy bean oil or safflower oil, medium chain triglycieride (MCT-oil) such as e.g. coconut oil, palm oil etc or combinations thereof.

Tablets may contain excipients such as microcrystalline cellulose, lactose (e.g. lactose monohydrate or lactose anyhydrous), sodium citrate, calcium carbonate, dibasic calcium phosphate and glycine, butylated hydroxytoluene (E321), crospovidone, hypromellose, disintegrants such as starch (preferably corn, potato or tapioca starch), sodium starch glycollate, croscarmellose sodium, and certain complex silicates, and granulation binders such as polyvinylpyrrolidone, hydroxypropylmethylcellulose (HPMC), hydroxy-propyl-cellulose (HPC), macrogol 8000, sucrose, gelatin and acacia. Additionally, lubricating agents such as magnesium stearate, stearic acid, glyceryl behenate and talc may be included.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant, inert diluent, preservative, disintegrant (e.g. sodium starch glycolate, cross-linked povidone, cross-linked sodium carboxymethyl cellulose), surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethylcellulose in varying proportions to provide desired release profile.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

Pharmaceutical compositions adapted for topical administration may be formulated as ointments, creams, suspensions, lotions, powders, solutions, pastes, gels, impregnated dressings, sprays, aerosols or oils, transdermal devices, dusting powders, and the like. These compositions may be prepared via conventional methods containing the active agent. Thus, they may also comprise compatible conventional carriers and additives, such as preservatives, solvents to assist drug penetration, emollient in creams or ointments and ethanol or oleyl alcohol for lotions. Such carriers may be present as from about 1% up to about 98% of the composition. More usually they will form up to about 80% of the composition. As an illustration only, a cream or ointment is prepared by mixing sufficient quantities of hydrophilic material and water, containing from about 5-10% by weight of the compound, in sufficient quantities to produce a cream or ointment having the desired consistency.

Pharmaceutical compositions adapted for transdermal administration may be presented as discrete patches intended to remain in intimate contact with the epidermis of the recipient for a prolonged period of time. For example, the active agent may be delivered from the patch by iontophoresis.

For applications to external tissues, for example the mouth and skin, the compositions are preferably applied as a topical ointment or cream. When formulated in an ointment, the active agent may be employed with either a paraffinic or a water-miscible ointment base.

Alternatively, the active agent may be formulated in a cream with an oil-in-water cream base or a water-in-oil base.

For parenteral administration, fluid unit dosage forms are prepared utilizing the active ingredient and a sterile vehicle, for example but without limitation water, alcohols, polyols, glycerine and vegetable oils, water being preferred. The active ingredient, depending on the vehicle and concentration used, can be either colloidal, suspended or dissolved in the vehicle. In preparing solutions the active ingredient can be dissolved in water for injection and filter sterilised before filling into a suitable vial or ampoule and sealing.

Advantageously, agents such as local anaesthetics, preservatives and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability.

Parenteral suspensions are prepared in substantially the same manner as solutions, except that the active ingredient is suspended in the vehicle instead of being dissolved and sterilization cannot be accomplished by filtration. The active ingredient can be sterilised by exposure to ethylene oxide before suspending in the sterile vehicle. Advantageously, a surfactant or wetting agent is included in the composition to facilitate uniform distribution of the active ingredient.

It should be understood that in addition to the ingredients particularly mentioned above the formulations of this invention may include other agents conventional in the art having regard to the type of formulation in question, for example those suitable for oral administration may include flavouring agents. A person skilled in the art will know how to choose a suitable formulation and how to prepare it (see eg Remington's Pharmaceutical Sciences 18 Ed. or later). A person skilled in the art will also know how to choose a suitable administration route and dosage.

It will be recognized by one of skill in the art that the optimal quantity and spacing of individual dosages of a compound of the invention will be determined by the nature and extent of the condition being treated, the form, route and site of administration, and the age and condition of the particular subject being treated, and that a physician will ultimately determine appropriate dosages to be used. This dosage may be repeated as often as appropriate. If side effects develop the amount and/or frequency of the dosage can be altered or reduced, in accordance with normal clinical practice.

All % values mentioned herein are % w/w unless the context requires otherwise.

Compounds of the invention all may be transformed in a biological matrix to liberate succinic acid, succinyl coenzyme A or canonical forms of the same. They may do so as follows.

Where R', R" or R'" is a compound of formula (II) the acyl group including $R_2$ may be cleaved by a suitable enzyme, preferably an esterase. This liberates an hydroxymethyl ester, an aminomethyl ester or a thiolmethyl ester which could spontaneous covert to a carbonyl, imine or thiocarbonyl group and a free carboxylic acid. By way of example in formula (I) where A is OR' with R' being formula (II) and B is H and Z is —$CH_2CH_2$—.

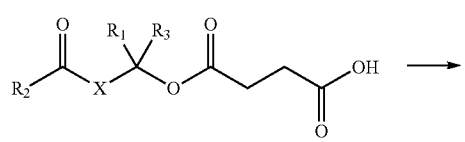

-continued

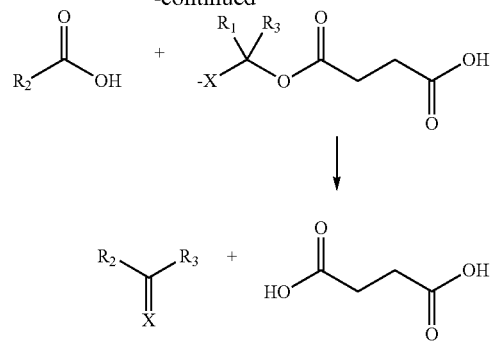

When B is —SR'" a thiol group is released. This is regarded as especially advantageous as the thiol group has reductive properties. Many diseases have an unwanted oxidative stress component, which may lead to damage to cell structure and cell function. Accordingly, release of a component which can act as an anti-oxidant and scavenge free radicals or reduce oxygen-reactive species is expected to give extra benefit in medical or cosmetic use.

Where R', R" or R'" is a compound of formula (V) the substituent on group $R_{10}$ may be removed by the action of a suitable enzyme or via chemical hydrolysis in vivo. By way of example in formula (I) where A is OR' with R' being formula (V) and B is H and Z is —$CH_2CH_2$—, X is O and R8 is H, R9 is Me and R10 is O-acetyl.

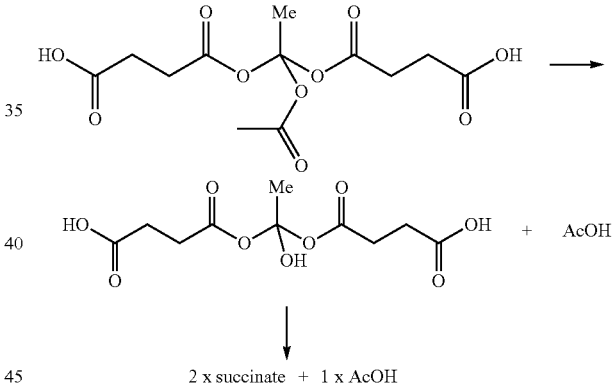

2 x succinate + 1 x AcOH

Where R', R" or R'" is a compound of formula (VII) the group may be removed by the action of a suitable enzyme or via chemical hydrolysis in vivo to liberate succinic acid. By way of example in formula (I) where A is SR with R being formula (VII) and B is OH and Z is —$CH_2CH_2$—, $X_5$ is $CO_2H$ and $R_1$ is Et:

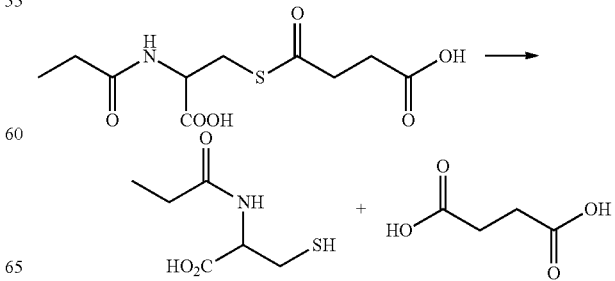

Alternatively for compounds of formula VII the entity in itself may be taken directly into the Krebs cycle in the place of succinyl-CoA.

Where formula (I) is

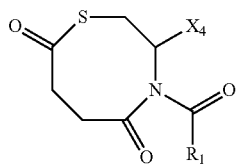

the compound may hydrolyse to give a compound according to the scheme below and when $X_4$ is —COOH.

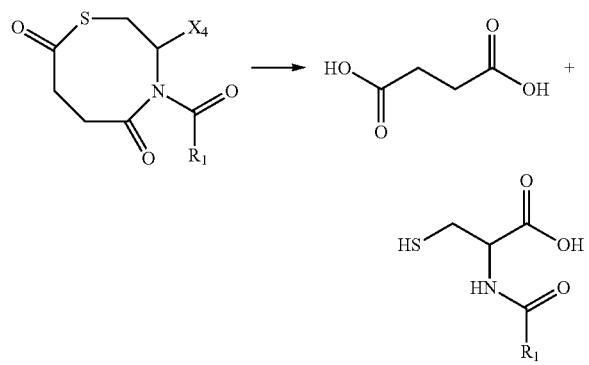

Other Aspects of the Invention

The present invention also provides a combination (for example for the treatment of mitochondrial dysfunction) of a compound of formula (I) or a pharmaceutically acceptable form thereof as hereinbefore defined and one or more agents independently selected from:
  Quinone derivatives, e.g. Ubiquinone, Idebenone, MitoQ
  Vitamins e.g. Tocopherols, Tocotrienols and Trolox (Vitamin E), Ascorbate (C), Thiamine (B1), Riboflavin (B2), Nicotinamide (B3), Menadione (K3),
  Antioxidants in addition to vitamins e.g. TPP-compounds (MitoQ), Sk-compounds, Epicatechin, Catechin, Lipoic acid, Uric acid, Melatonin
  Dichloroacetate
  Methylene blue
  l-arginine
  Szeto-Schiller peptides
  Creatine
  Benzodiazepines
  Modulators of PGC-1α
  Ketogenic diet One other aspect of the invention is that any of the compounds as disclosed herein may be administered together with any other compounds such as e.g. sodium bicarbonate (as a bolus (e.g. 1 mEq/kg) followed by a continuous infusion.) as a concomitant medication to the compounds as disclosed herein.

Lactic Acidosis or Drug-Induced Side-Effects Due to Complex I-Related Impairment of Mitochondrial Oxidative Phosphorylation The present invention also relates to the prevention or treatment of lactic acidosis and of mitochondrial-related drug-induced side effects. In particular the compounds according to the invention are used in the prevention or treatment of a mitochondrial-related drug-induced side effects at or up-stream of Complex I, or expressed otherwise, the invention provides according to the invention for the prevention or treatment of drug-induced direct inhibition of Complex I or of any drug-induced effect that limits the supply of NADH to Complex I (such as, but not limited to, effects on Krebs cycle, glycolysis, beta-oxidation, pyruvate metabolism and even drugs that effects the transport or levels of glucose or other complex I related substrates).

Mitochondrial toxicity induced by drugs may be a part of the desired therapeutic effect (e.g. mitochondrial toxicity induced by cancer drugs), but in most case mitochondrial toxicity induced by drugs is an unwanted effect. Mitochondrial toxicity can markedly increase glycolysis to compensate for cellular loss of mitochondrial ATP formation by oxidative phosphorylation. This can result in increased lactate plasma levels, which if excessive results in lactic acidosis, which can be lethal. Type A lactic acidosis is primarily associated with tissue hypoxia, whereas type B aerobic lactic acidosis is associated with drugs, toxin or systemic disorders such as liver diseases, diabetes, cancer and inborn errors of metabolism (e.g. mitochondrial genetic defects).

Many known drug substances negatively influence mitochondrial respiration (e.g. antipsychotics, local anaesthetics and anti-diabetics) and, accordingly, there is a need to identify or develop means that either can be used to circumvent or alleviate the negative mitochondrial effects induced by the use of such a drug substance.

The present invention provides compounds for use in the prevention or treatment of lactic acidosis and of mitochondrial-related drug-induced side effects. In particular the succinate prodrugs are used in the prevention or treatment of a mitochondrial-related drug-induced side effects at or up-stream of Complex I, or expressed otherwise, the invention provides succinate prodrugs for the prevention or treatment of drug-induced direct inhibition of Complex I or of any drug-induced effect that limits the supply of NADH to Complex I (such as, but not limited to, effects on Krebs cycle, glycolysis, beta-oxidation, pyruvate metabolism and even drugs that effects the transport or levels of glucose or other Complex I related substrates).

As mentioned above, increased lactate plasma levels are often observed in patients treated with drugs that may have mitochondrial-related side effects. The present invention is based on experimental results showing that metformin (first-line treatment for type 2 diabetes and which has been associated with lactic acidosis as a rare side-effect) inhibits mitochondrial function of human peripheral blood cells at Complex I in a time- and dose-dependent fashion at concentrations relevant for metformin intoxication. Metformin further causes a significant increase in lactate production by intact platelets over time. The use of the compounds according to the invention significantly reduced lactate production in metformin-exposed intact platelets. Exogenously applied succinate, the substrate itself, did not reduce the metformin-induced production of lactate.

In another study, the production of lactate was observed over several hours in rotenone-inhibited platelets (i.e. a condition where the function of complex I is impaired). The use of the compounds according to the invention (but not succinate) attenuated the rotenone-induced lactate production of intact human platelets. Respirometric experiments were repeated in human fibroblasts and human heart muscle fibres, and confirmed the findings seen in blood cells.

Accordingly, the invention provides compounds according to Formula (I) for use in the prevention of treatment of lactic acidosis. However, as the results reported herein are based on lactic acidosis related to direct inhibition of Complex I or associated with a defect at or up-stream of Complex I, it is contemplated that the compounds according to the invention are suitable for use in the prevention or treatment of a mitochondrial-related drug-induced side-effects at or up-stream of Complex I. The compounds according to the invention would also counteract drug effects disrupting metabolism up-stream of complex I (indirect inhibition of Complex I, which would encompass any drug effect that limits the supply of NADH to Complex I, e.g. effects on Krebs cycle, glycolysis, beta-oxidation, pyruvate metabolism and even drugs that affect the levels of glucose or other complex I related substrates).

It is contemplated that the compounds according to the invention also can be used in industrial applications, e.g. in vitro to reduce or inhibit formation of lactate or to increase the ATP-availability of commercial or industrial cell lines. Examples include the use in cell culture, in organ preservation, etc.

The compounds according to the invention are used in the treatment or prevention of drug-induced mitochondrial-related side-effects or to increase or restore cellular levels of energy (ATP), in the treatment. Especially, they are used in the treatment or prevention of direct or indirect drug-induced Complex I mitochondrial-related side-effects. In particular, they are used in the treatment or prevention of lactic acidosis, such as lactic acidosis induced by a drug substance.

The invention also relates to a combination of a compound of Formula (I) and a drug substance that may induce a mitochondrial-related side-effect, in particular a side-effect that is caused by direct or indirect impairment of Complex I by the drug substance. Such combination can be used as prophylactic prevention of a mitochondrial-related side-effect or, in case the side-effect appears, in alleviating and/or treating the mitochondrial-related side effect.

It is contemplated that compounds as described below will be effective in treatment or prevention of drug-induced side-effects, in particular in side-effects related to direct or indirect inhibition of Complex I.

Drug substances that are known to give rise in Complex I defects, malfunction or impairment and/or are known to have lactic acidosis as side-effect are:
Analgesics including acetaminophen, capsaicin
Antianginals including amiodarone, perhexiline
Antibiotics including linezolid, trovafloxacin, gentamycin
Anticancer drugs including quinones including mitomycin C, adriamycin
Anti-convulsant drugs including valproic acid
Anti-diabetics including metformin, phenformin, butyl-biguanide, troglitazone and rosiglitazone, pioglitazone
Anti-Hepatitis B including fialuridine
Antihistamines
Anti-Parkinson including tolcapone
Anti-psycotics Risperidone,
Anti-schizoprenia zotepine, clozapine
Antiseptics, quaternary ammonium compounds (QAC)
Anti-tuberculosis including isoniazid
Fibrates including clofibrate, ciprofibrate, simvastatin
Hypnotics including Propofol
Immunosupressive disease-modifying antirheumatic drug (DMARD) Leflunomide
Local anaesthetics including bupivacaine, diclofenac, indomethacin, and lidocaine
Muscle relaxant including dantrolene Neuroleptics including antipsycotic neuroleptics like chlorpromazine, fluphenazine and haloperidol
NRTI (Nucleotide reverse Transcriptase Inhibitors) including efavirenz, tenofovir, emtricitabine, zidovudine, lamivudine, rilpivirine, abacavir, didanosine
NSAIDs including nimesulfide, mefenamic acid, sulindac
Barbituric acids.

Other drug substances that are known to have lactic acidosis as side-effects include beta2-agonists, epinephrine, theophylline or other herbicides. Alcohols and cocaine can also result in lactic acidosis.

Moreover, it is contemplated that the compounds of the invention also may be effective in the treatment or prevention of lactic acidosis even if it is not related to a Complex I defect.

Combination of Drugs and Compounds of the Invention

The present invention also relates to a combination of a drug substance and a compound of the invention for use in the treatment and/or prevention of a drug-induced side-effect selected from lactic acidosis and side-effect related to a Complex I defect, inhibition or malfunction, wherein
i) the drug substance is used for treatment of a disease for which the drug substance is indicated, and
ii) the compound of the invention is used for prevention or alleviation of the side effects induced or inducible by the drug substance, wherein the side-effects are selected from lactic acidosis and side-effects related to a Complex I defect, inhibition or malfunction.

Any combination of such a drug substance with any compound of the invention is within the scope of the present invention. Accordingly, based on the disclosure herein a person skilled in the art will understand that the gist of the invention is the findings of the valuable properties of compounds of the invention to avoid or reduce the side-effects described herein. Thus, the potential use of compounds of the invention capable of entering cells and deliver succinate and possibly other active moeties in combination with any drug substance that has or potentially have the side-effects described herein is evident from the present disclosure.

The invention further relates to
i) a composition comprising a drug substance and a compound of the invention, wherein the drug substance has a potential drug-induced side-effect selected from lactic acidosis and side-effects related to a Complex I defect, inhibition or malfunction,
ii) a composition as described above under i), wherein the compound of the invention is used for prevention or alleviation of side effects induced or inducible by the drug substance, wherein the side-effects are selected from lactic acidosis and side-effects related to a Complex I defect, inhibition or malfunction.

The composition may be in the form of two separate packages:
A first package containing the drug substance or a composition comprising the drug substance and
a second package containing the compound of the invention or a composition comprising the compound of the invention.
The composition may also be a single composition comprising both the drug substance and the compound of the invention.

In the event that the composition comprises two separate packages, the drug substance and the compound of the invention may be administered by different administration routes (e.g. drug substance via oral administration and compound of the invention by parenteral or mucosal administration) and/or they may be administered essentially at the same time or the drug substance may be administered before the compound of the invention or vice versa.

Kits

The invention also provides a kit comprising i) a first container comprising a drug substance, which has a potential drug-induced side-effect selected from lactic acidosis and side-effects related to a Complex I defect, inhibition or malfunction, and ii) a second container comprising a compound of the invention, which has the potential for prevention or alleviation of the side effects induced or inducible by the drug substance, wherein the side-effects are selected from lactic acidosis and side-effects related to a Complex I defect, inhibition or malfunction.

Method for Treatment/Prevention of Side-Effects

The invention also relates to a method for treating a subject suffering from a drug-induced side-effect selected from lactic acidosis and side-effect related to a Complex I defect, inhibition or malfunction, the method comprises administering an effective amount of a compound of the invention to the subject, and to a method for preventing or alleviating a drug-induced side-effect selected from lactic acidosis and side-effect related to a Complex I defect, inhibition or malfunction in a subject, who is suffering from a disease that is treated with a drug substance, which potentially induce a side-effect selected from lactic acidosis and side-effect related to a Complex I defect, inhibition or malfunction, the method comprises administering an effective amount of a compound of the invention to the subject before, during or after treatment with said drug substance.

Metformin

Metformin is an anti-diabetic drug belonging to the class of biguanides. It's the first line treatment for type 2 diabetes, which accounts for around 90% of diabetes cases in the USA. The anti-diabetic effect has been attributed to decreasing hepatic glucose production, increasing the biological effect of insulin through increased glucose uptake in peripheral tissues and decreasing uptake of glucose in the intestine, but the exact mechanisms of action have not been completely elucidated. Despite its advantages over other anti-diabetics it has been related to rare cases of lactic acidosis (LA) as side effect). LA is defined as an increased anion gap, an arterial blood lactate level above 5 mM and a pH≤7.35. Although the precise pathogenesis of metformin-associated LA is still not completely revealed, an inhibition of gluconeogenesis and resulting accumulation of gluconeogenic precursors, such as alanine, pyruvate and lactate, has been suggested. Others, however, propose an interference of the drug with mitochondrial function being the key factor for both the primary therapeutic, glucose-lowering effect as well as for the development of metformin-associated LA). As a consequence of mitochondrial inhibition, the cell would partly shift from aerobic to anaerobic metabolism, promoting glycolysis with resulting elevated lactate levels. Phenformin, another anti-diabetic agent of the same drug class as metformin, has been withdrawn from the market in most countries due to a high incidence of LA (4 cases per 10000 treatment-years). In comparison, the incidence of LA for metformin is about a tenth of that for phenformin, and it is therefore considered a rather safe therapeutic agent. Metformin-associated LA is seen mostly in patients who have additional predisposing conditions affecting the cardiovascular system, liver or kidneys. Under these conditions, the drug clearance from the body is impaired which, if not detected in time, results in escalating blood concentrations of metformin. Since the use of metformin is expected to rise due to increasing prevalence of type 2 diabetes, the research on metformin-induced mitochondrial toxicity and LA becomes a current and urgent issue. Research on the mitochondrial toxicity of metformin reports inconsistent results. Kane et al. (2010) did not detect inhibition of basal respiration and maximal respiratory capacities by metformin in vivo in skeletal muscle from rats and neither did in muscle biopsies of metformin-treated type 2 diabetes patients. In contrast, others have described toxic effects of metformin and phenformin on mitochondria and its association with LA in animal tissues. Data on human tissue are scarce, especially ex vivo or in vivo. Most human data on metformin and LA are based on retrospective studies due to the difficulty of obtaining human tissue samples. Protti et al. (2010), however, reported decreased systemic oxygen consumption in patients with biguanide-associated LA and both Protti et al. (2012b) and Larsen et al. (2012) described mitochondrial dysfunction in vitro in response to metformin exposure at ≤10 mM in human skeletal muscle and platelets, respectively. Protti et al. (2012b) further reported on increased lactate release in human platelets in response to metformin exposure at 1 mM. Although metformin is not found at this concentration at therapeutic conditions, it has been shown to approach these levels in the blood during intoxication and it is known to accumulate 7 to 10-fold in the gastrointestinal tract, kidney, liver, salivary glands, lung, spleen and muscle as compared to plasma.

In the study reported herein the aim was to assess mitochondrial toxicity of metformin and phenformin in human blood cells using high-resolution respirometry. Phenformin was included to compare activity of the two similarly structured drugs and to study the relation between mitochondrial toxicity and the incidence of LA described in human patients. In order to investigate membrane permeability and the specific target of toxicity of these biguanides, a model for testing drug toxicity was applied using both intact and permeabilized blood cells with sequential additions of respiratory complex-specific substrates and inhibitors.

Other aspects appear from the appended claims. All details and particulars apply mutatis mutandis to these aspects.

DEFINITIONS

The articles "a" and "an" are used herein to refer to one or to more than one (i.e. at least one) of the grammatical objects of the article. By way of example "an analogue" means one analogue or more than one analogue.

As used herein the terms "cell permeable succinates", "compound(s) of the invention", "cell-permeable succinate derivatives" and "cell permeable precursors of succinate" are used interchangeably and refer to compounds of formula (I).

As used herein, the term "bioavailability" refers to the degree to which or rate at which a drug or other substance is absorbed or becomes available at the site of biological activity after administration. This property is dependent upon a number of factors including the solubility of the compound, rate of absorption in the gut, the extent of protein binding and metabolism etc. Various tests for bioavailability that would be familiar to a person of skill in the art are described herein (see also Trepanier et al, 1998, Gallant-Haidner et al, 2000).

As used herein the terms "impairment", "inhibition", "defect" used in relation to Complex I of the respiratory chain is intended to denote that a given drug substance have negative effect on Complex I or on mitochondrial metabolism upstream of Complex I, which could encompass any drug effect that limits the supply of NADH to Complex I, e.g. effects on Krebs cycle, glycolysis, beta-oxidation, pyruvate metabolism and even drugs that effect the transport or levels of glucose or other complex I-related substrates). As described herein, an excess of lactate in a subject is often an indication of a negative effect on aerobic respiration including Complex I.

As used herein the term "side-effect" used in relation to the function of Complex I of the respiratory chain may be a side-effect relating to lactic acidosis or it may be a side-effect relating to idiosyncratic drug organ toxicity e.g. hepatotoxicity, neurotoxicity, cardiotoxicity, renal toxicity and muscle toxicity encompassing, but not limited to, e.g. ophthalmoplegia, myopathy, sensorineural hearing impairment, seizures, stroke, stroke-like events, ataxia, ptosis, cognitive impairment, altered states of consciousness, neuropathic pain, polyneuropathy, neuropathic gastrointestinal problems (gastroesophageal reflux, constipation, bowel pseudo-obstruction), proximal renal tubular dysfunction, cardiac conduction defects (heart blocks), cardiomyopathy, hypoglycemia, gluconeogenic defects, nonalcoholic liver failure, optic neuropathy, visual loss, diabetes and exocrine pancreatic failure, fatigue, respiratory problems including intermittent air hunger.

As used herein the term "drug-induced" in relation to the term "side-effect" is to be understood in a broad sense. Thus, not only does it include drug substances, but also other substances that may lead to unwanted presence of lactate. Examples are herbicides, toxic mushrooms, berries etc.

The pharmaceutically acceptable salts of the compound of the invention include conventional salts formed from pharmaceutically acceptable inorganic or organic acids or bases as well as quaternary ammonium acid addition salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, fumaric, toluenesulfonic, methanesulfonic, naphthalene-2-sulfonic, benzenesulfonic hydroxynaphthoic, hydroiodic, malic, steroic, tannic and the like. Other acids such as oxalic, while not in themselves pharmaceutically acceptable, may be useful in the preparation of salts useful as intermediates in obtaining the compounds of the invention and their pharmaceutically acceptable salts. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts.

As used herein the term "alkyl" refers to any straight or branched chain composed of only sp3 carbon atoms, fully saturated with hydrogen atoms such as e.g. —$C_nH_{2n+1}$ for straight chain alkyls, wherein n can be in the range of 1 and 10 such as e.g. methyl, ethyl, propyl, isopropyl, n-butyl, isobutyl, sec-butyl, tert-butyl, n-pentyl, neopentyl, isopentyl, hexyl, isohexyl, heptyl, octyl, nonyl or decyl. The alkyl as used herein may be further substituted.

As used herein the term "cycloalkyl" refers to a cyclic/ring structured carbon chains having the general formula of —$C_nH_{2n-1}$ where n is between 3-10, such as e.g. cyclopropyl, cyclobytyl, cyclopentyl, cyclohexyl, cycloheptyl or cyclooctyl, bicycle[3.2.1]octyl, spiro[4,5]decyl, norpinyl, norbonyl, norcapryl, adamantly and the like.

As used herein, the term "alkene" refers to a straight or branched chain composed of carbon and hydrogen atoms wherein at least two carbon atoms are connected by a double bond such as e.g. $C_{2-10}$ alkenyl unsaturated hydrocarbon chain having from two to ten carbon atoms and at least one double bond. $C_{2-6}$ alkenyl groups include, but are not limited to, vinyl, 1-propenyl, allyl, iso-propenyl, n-butenyl, n-pentenyl, n-hexenyl and the like.

The term "$C_{1-10}$ alkoxy" in the present context designates a group —O—$C_{1-6}$ alkyl used alone or in combination, wherein $C_{1-10}$ alkyl is as defined above. Examples of linear alkoxy groups are methoxy, ethoxy, propoxy, butoxy, pentoxy and hexoxy. Examples of branched alkoxy are isopropoxy, sec-butoxy, tert-butoxy, iso-pentoxy and iso-hexoxy. Examples of cyclic alkoxy are cyclopropyloxy, cyclobutyloxy, cyclopentyloxy and cyclohexyloxy.

The term "$C_{3-7}$ heterocycloalkyl" as used herein denotes a radical of a totally saturated heterocycle like a cyclic hydrocarbon containing one or more heteroatoms selected from nitrogen, oxygen and sulphur independently in the cycle. Examples of heterocycles include, but are not limited to, pyrrolidine (1-pyrrolidine, 2-pyrrolidine, 3-pyrrolidine, 4-pyrrolidine, 5-pyrrolidine), pyrazolidine (1-pyrazolidine, 2-pyrazolidine, 3-pyrazolidine, 4-pyrazolidine, 5-pyrazolidine), imidazolidine (1-imidazolidine, 2-imidazolidine, 3-imidazolidine, 4-imidazolidine, 5-imidazolidine), thiazolidine (2-thiazolidine, 3-thiazolidine, 4-thiazolidine, 5-thiazolidine), piperidine (1-piperidine, 2-piperidine, 3-piperidine, 4-piperidine, 5-piperidine, 6-piperidine), piperazine (1-piperazine, 2-piperazine, 3-piperazine, 4-piperazine, 5-piperazine, 6-piperazine), morpholine (2-morpholine, 3-morpholine, 4-morpholine, 5-morpholine, 6-morpholine), thiomorpholine (2-thiomorpholine, 3-thiomorpholine, 4-thiomorpholine, 5-thiomorpholine, 6-thiomorpholine), 1,2-oxathiolane (3-(1,2-oxathiolane), 4-(1,2-oxathiolane), 5-(1,2-oxathiolane)), 1,3-dioxolane (2-(1,3-dioxolane), 3-(1,3-dioxolane), 4-(1,3-dioxolane)), tetrahydropyrane (2-tetrahydropyrane, 3-tetrahydropyrane, 4-tetrahydropyrane, 5-tetrahydropyrane, 6-tetrahydropyrane), hexahydropyradizine, (1-(hexahydropyradizine), 2-(hexahydropyradizine), 3-(hexahydropyradizine), 4-(hexahydropyradizine), 5-(hexahydropyradizine), 6-(hexahydropyradizine)).

The term "$C_{1-10}$alkyl-$C_{3-10}$cycloalkyl" as used herein refers to a cycloalkyl group as defined above attached through an alkyl group as defined above having the indicated number of carbon atoms.

The term "$C_{1-10}$ alkyl-$C_{3-7}$ heterocycloalkyl" as used herein refers to a heterocycloalkyl group as defined above attached through an alkyl group as defined above having the indicated number of carbon atoms. The term "aryl" as used herein is intended to include carbocyclic aromatic ring systems.

Aryl is also intended to include the partially hydrogenated derivatives of the carbocyclic systems enumerated below.

The term "heteroaryl" as used herein includes heterocyclic unsaturated ring systems containing one or more heteroatoms selected among nitrogen, oxygen and sulphur, such as furyl, thienyl, pyrrolyl, and is also intended to include the partially hydrogenated derivatives of the heterocyclic systems enumerated below.

The terms "aryl" and "heteroaryl" as used herein refers to an aryl, which can be optionally unsubstituted or mono-, di- or tri substituted, or a heteroaryl, which can be optionally unsubstituted or mono-, di- or tri substituted. Examples of "aryl" and "heteroaryl" include, but are not limited to, phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), phenanthrenyl, fluorenyl, pentalenyl, azulenyl, biphenylenyl, thiophenyl (1-thienyl, 2-thienyl), furyl (1-furyl, 2-furyl), furanyl, thiophenyl, isoxazolyl, isothiazolyl, 1,2,3-triazolyl, 1,2,4-triazolyl, pyranyl, pyridazinyl, pyrazinyl, 1,2,3-triazinyl, 1,2,4-triazinyl, 1,3,5-triazinyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, tetrazolyl, thiadiazinyl, indolyl, isoindolyl, benzofuranyl, benzothiophenyl (thianaphthenyl), indolyl, oxadiazolyl, isoxazolyl, quinazolinyl, fluorenyl, xanthenyl, isoindanyl, benzhydryl, acridinyl, benzisoxazolyl, purinyl, quinazolinyl, quinolizinyl, quinolinyl, isoquinolinyl, quinoxalinyl, naphthyridinyl, phteridinyl, azepinyl, diazepinyl, pyrrolyl (2-pyrrolyl), pyrazolyl (3-pyrazolyl), 5-thiophene-2-yl-2H-pyrazol-3-yl, imidazolyl (1-imidazolyl, 2-imidazolyl, 4-imidazolyl, 5-imidazolyl), triazolyl (1,2,3-triazol-1-yl, 1,2,3-triazol-2-yl, 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), isoquinolyl (1-isoquinolyl, 3-isoquinolyl, 4-isoquinolyl, 5-isoquinolyl, 6-isoquinolyl, 7-isoquinolyl, 8-isoquinolyl), quinolyl (2-quinolyl, 3-quinolyl, 4-quinolyl, 5-quinolyl, 6-quinolyl, 7-quinolyl, 8-quinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl)), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl)), indolyl (1-indolyl, 2-indolyl, 3-indolyl, 4-indolyl, 5-indolyl, 6-indolyl, 7-indolyl), indazolyl (1-indazolyl, 2-indazolyl, 3-indazolyl, 4-indazolyl, 5-indazolyl, 6-indazolyl, 7-indazolyl), benzimidazolyl, (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl). Non-limiting examples of partially hydrogenated derivatives are 1,2,3,4-tetrahydronaphthyl, 1,4-dihydronaphthyl, pyrrolinyl, pyrazolinyl, indolinyl, oxazolidinyl, oxazolinyl, oxazepinyl and the like.

As used herein the term "acyl" refers to a carbonyl group —C(=O) R wherein the R group is any of the above defined groups. Specific examples are formyl, acetyl, propionyl, butyryl, pentanoyl, hexanoyl, heptanoyl, octanoyl, nonanoyl, decanoyl, benzoyl and the likes.

"Optionally substituted" as applied to any group means that the said group may, if desired, be substituted with one or more substituents, which may be the same or different. 'Optionally substituted alkyl' includes both 'alkyl' and 'substituted alkyl'.

Examples of suitable substituents for "substituted" and "optionally substituted" moieties include halo (fluoro, chloro, bromo or iodo), $C_{1-6}$ alkyl, $C_{3-6}$ cycloalkyl, hydroxy, $C_{1-6}$ alkoxy, cyano, amino, nitro, $C_{1-6}$ alkylamino, $C_{2-6}$ alkenylamino, di-$C_{1-6}$ alkylamino, $C_{1-6}$ acylamino, di-$C_{1-6}$ acylamino, $C_{1-6}$ aryl, $C_{1-6}$ arylamino, $C_{1-6}$ aroylamino, benzylamino, $C_{1-6}$ arylamido, carboxy, $C_{1-6}$ alkoxycarbonyl or ($C_{1-6}$ aryl)($C_{1-10}$ alkoxy)carbonyl, carbamoyl, mono-$C_{1-6}$ carbamoyl, di-$C_{1-6}$ carbamoyl or any of the above in which a hydrocarbyl moiety is itself substituted by halo, cyano, hydroxy, $C_{1-2}$ alkoxy, amino, nitro, carbamoyl, carboxy or $C_{1-2}$ alkoxycarbonyl. In groups containing an oxygen atom such as hydroxy and alkoxy, the oxygen atom can be replaced with sulphur to make groups such as thio (SH) and thio-alkyl (S-alkyl). Optional substituents therefore include groups such as S-methyl. In thio-alkyl groups, the sulphur atom may be further oxidised to make a sulfoxide or sulfone, and thus optional substituents therefore includes groups such as S(O)-alkyl and S(O)$_2$-alkyl.

Substitution may take the form of double bonds, and may include heteroatoms. Thus an alkyl group with a carbonyl (C=O) instead of a CH$_2$ can be considered a substituted alkyl group.

Substituted groups thus include for example CFH$_2$, CF$_2$H, CF$_3$, CH$_2$NH$_2$, CH$_2$OH, CH$_2$CN, CH$_2$SCH$_3$, CH$_2$OCH$_3$, OMe, OEt, Me, Et, —OCH$_2$O—, CO$_2$Me, C(O)Me, i-Pr, SCF$_3$, SO$_2$Me, NMe$_2$, CONH$_2$, CONMe$_2$ etc. In the case of aryl groups, the substitutions may be in the form of rings from adjacent carbon atoms in the aryl ring, for example cyclic acetals such as O—CH$_2$—O.

The invention is illustrated in the following figures:

FIG. 1. Schematic figure of evaluation assay for enhancement of mitochondrial energy producing function in complex I inhibited cells. Protocol for evaluating the compounds according to the invention. In the assay, mitochondrial function in intact cells is repressed with the respiratory complex I inhibitor rotenone. Drug candidates are compared with endogenous (non cell-permeable) substrates before and after permeabilization of the plasma membrane to evaluate bioenergetic enhancement or inhibition.

Figure 2:
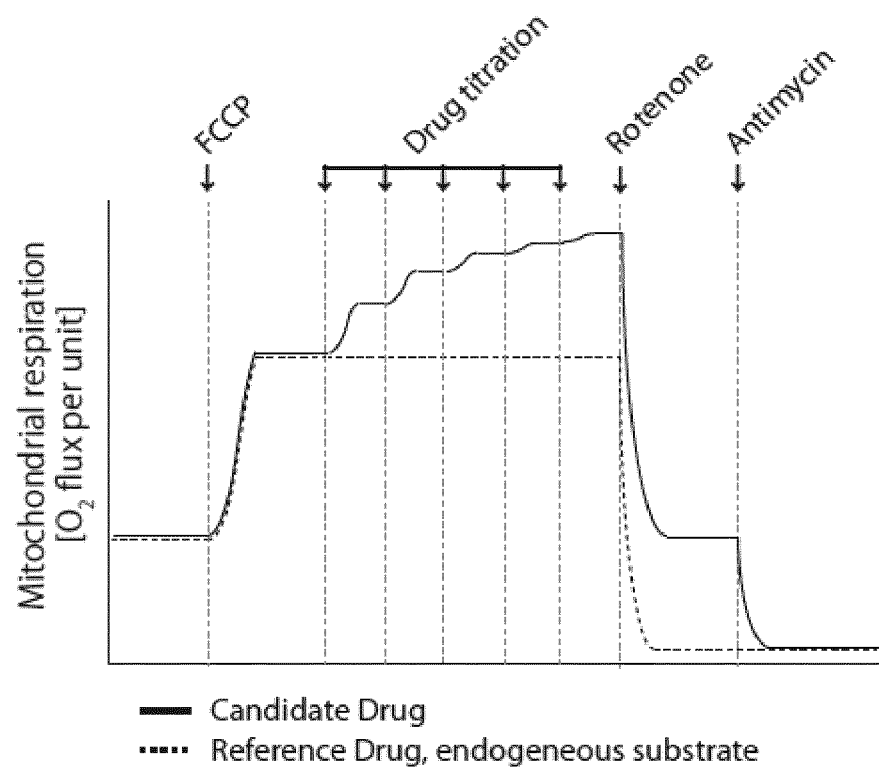

FIG. 2. Schematic figure of assay for enhancement and inhibition of mitochondrial energy producing function in intact cells. Protocol for evaluating the potency of compounds according to the invention. In the assay, mitochondrial activity is stimulated by uncoupling the mitochondria with the protonophore FCCP. Drug candidates are titrated to obtain the level of maximum convergent (complex I- and complex II-derived) respiration. After rotenone addition, complex II-dependent stimulation is obtained. The complex III-inhibitor Antimycin is added to evaluate non mitochondrial oxygen consumption.

Figure 3:
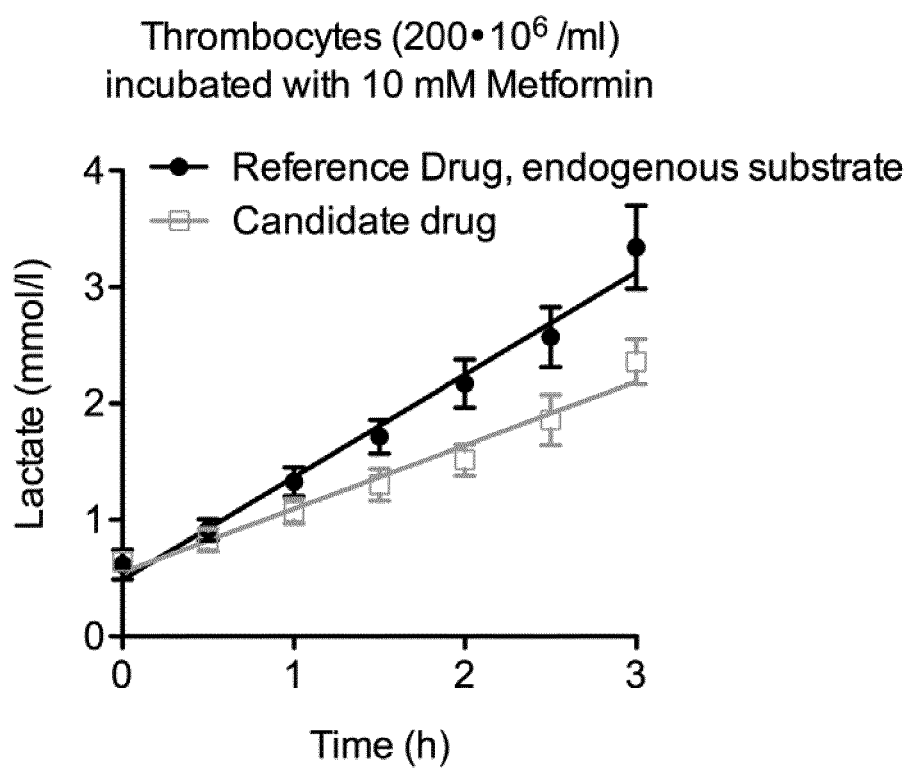

FIG. 3. Schematic figure of assay for prevention of lactate accumulation in cells exposed to a mitochondrial complex I inhibitor. Protocol for evaluating the potency of compounds according to the invention. In the assay, mitochondrial function in intact cells is repressed with the respiratory complex I inhibitor rotenone. As the cells shift to glycolysis lactate is accumulated in the medium. Drug candidates are compared with endogenous (non cell-permeable) substrates and decreased rate of lactate accumulation indicates restoration of mitochondrial ATP production.

Figure 4:
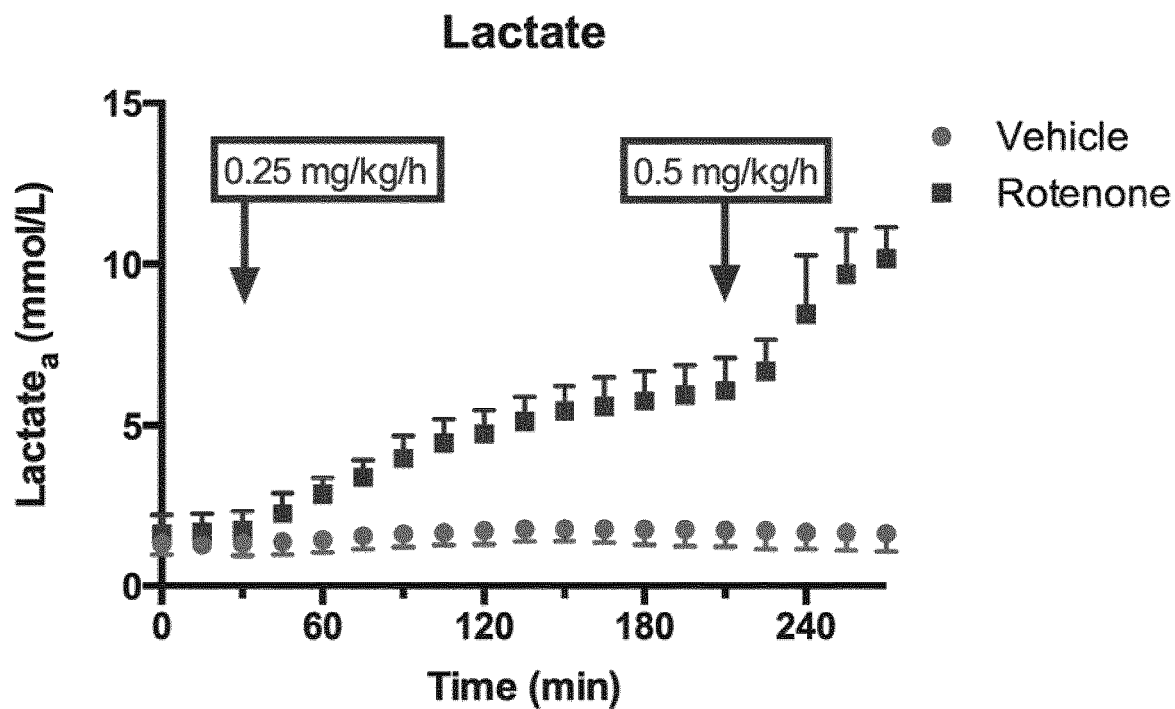

FIG. 4. Figure of lactate accumulation in an acute metabolic crisis model in pig.

Lactate accumulation in an acute metabolic crisis model in pig. In the animal model, mitochondrial function is repressed by infusion of the respiratory complex I inhibitor rotenone. As the cells shift to glycolysis lactate is accumulated in the body. Mean arterial lactate concentrations are demonstrated for rotenone and vehicle treated animals at indicated infusion rates. Drug candidates are evaluated in rotenone treated animals and decreased rate of lactate accumulation indicates restoration of mitochondrial ATP production.

Figure 5:
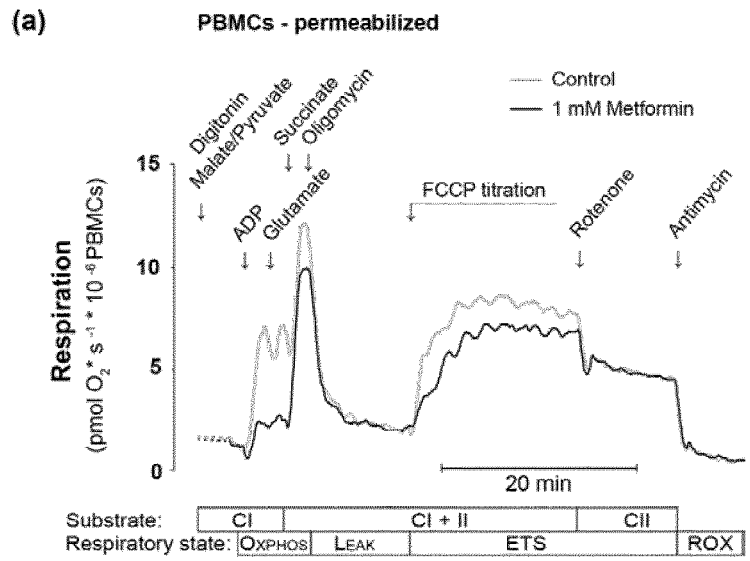
Figure 5:
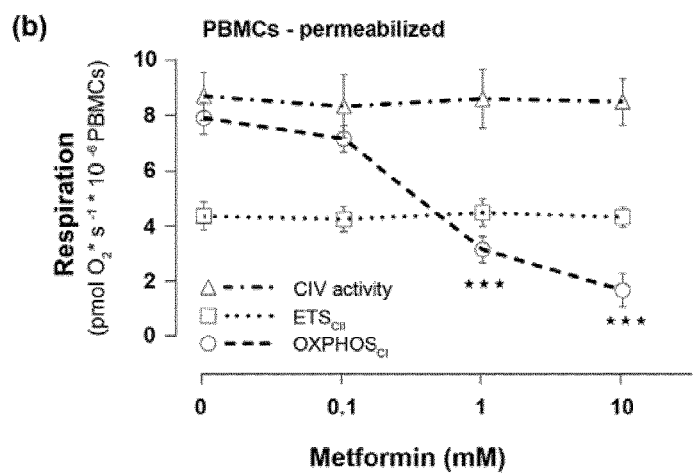
Figure 5:
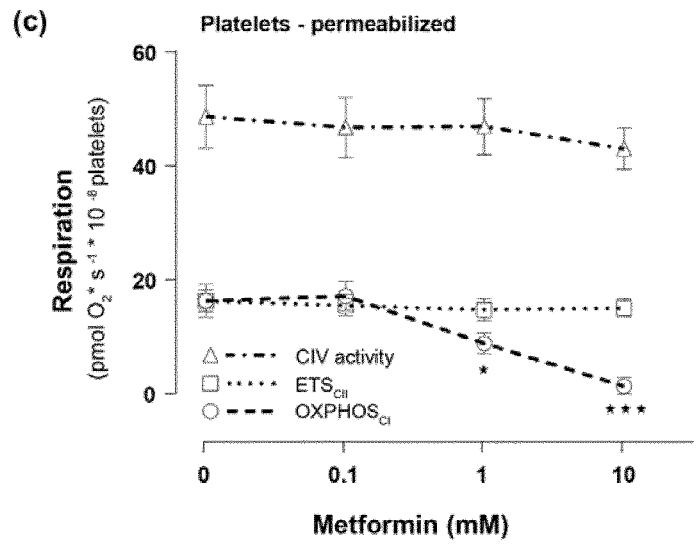

FIG. 5 Effect of metformin on mitochondrial respiration in permeabilized human peripheral blood mononuclear cells (PBMCs) and platelets. (a) Representative traces of simultaneously measured $O_2$ consumption of metformin-(1 mM, black trace) or vehicle-treated ($H_2O$, grey trace) permeabilized PBMCs assessed by applying sequential additions of indicated respiratory complex-specific substrates and inhibitors. The stabilization phase of the traces, disturbances due to reoxygenation of the chamber and complex IV substrate administration have been omitted (dashed lines). Boxes below traces state the respiratory complexes utilized for respiration during oxidation of the given substrates, complex I (CI), complex II (CII) or both (CI+II), as well as the respiratory states at the indicated parts of the protocol. Respiratory rates at three different respiratory states and substrate combinations are illustrated for PBMCs (b) and platelets (c) for control ($H_2O$) and indicated concentrations of metformin: oxidative phosphorylation capacity supported by complex I substrates ($OXPHOS_{CI}$), complex II-dependent maximal flux through the electron transport system ($ETS_{CII}$) following titration of the protonophore FCCP, and complex IV (CIV) capacity. Values are depicted as mean±SEM. *=P<0.05, =P<0.01 and *=P<0.001 using one-way ANOVA with Holm-Sidak's multiple comparison method, n=5. OXPHOS=oxidative phosphorylatation. ETS=electron transport system. ROX=residual oxygen concentration.

Figure 6:
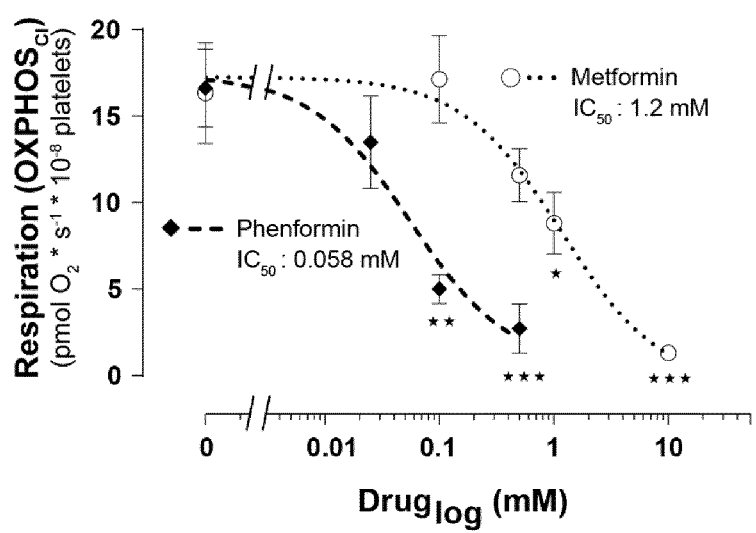

FIG. 6 Dose-response comparison of the toxicity displayed by metformin and phenformin on mitochondrial respiratory capacity during oxidative phosphorylation supported by complex I-linked substrates ($OXPHOS_{CI}$) in permeabilized human platelets. Rates of respiration are presented as mean±SEM and standard non-linear curve fitting was applied to obtain half maximal inhibitory concentration ($IC_{50}$) values for metformin and phenformin. *=P<0.05, =P<0.01 and *=P<0.001 compared to control using one-way ANOVA with Holm-Sidak's multiple comparison method, n=5.

Figure 7:
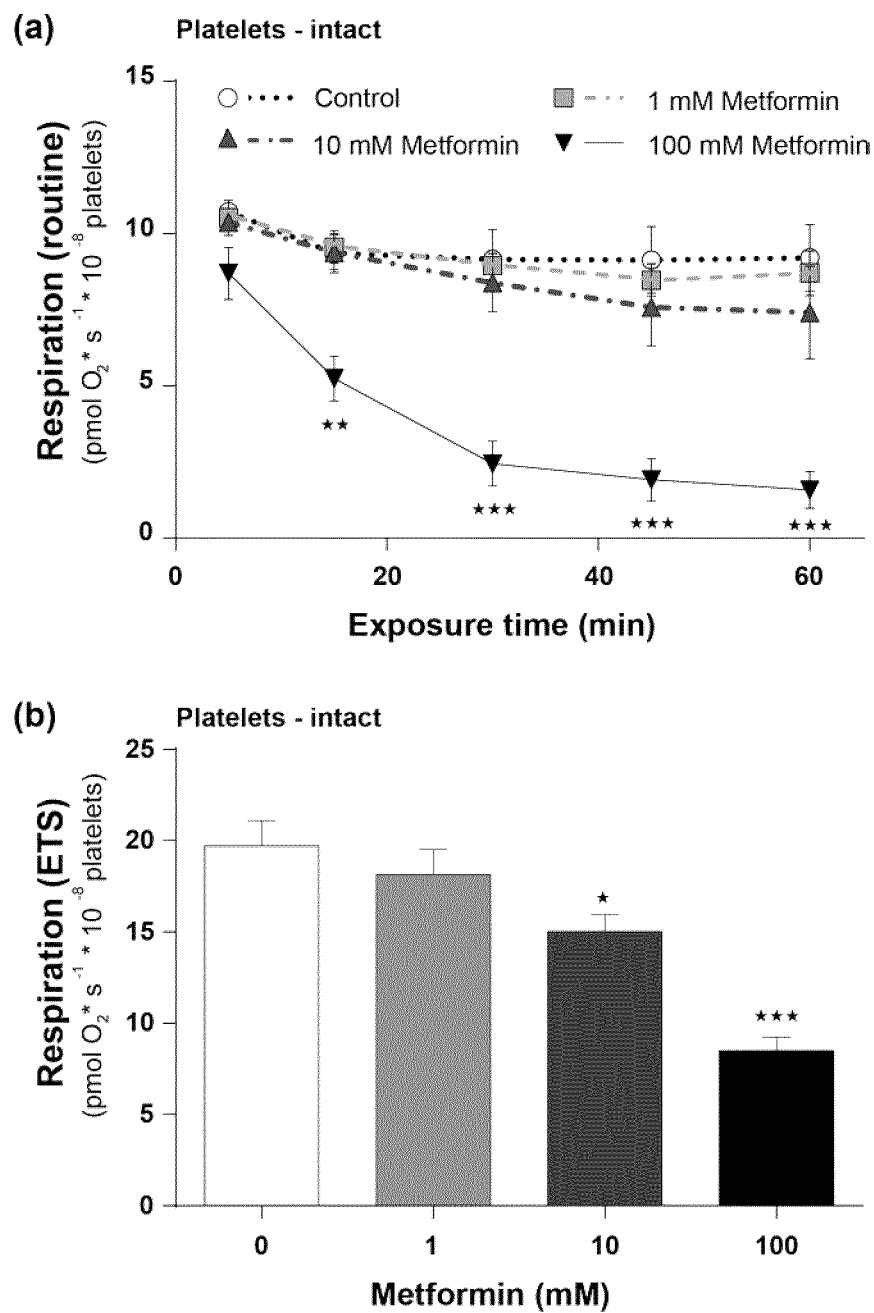

FIG. 7 Time- and dose-dependent effects of metformin on mitochondrial respiration in intact human platelets. (a) Routine respiration of platelets, i.e. respiration of the cells with their endogenous substrate supply and ATP demand, was monitored during 60 min incubation of indicated concentrations of metformin or vehicle ($H_2O$), which was followed by (b) maximal respiratory capacity induced by titration of the protonophore FCCP to determine maximal flux through the electron transport system (ETS) of the intact cells. Data are expressed as mean±SEM, n=5. *=P<0.05, =P<0.01 and *=P<0.001 using one-way ANOVA (b) and two-way ANOVA (a) with Holm-Sidak's post-hoc test.

Figure 8:
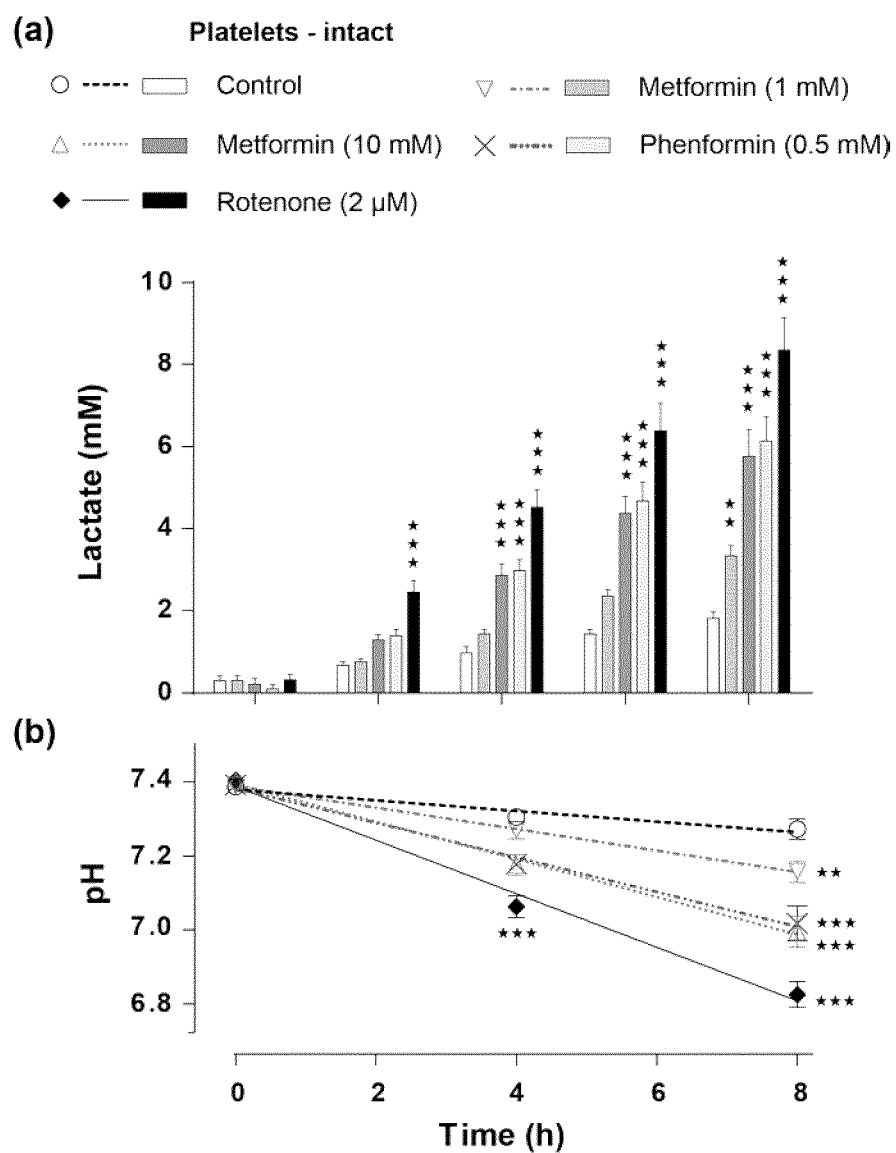

FIG. 8 Effect of metformin and phenformin on lactate production and pH in suspensions of intact human platelets. Platelets were incubated in phosphate buffered saline containing glucose (10 mM) for 8 h with either metformin (10 mM, 1 mM), phenformin (0.5 mM), the complex I inhibitor rotenone (2 μM), or vehicle (DMSO, control). (a) Lactate levels were determined every 2 h (n=5), and (b) pH was measured every 4 h (n=4). Data are expressed as mean±SEM. *=P<0.05, =P<0.01 and *=P<0.001 using two-way ANOVA with Holm-Sidak's post-hoc test.

Figure 9:
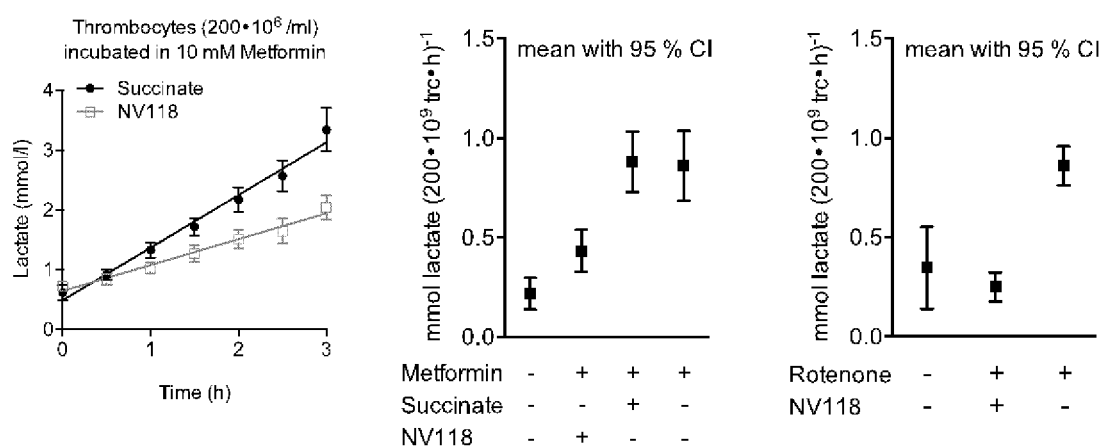

FIG. 9 Human intact thrombocytes ($200 \cdot 10^6$/ml) incubated in PBS containing 10 mM glucose. (A) Cells incubated with 10 mM metformin were treated with either succinate or NV118 in consecutive additions of 250 μM each 30 minutes. Prior to addition of NV118 at time 0 h, cells have been incubated with just metformin or vehicle for 1 h to establish equal initial lactate levels (data not shown). Lactate concentrations were sampled each 30 minutes. (B) Lactate production was calculated with a non-linear fit regression and 95% confidence intervals for the time lactate curves were calculated. Cells incubated with metformin had a significantly higher production of lactate than control, and succinate additions did not change this. Lactate production was significantly decreased when NV118 was added to the cells incubated with metformin. (C) Lactate production induced by rotenone could similarly be attenuated by repeated additions of NV118.

Figure 10:
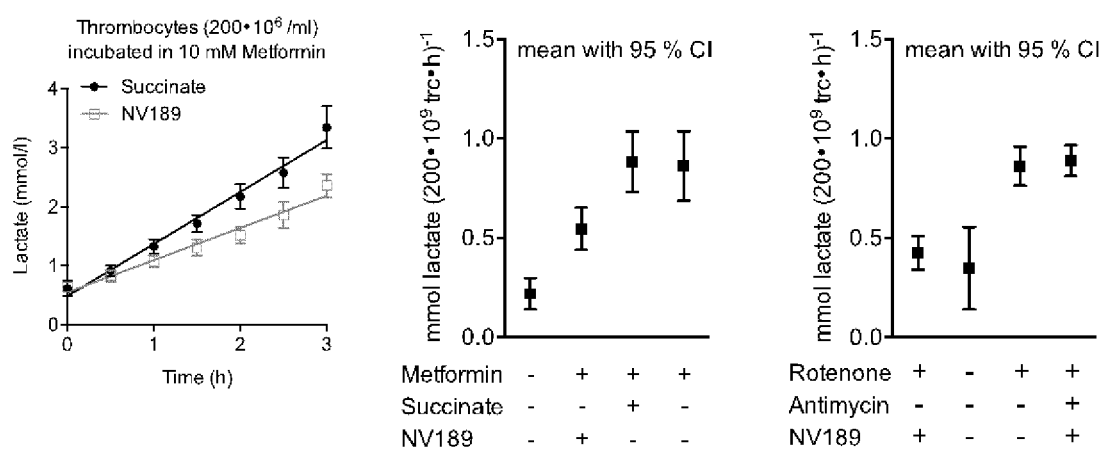

FIG. 10 Human intact thrombocytes ($200 \cdot 10^6$/ml) incubated in PBS containing 10 mM glucose. (A) Cells incubated with 10 mM metformin were treated with either succinate or NV189 in consecutive additions of 250 μM each 30 minutes. Prior to addition of NV189 at time 0 h, cells have been incubated with just metformin or vehicle for 1 h to establish equal initial lactate levels (data not shown). Lactate concentrations were sampled each 30 minutes. (B) Lactate production was calculated with a non-linear fit regression and 95% confidence intervals for the time lactate curves were calculated. Cells incubated with metformin had a significantly higher production of lactate than control, and succinate additions did not change this. Lactate production was significantly decreased when NV189 was added to the cells incubated with metformin. (C) Lactate production induced by rotenone could similarly be attenuated by repeated additions of NV189. When antimycin also was added, the effect of NV189 on complex 2 was abolished by antimycin's inhibitory effect on complex III.

Figure 11:
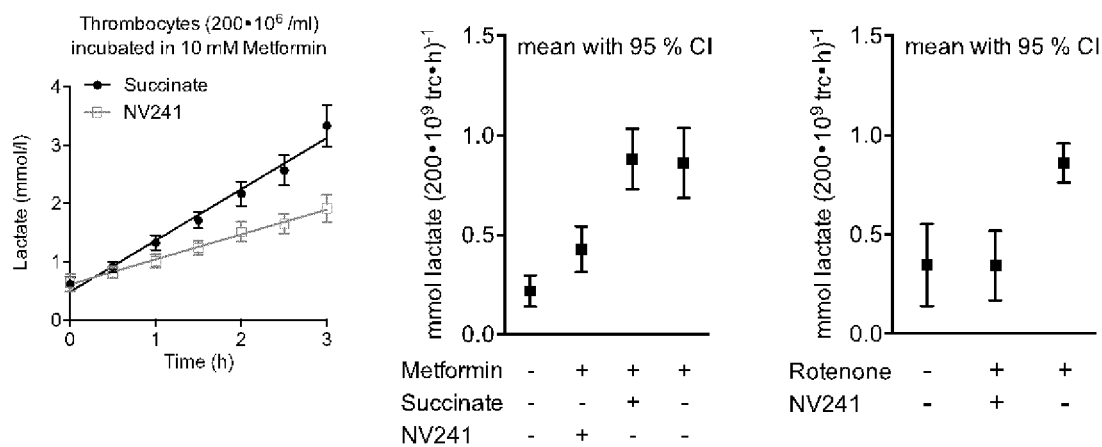

FIG. 11 Human intact thrombocytes ($200 \cdot 10^6$/ml) incubated in PBS containing 10 mM glucose. (A) Cells incubated with 10 mM metformin were treated with either succinate or NV241 in consecutive additions of 250 μM each 30 minutes. Prior to addition of NV241 at time 0 h, cells have been incubated with just metformin or vehicle for 1 h to establish equal initial lactate levels (data not shown). Lactate concentrations were sampled each 30 minutes. (B) Lactate production was calculated with a non-linear fit regression and 95% confidence intervals for the time lactate curves were calculated. Cells incubated with metformin had a significantly higher production of lactate than control, and succinate additions did not change this. Lactate production was significantly decreased when NV241 was added to the cells incubated with metformin. (C) Lactate production induced by rotenone could similarly be attenuated by repeated additions of NV241.

Figure 12:
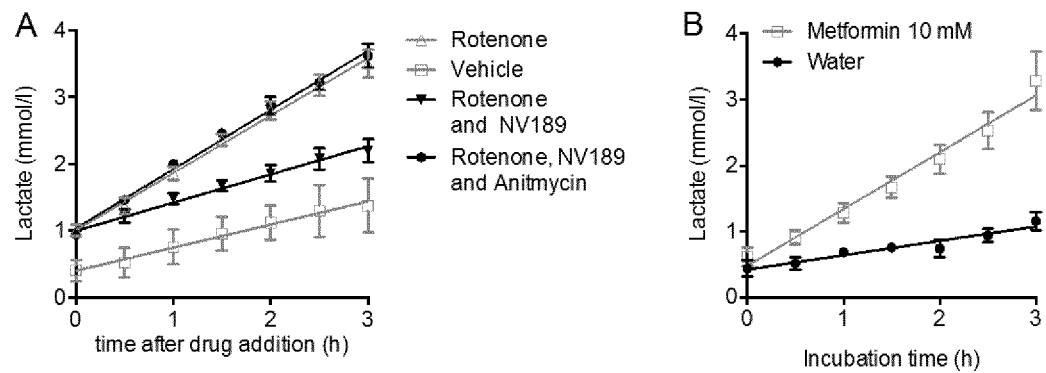

FIG. 12 Thrombocytes ($200 \cdot 10^6$/ml) incubated in PBS containing 10 mM of glucose with sampling of lactate concentrations every 30 minutes. (A) During 3 hour incubation, cells treated with either rotenone (2 μM) or its vehicle is monitored for change in lactate concentration in media over time. Also, cells were incubated with rotenone together with NV189 and cells with rotenone, NV189 and the complex III inhibitor antimycin (1 μg/mL) are monitored. Prior to addition of NV189 at time 0 h, cells have been incubated with just rotenone or vehicle for 1 h to establish equal initial lactate levels (data not shown). Rotenone increase the lactate production of the cells, but this is brought back to normal (same curve slope) by co-incubation with NV189 (in consecutive additions of 250 μM each 30 minutes). When antimycin also is present, NV189 cannot function at complex II level, and lactate production is again increased to the same level as with only rotenone present. (B) A similar rate of lactate production as with rotenone can be induced by incubation with Metformin at 10 mM concentration.

EXPERIMENTAL

General Biology Methods

A person of skill in the art will be able to determine the pharmacokinetics and bioavailability of the compound of the invention using in vivo and in vitro methods known to a person of skill in the art, including but not limited to those described below and in Gallant-Haidner et al, 2000 and Trepanier et al, 1998 and references therein. The bioavailability of a compound is determined by a number of factors, (e.g. water solubility, cell membrane permeability, the extent of protein binding and metabolism and stability) each of which may be determined by in vitro tests as described in the examples herein, it will be appreciated by a person of skill in the art that an improvement in one or more of these factors will lead to an improvement in the bioavailability of a compound. Alternatively, the bioavailability of the compound of the invention may be measured using in vivo methods as described in more detail below, or in the examples herein.

In order to measure bioavailability in vivo, a compound may be administered to a test animal (e.g. mouse or rat) both intraperitoneally (i.p.) or intravenously (i.v.) and orally (p.o.) and blood samples are taken at regular intervals to examine how the plasma concentration of the drug varies over time. The time course of plasma concentration over time can be used to calculate the absolute bioavailability of the compound as a percentage using standard models. An example of a typical protocol is described below.

For example, mice or rats are dosed with 1 or 3 mg/kg of the compound of the invention i.v. or 1, 5 or 10 mg/kg of the compound of the invention p.o. Blood samples are taken at 5 min, 15 min, 1 h, 4 h and 24 h intervals, and the concentration of the compound of the invention in the sample is determined via LCMS-MS. The time-course of plasma or whole blood concentrations can then be used to derive key parameters such as the area under the plasma or blood concentration-time curve (AUC—which is directly proportional to the total amount of unchanged drug that reaches the systemic circulation), the maximum (peak) plasma or blood drug concentration, the time at which maximum plasma or blood drug concentration occurs (peak time), additional factors which are used in the accurate determination of bioavailability include: the compound's terminal half-life, total body clearance, steady-state volume of distribution and F %. These parameters are then analysed by non-compartmental or compartmental methods to give a calculated percentage bioavailability, for an example of this type of method see Gallant-Haidner et al, 2000 and Trepanier et al, 1998, and references therein.

The efficacy of the compound of the invention may be tested using one or more of the methods described below:

I. Assays for Evaluating Enhancement and Inhibition of Mitochondrial Energy Producing Function in Intact Cells High Resolution Respirometry—A-General Method Measurement of mitochondrial respiration is performed in a high-resolution oxygraph (Oxygraph-2 k, Oroboros Instruments, Innsbruck, Austria) at a constant temperature of 37° C. Isolated human platelets, white blood cells, fibroblasts, human heart muscle fibers or other cell types containing live mitochondria are suspended in a 2 mL glass chamber at a concentration sufficient to yield oxygen consumption in the medium of $\geq$pmol $O_2$ $s^{-1}$ $mL^1$.

High-Resolution Respirometry—B (Used in Lactate Studies)

Real-time respirometric measurements were performed using high-resolution oxygraphs (Oxygraph-2 k, Oroboros Instruments, Innsbruck, Austria). The experimental conditions during the measurements were the following: 37° C., 2 mL active chamber volume and 750 rpm stirrer speed. Chamber concentrations of $O_2$ were kept between 200-50 µM with reoxygenation of the chamber during the experiments as appropriate (Sjövall et al. 2013a). For data recording, DatLab software version 4 and 5 were used (Oroboros Instruments, Innsbruck, Austria). Settings, daily calibration and instrumental background corrections were conducted according to the manufacturer's instructions. Respiratory measurements were performed in either a buffer containing 0.5 mM EGTA, 3 mM $MgCl_2$, 60 mM K-lactobionate, 20 mM Taurine, 10 mM $KH_2PO_4$, 20 mM HEPES, 110 mM sucrose and 1 g/L bovine serum albumin (MiR05) or phosphate buffered saline (PBS) with glucose (5 mM) and EGTA (5 mM), as indicated in the corresponding sections. Respiratory values were corrected for the oxygen solubility factor both media (0.92) (Pesta and Gnaier, 2012). Lactate production of intact human platelets was determined in PBS containing 10 mM glucose. All measurements were performed at a platelet concentration of $200\times10^6$ cells per mL or a PBMC concentration of $5\times10^6$ cells per mL.

Evaluation of Compounds

Four typical evaluation protocols in intact cells are utilized.

(1) Assay for Enhancement of Mitochondrial Energy Producing Function in Cells with Inhibited Respiratory Complex I Cells are placed in a buffer containing 110 mM sucrose, HEPES 20 mM, taurine 20 mM, K-lactobionate 60 mM, $MgCl_2$ 3 mM, $KH_2PO_4$ 10 mM, EGTA 0.5 mM, BSA 1 g/l, pH 7.1. After baseline respiration with endogenous substrates is established, complex I is inhibited with Rotenone 2 µM. Compounds dissolved in DMSO are titrated in a range of 10 µM to 10 mM final concentration. Subsequently, cell membranes are permeabilised with digitonin (1 mg/1*$10^6$ pit) to allow entry of extracellularly released energy substrate or cell impermeable energy substrates. After stabilized respiration, Succinate 10 mM is added as a reference to enable respiration downstream of complex I. After the respiration stabilized the experiment is terminated by addition of Antimycin at final concentration 1 µg/mL and any residual non-mitochondrial oxygen consumption is measured. An increase in respiration rate in the described protocol is tightly coupled to ATP synthesis by oxidative phosphorylation unless cells are uncoupled (i.e. proton leak without production of ATP). Uncoupling is tested for by addition of the ATP synthase inhibitor oligomycin (1-2 µg $mL^{-1}$) in a protocol 3 where the extent of uncoupling corresponds to the respiratory rate following oligomycin addition.

(2) Assay for Enhancement and Inhibition of Mitochondrial Energy Producing Function in Intact Cells In the second protocol the same buffer is used as described above. After basal respiration is established, the mitochondrial uncoupler FCCP is added at a concentration of 2 nM to increase metabolic demand. Compounds dissolved in DMSO are titrated in several steps from 10 µM to 10 mM final concentration in order to evaluate concentration range of enhancement and/or inhibition of respiration. The experiment is terminated by addition of 2 µM Rotenone to inhibit complex I, revealing remaining substrate utilization downstream of this respiratory complex, and 1 μg/mL of the complex III inhibitor Antimycin to measure non-mitochondrial oxygen consumption.

(3) Assay to Assess Uncoupling in Intact Cells

In the third protocol, the same buffer as described above is used. After basal respiration is established, 1 mM of compound dissolved in DMSO is added. Subsequently, the ATP-synthase-inhibitor Oligomycin is added. A reduction in respiration is a measure of how much of the oxygen consumption that is coupled to ATP synthesis. No, or only a slight, reduction indicate that the compound is inducing a proton leak over the inner mitochondrial membrane. The uncoupler FCCP is then titrated to induce maximum uncoupled respiration. Rotenone (2 μM) is then added to inhibit complex I, revealing remaining substrate utilization downstream of this respiratory complex. The experiment is terminated by the addition of 1 μg/mL of the complex III inhibitor Antimycin to measure non-mitochondrial oxygen consumption.

(4) Assay for Enhancement of Mitochondrial Energy Producing Function in Cells with Inhibited Respiratory Complex I in Human Plasma Intact human blood cells are incubated in plasma from the same donor. After baseline respiration with endogenous substrates is established, complex I is inhibited with Rotenone 2 μM. Compounds dissolved in DMSO are titrated in a range of 10 μM to 10 mM final concentration. The experiment is terminated by addition of Antimycin at final concentration 1 μg/mL and any residual non-mitochondrial oxygen consumption is measured.

Properties of Desired Compound in Respiration Assays

The ideal compound stimulates respiration in the described protocols in intact cells at low concentration without inhibitory effect on either succinate stimulated respiration after permeabilization in protocol 1 or the endogenous respiration in protocol 2. The concentration span between maximal stimulatory effect and inhibition should be as wide as possible. After inhibition of respiration with mitochondrial toxins at or downstream of complex III, respiration should be halted. Please refer to FIG. 1 and the listing below.

Desired properties of compounds:
maximum value of a reached at low drug concentration.
a substantially more than a'
a approaches b'
c approaches c'
d approaches d'
Compounds impermeable to the cellular membrane are identified in the assay as:
a approaches a'
Non mitochondrial oxygen consumption induced by drug candidate is identified when
d more than d'

II. Assay for Prevention of Lactate Accumulation in Cells Exposed to a Mitochondrial Complex I Inhibitor Intact human platelets, white blood cells, fibroblasts, or other cell types containing live mitochondria are incubated in phosphate buffered saline containing 10 mM glucose for 8 h with either of the complex I inhibiting drugs metformin (10 mM), phenformin (0.5 mM) or rotenone (2 μM). The inhibition of mitochondrial ATP production through oxidative phosphorylation by these compounds increases lactate accumulation by glycolysis. Lactate levels are determined every 2 h (or more frequent eg every 30 min) using the Lactate Pro™ 2 blood lactate test meter (Arkray, Alere AB, Lidingö, Sweden) or similar types of measurements. Incubation is performed at 37° C. pH is measured at start, after 4 and after 8 h (or more frequently) of incubation using a Standard pH Meter, e.g. PHM210 (Radiometer, Copenhagen, Denmark). Drug candidates are added to the assay from start or following 30-60 min at concentrations within the range 10 μM-5 mM. The prevention of lactate accumulation is compared to parallel experiments with compound vehicle only, typically DMSO. In order to evaluate the specificity of the drug candidate, it is also tested in combination with a down-stream inhibitor of respiration such as the complex III inhibitor Antimycin at 1 μg/mL, which should abolish the effect of the drug candidate and restore the production of lactate. The use of antimycin is therefore also a control for undue effects of drug candidates on the lactate producing ability of the cells used in the assay. (See e.g. FIGS. 9, 10 and 11).

Data Analysis

Statistical analysis was performed using Graph Pad PRISM software (GraphPad Software version 6.03, La Jolla, Calif., USA). All respiratory, lactate and pH data are expressed as mean±SEM. Ratios are plotted as individuals and means. One-way ANOVA was used for one-factor comparison of three or more groups (concentration of drugs) and two-way mixed model ANOVA was used for two-factor comparison (time and concentration of drugs/treatment) of three or more groups. Post-hoc tests to compensate for multiple comparisons were done according to Holm-Sidak. Correlations were expressed as $r^2$ and P-values. Standard non-linear curve fitting was applied to calculate half maximal inhibitory concentration ($IC_{50}$) values. Results were considered statistically significant for $P<0.05$.

Properties of Desired Compound in Cellular Lactate Accumulation Assay (1) The ideal compound prevents the lactate accumulation induced by complex I inhibition, i.e. the lactate accumulation approaches a similar rate as that in non complex I-inhibited cells. (2) The prevention of lactate accumulation is abolished by a down-stream respiratory inhibitor such as Antimycin.

III. Assay for Prevention of Lactate Accumulation and Energetic Inhibition in an Acute Metabolic Crisis Model in Pig Lead drug candidates will be tested in a proof of concept in vivo model of metabolic crisis due to mitochondrial dysfunction at complex I. The model mimics severe conditions that can arise in children with genetic mutations in mitochondrial complex I or patients treated and overdosed with clinically used medications such as metformin, which inhibits complex I when accumulated in cells and tissues.

Female landrace pigs are used in the study. They are anaesthetized, taken to surgery in which catheters are placed for infusions and monitoring activities. A metabolic crisis is induced by infusion of the mitochondrial complex I inhibitor rotenone at a rate of 0.25 mg/kg/h during 3 h followed by 0.5 mg/kg/h infused during one hour (vehicle consisting of 25% NMP/4% polysorbate 80/71% water). Cardiovascular parameters such as arterial blood pressure is measured continuously through a catheter placed in the femoral artery. Cardiac output (CO) is measured and recorded every 15 minutes by thermo-dilution, and pulmonary artery pressure (PA, systolic and diastolic), central venous pressure (CVP), and $SvO_2$ is recorded every 15 min and pulmonary wedge pressure (PCWP) every 30 min from a Swan-Ganz catheter. Indirect calorimetry is performed e.g. by means of a Quark RMR ICU option (Cosmed, Rome, Italy) equipment. Blood gases and electrolytes are determined in both arterial and venous blood collected from the femoral artery and Swan-Ganz catheters and analysed with use of an ABL725 blood gas analyser (Radiometer Medical Aps, Brønshøj, Denmark). Analyses include pH, BE, Hemoglobin, HCO$_3$, pO$_2$, pCO$_2$, K$^+$, Na$^+$, Glucose and Lactate.

Properties of Desired Compound in a Proof of Concept In Vivo Model of Metabolic Crisis The ideal compound should reduce the lactate accumulation and pH decrease in pigs with metabolic crisis induced by complex I inhibition. The energy expenditure decrease following complex I inhibition should be attenuated. The compound should not induce any overt negative effects as measured by blood and hemodynamic analyses.

Metabolomics Method

White blood cells or platelets are collected by standard methods and suspended in a MiR05, a buffer containing 110 mM sucrose, HEPES 20 mM, taurine 20 mM, K-lactobionate 60 mM, MgCl$_2$ 3 mM, KH$_2$PO$_4$ 10 mM, EGTA 0.5 mM, BSA 1 g/l, with or with our 5 mM glucose, pH 7.1. The sample is incubated with stirring in a high-resolution oxygraph (Oxygraph-2 k, Oroboros Instruments, Innsbruck, Austria) at a constant temperature of 37° C.

After 10 minutes rotenone in DMSO is added (2 µM) and incubation continued. Following a further 5 minutes test compound in DMSO is added, optionally with further test compound after and a further period of incubation. During the incubation O$_2$ consumption is measured in real-time.

At the end of the incubation the cells are collected by centrifugation and washed in 5% mannitol solution and extracted into methanol. An aqueous solution containing internal standard is added and the resultant solution treated by centrifugation in a suitable microfuge tube with a filter.

The resulting filtrate is dried under vacuum before CE-MS analysis to quantify various primary metabolites by the method of Ooga et al (2011) and Ohashi et al (2008).

In particular the levels of metabolite in the TCA cycle and glycolysis are assessed for the impact of compounds of the invention.

Ooga et al, Metabolomic anatomy of an animal model revealing homeostatic imbalances in dyslipidaemia, Molecular Biosystems, 2011, 7, 1217-1223

Ohashi et al, Molecular Biosystems, 2008, 4, 135-147

Materials

Unless otherwise indicated, all reagents used in the examples below are obtained from commercial sources.

Examples

Example 1

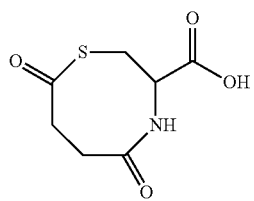

Succinyl chloride (0.1 mol) and triethylamine (0.4 mol) is dissolved in DCM and cysteine is added. The reaction is stirred at room temperature. The reaction is added to aqueous dilute hydrochloric acid and then is washed water and brine. The organic layers are dried over magnesium sulfate and reduced in vacuo. The target compound is the purified by silica gel chromatography.

Example 2—Synthesis of S,S-bis(2-propionamidoethyl) butanebis(thioate) (NV038, 01-038)

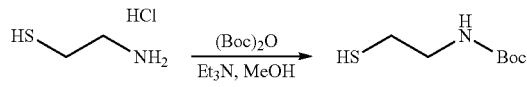

To a solution of cysteamine hydrochloride (5.0 g, 44 mmol) in CH$_3$OH (50 mL) was added Et$_3$N (4.4 g, 44 mmol), followed by (Boc)$_2$O (10.5 g, 48.4 mmol) and the mixture was stirred at room temperature for 1 h. The reaction mixture was concentrated in vacuo. The obtained residue was dissolved in CH$_2$Cl$_2$, washed with 2M HCl aqueous solution and brine, dried over Na$_2$SO$_4$, filtered and evaporated to yield tert-butyl 2-mercaptoethylcarbamate as a colorless oil which was used in the next step without further purification.

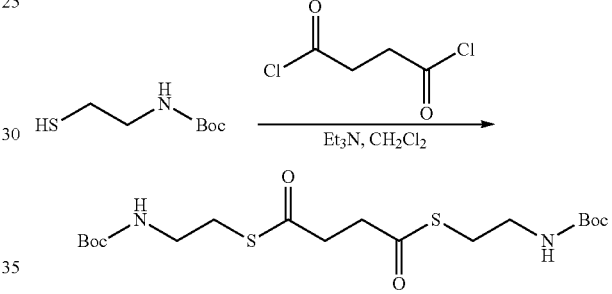

tert-Butyl 2-mercaptoethylcarbamate (9.8 g, 55.0 mmol) and Et$_3$N (5.6 g, 55.0 mmol) were dissolved in CH$_2$Cl$_2$ (100 mL), the mixture cooled to 0° C., succinyl chloride (2.1 g, 13.8 mmol) was added with dropwise. Then the mixture was stirred at room temperature for 2 h. The reaction mixture concentrated and the residue was purified by column chromatography (petrol ether/EtOAc=1/10 to 1/1). S,S-bis(2-(tert-butoxycarbonylamino)ethyl) butanebis(thioate) was obtained as a white solid.

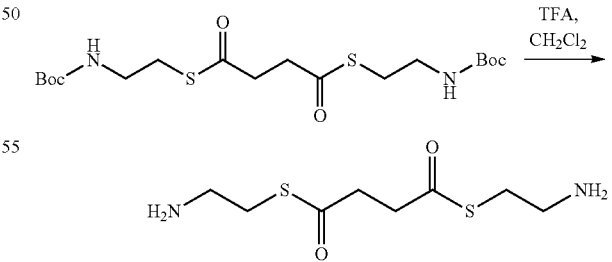

A mixture of S,S-bis(2-(tert-butoxycarbonylamino)ethyl) butanebis(thioate) (2.0 g, 4.58 mmol) and TFA (10 mL) in CH$_2$Cl$_2$ (10 mL) was stirred at room temperature for 4 hours. The reaction mixture was concentrated to yield S,S-bis(2-aminoethyl) butanebis(thioate) as a yellow oil which was used in the next step without further purification.

47

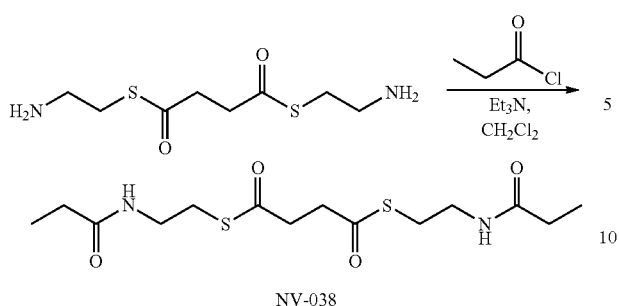

NV-038

S,S-bis(2-aminoethyl) butanebis(thioate) (1.1 g, 4.58 mmol) and Et₃N (1.4 g, 13.74 mmol) were dissolved in CH₂Cl₂ (15 mL), the mixture cooled to 0° C., propionyl chloride (0.9 g, 10.07 mmol) was added with dropwise. Then the mixture was stirred at room temperature for 3 hours. The reaction mixture concentrated and the residue was purified by preparative TLC (CH₂Cl₂/MeOH=15/1). S,S-bis(2-Propionamidoethyl) butanebis(thioate) was obtained as a white solid.

Example 3—synthesis of (R)-4-(2-carboxy-2-propionamidoethylthio)-4-oxobutanoic acid (NV-041, 01-041)

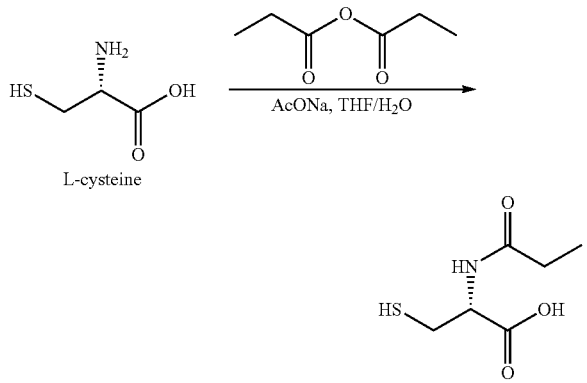

L-cysteine

To a mixture of L-cysteine (2.00 g, 16.5 mmol) in THF/H₂O (8 mL/2 mL) was added NaOAc (2.70 g, 33.0 mmol). The mixture was stirred at room temperature for 20 min. The reaction was cooled to 5° C. before propionic anhydride (2.30 g, 17.6 mmol) was added dropwise. The reaction mixture was stirred at room temperature overnight and then heated to reflux for 4 hours. The reaction mixture was cooled and acidified to pH 5 by adding 4N HCl. The resulting solution was evaporated under reduced pressure to remove THF. The residue was purified by prep-HPLC (eluting with H₂O (0.05% TFA) and CH₃CN) to give 1.00 g of (R)-3-mercapto-2-propionamidopropanoic acid as colourless oil.

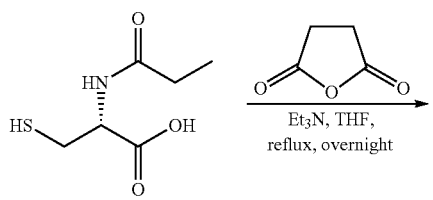

48

-continued

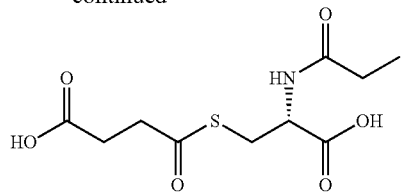

A solution of (R)-3-mercapto-2-propionamidopropanoic acid (1.00 g, 5.65 mmol), succinic anhydride (565 mg, 5.65 mmol) and Et₃N (572 mg, 5.65 mmol) in 10 mL of THF was heated under reflux overnight. The reaction mixture concentrated and the residue was purified by preparative-HPLC (eluting with H₂O (0.05% TFA) and CH₃CN) to yield (R)-4-(2-carboxy-2-propionamidoethylthio)-4-oxobutanoic acid as a colourless oil.

Example 4

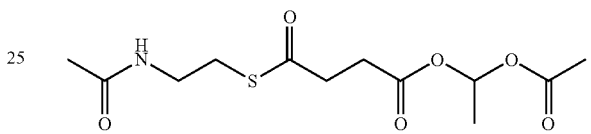

Step 1

Triethylamine (0.24 mol) is added to a solution of N-acetylcysteamine (0.2 mol) in DCM. 4-Chloro-4-oxobutanoic acid (0.1 mol) is added dropwise, and the reaction mixture is stirred at room temperature. The mixture is added to aqueous dilute hydrochloric acid and is extracted with ethyl acetate, and then is washed water and brine. The organic layers are dried over magnesium sulfate and reduced in vacuo.

Step 2

The product of step 3 (0.1 mol), acetic acid 1-bromoethyl ester (0.1 mol) and caesium carbonate (0.12 mol) is suspended in DMF and stirred at 60° C. under an inert atmosphere. The suspension is allowed to cool to room temperature and ethyl acetate added and is washed successively with aqueous dilute hydrochloric acid and water. The organics are dried over magnesium sulfate and reduced in vacuo. The residue is purified by column chromatography.

Example 5

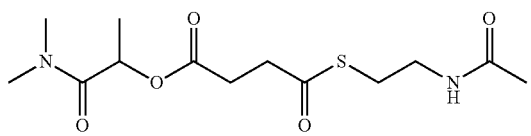 [SMILES: CC(=O)NCCSC(=O)CCC(=O)OC(C)C(=O)N(C)C]

Step 1

Triethylamine (0.24 mol) is added to a solution of N-acetylcysteamine (0.2 mol) in DCM. 4-Chloro-4-oxobutanoic acid (0.1 mol) is added dropwise, and the reaction mixture is stirred at room temperature. The mixture is added to aqueous dilute hydrochloric acid and is extracted with ethyl acetate, and then is washed water and brine. The organic layers are dried over magnesium sulfate and reduced in vacuo.

Step 2

Dimethylamine (0.1 mol) and triethylamine (0.1 mol) are diluted in dichloromethane, the solution is cooled to 0° C. and 2-chloropropionyl chloride (0.1 mol) in DCM is added and the solution is allowed to warm to room temperature and is left to stir under an inert atmosphere. The solution is washed with water. The organics are combined and the volatiles are removed in vacuo. The residue is purified by silica gel chromatography.

Step 3

2-Chloro-N,N-dimethyl-propionamide (0.1 mol), the product of step 1 (0.1 mol), caesium carbonate (0.1 mol), and sodium iodide (0.01 mol) is suspended in DMF and the suspension stirred at 80° C. under an inert atmosphere. The suspension is cooled to room temperature, is diluted with ethyl acetate and is washed with water. The organics are reduced in vacuo. The residue is purified by silica gel chromatography to yield the target compound.

Example 6—synthesis of
4-oxo-4-(2-propionamidoethylthio)butanoic acid
(NV114, 01-114)

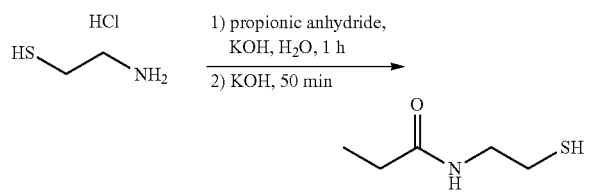

Propionic anhydride (11.7 g, 89.7 mmol) and aqueous KOH (8 M, to maintain pH=8) were added dropwise to a stirred solution of cysteamine hydrochloride (3.40 g, 30.0 mmol) in 24 mL of water. The mixture was neutralized by adding 2N HCl and stirred for 1 hour at room temperature. The solution was cooled with an ice bath and solid KOH (6.00 g, 105 mmol) was added slowly. The mixture was stirred for 50 minutes at room temperature. After saturated with NaCl and neutralized with 6N HCl, the mixture was extracted with $CH_2Cl_2$ (4×30 mL). The combined $CH_2Cl_2$ extracts were dried ($Na_2SO_4$) and concentrated in vacuo to give N-(2-mercaptoethyl)propionamide as colourless oil, which was used for next step without further purification.

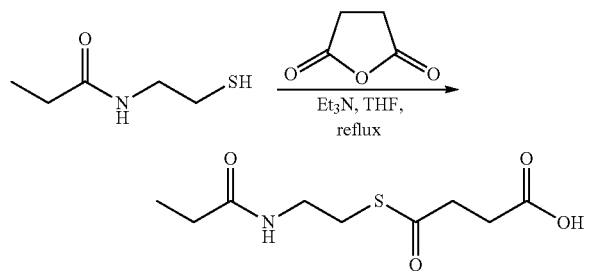

A solution of N-(2-mercaptoethyl)propionamide (2.00 g, 15.0 mmol), succinic anhydride (1.50 g, 15.0 mmol) and $Et_3N$ (1.50 g, 15.0 mmol) in 20 mL of THF was heated under reflux overnight. The reaction mixture was concentrated and the residue was purified by preparative-HPLC (eluting with $H_2O$ (0.05% TFA) and $CH_3CN$) to yield 4-oxo-4-(2-propionamidoethylthio)butanoic acid as colourless oil.

Example 7—synthesis of
4-(2-acetamidoethylthio)-4-oxobutanoic acid
(NV108, 01-108)

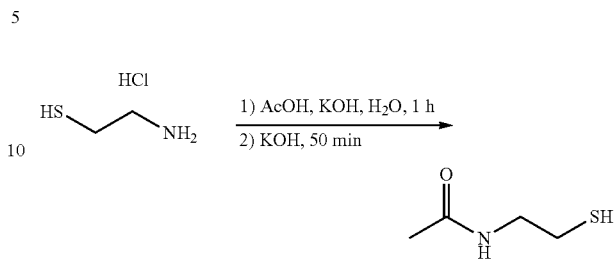

Acetic anhydride (8.48 mL, 90.0 mmol) and aqueous KOH (8 M, to maintain pH=8) were added dropwise to a stirred solution of cysteamine hydrochloride (3.40 g, 30.0 mmol) in 24 mL of water. The pH was then adjusted to 7 with adding 2N HCl. The mixture was stirred for 1 hour at room temperature, and then the solution was cooled with an ice bath. To the above solution, solid KOH (6.0 g, 105 mmol) was added slowly, and the resulting mixture was stirred for 50 minutes at room temperature. After saturated with NaCl and neutralized with 6N HCl, the mixture was extracted with $CH_2Cl_2$ (4×30 mL). The combined $CH_2Cl_2$ extracts were dried ($Na_2SO_4$) and concentrated in vacuo to give N-(2-mercaptoethyl)acetamide as colourless oil, which was used for next step without further purification.

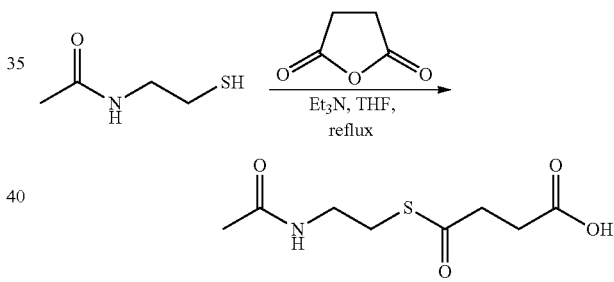

A solution of N-(2-mercaptoethyl)acetamide (1.50 g, 12.7 mmol), succinic anhydride (1.3 g, 12.7 mmol) and $Et_3N$ (1.3 g, 12.7 mmol) in 20 mL of THF was heated under reflux overnight. The reaction mixture was concentrated and the residue was purified by preparative HPLC (eluting with $H_2O$ (0.05% TFA) and $CH_3CN$) to yield 4-(2-acetamidoethylthio)-4-oxobutanoic acid as colourless oil.

Example 8—The synthesis of (R)-3-(4-((R)-2-carboxy-2-propionamidoethylthio)-4-oxobutanoylthio)-2-propionamidopropanoic acid (NV099, 01-099)

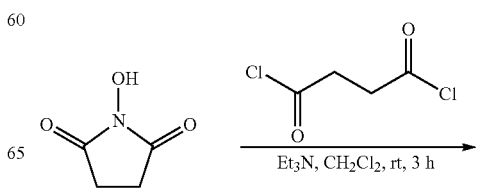

-continued

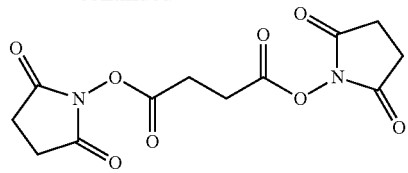

To a mixture of N-hydroxysuccinimide (3.00 g, 26.1 mmol) and Et₃N (3.20 g, 31.3 mmol) in CH₂Cl₂ (60 mL) was added dropwise succinyl chloride (2.00 g, 13.0 mmol). The mixture was stirred at room temperature for 3 hours before diluted with water (60 mL). The resulting suspension was filtered, washed with water and CH₂Cl₂. The cake was collected and dried to give bis(2,5-dioxopyrrolidin-1-yl) succinate as a grey solid.

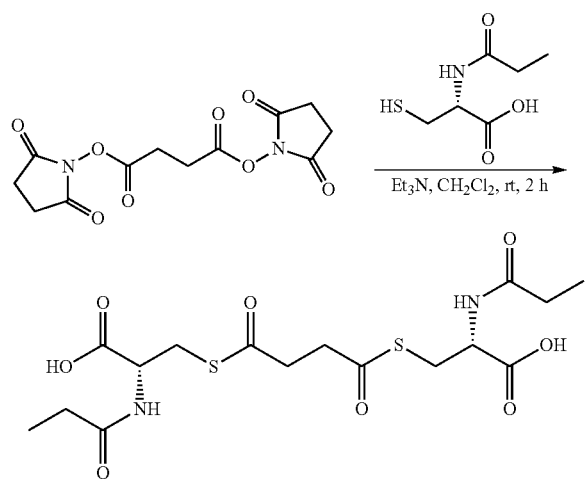

A mixture of N-(2-mercaptoethyl)propionamide (400 mg, 2.26 mmol), bis(2,5-dioxopyrrolidin-1-yl) succinate (353 mg, 1.13 mmol) and TEA (286 mg, 2.83 mmol) in 3.0 mL of CH₃CN was stirred at room temperature for 2 hours. The clear reaction solution was purified by preparative-HPLC (eluting with H₂O (0.05% TFA) and CH₃CN) directly to yield (R)-3-(4-((R)-2-carboxy-2-propionamidoethylthio)-4-oxobutanoylthio)-2-propionamidopropanoic acid as colorless oil.

Example 9—Synthesis of (R)-4-(1-carboxy-2-(propionylthio)ethylamino)-4-oxobutanoic acid (NV122, 01-122)

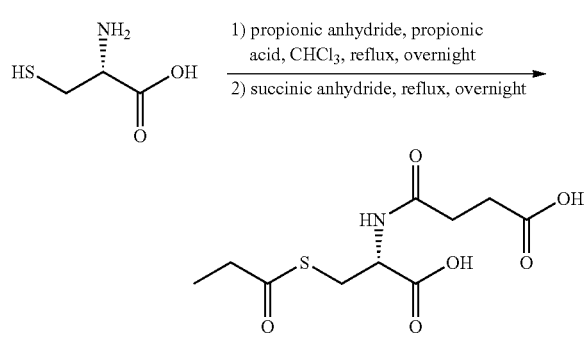

To a mixture of (R)-3-mercapto-2-propionamidopropanoic acid (1.00 g, 8.25 mmol) and propionic acid (1.0 mL) in CHCl₃ (10 mL) were added propionic anhydride (1.13 g, 8.67 mmol) dropwise. The reaction mixture was heated to reflux overnight. The reaction mixture was cooled and succinic anhydride (1.00 g, 9.99 mmol) was added. The mixture was refluxed overnight before concentrated under reduced pressure. The residue was purified by prep-HPLC (eluting with H₂O (0.05% TFA) and CH3CN) to yield (R)-4-(1-carboxy-2-(propionylthio)ethylamino)-4-oxobutanoic acid as an off-white solid.

Example 10—The synthesis of 4-(1-acetamido-2-methylpropan-2-ylthio)-4-oxobutanoic acid (NV188, 01-188)

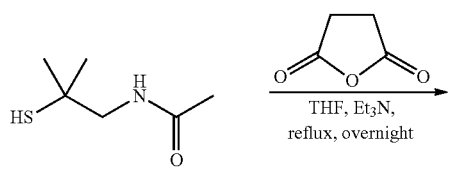

To a stirred solution of cysteamine hydrochloride (2.00 g, 14.1 mmol) in 15 mL of water was added acetic anhydride (4.30 g, 42.4 mmol) and aqueous KOH (8 M, to maintain pH=8) dropwise. The mixture was then neutralized by adding 2N HCl and stirred for 1 hour at room temperature. To the solution cooled with an ice bath was added slowly solid KOH (2.80 g, 49.4 mmol) and the mixture was stirred for 50 minutes at room temperature. After saturated with NaCl and neutralized with 6N HCl, the mixture was extracted with CH₂Cl₂ twice. The combined CH₂Cl₂ extracts were dried (Na₂SO₄) and concentrated in vacuo to yield N-(2-mercapto-2-methylpropyl)acetamide as a white solid which was used for next step without further purification.

A solution of N-(2-mercapto-2-methylpropyl)acetamide (400 mg, 2.72 mmol), succinic anhydride (326 mg, 3.26 mmol) and Et₃N (330 mg, 3.26 mmol) in 6 mL of THF was heated under overnight. The reaction mixture was concentrated and the residue was purified by preparative-HPLC (eluting with H₂O (0.05% TFA) and CH₃CN) to yield 4-(1-acetamido-2-methylpropan-2-ylthio)-4-oxobutanoic acid as yellow oil.

Example 11—The synthesis of S,S-bis((R)-3-(diethylamino)-3-oxo-2-propionamidopropyl) butanebis(thioate) (NV185, 01-185)

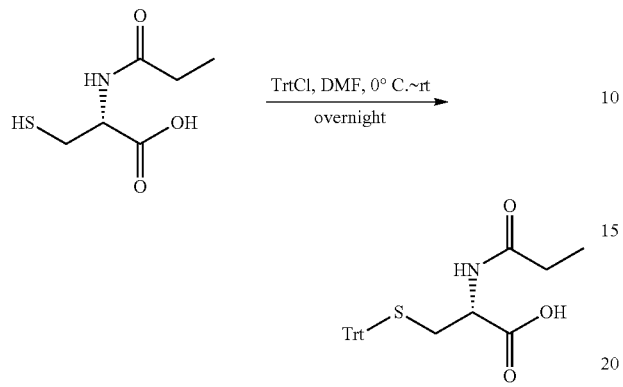

To a solution of (R)-3-mercapto-2-propionamidopropanoic acid (5.00 g, 28.0 mmol) in DMF (50 mL) was added triphenylmethyl chloride (8.70 g, 31.0 mmol) at 0° C. The mixture was stirred at 0° C. for 30 min and then warmed to room temperature overnight. The mixture was treated with water and extracted with EtOAc twice. The combined organic layers were washed with brine, dried over Na$_2$SO$_4$ and concentrated under reduced pressure. The residue was purified by silica gel column chromatography (CH$_2$Cl$_2$/MeOH=80/1~50/1) to yield (R)-2-propionamido-3-(tritylthio)propanoic acid as a white solid.

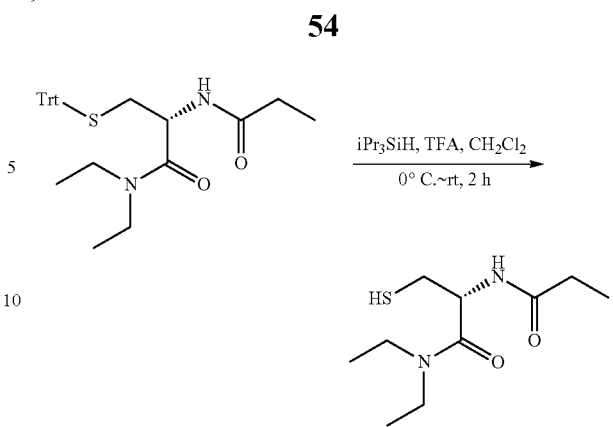

To a stirred solution of (R)-2-propionamido-3-(tritylthio) propanoic acid (1.7 g, 4.0 mmol) in CH$_2$Cl$_2$ (50 mL) was added DCC (1.7 g, 8.0 mmol) and HOBT (0.50 g, 4.0 mmol) at room temperature. The mixture was stirred at room temperature for 1 h and then diethylamine (0.80 g, 8.0 mmol) was added. The mixture was stirred at room temperature overnight. The mixture was washed with water, dried over Na$_2$SO$_4$ and concentrated under reduced pressure to give the crude product which was purified by silica gel column chromatography (EtOAc/petrol ether=1/6~1/1) to yield (R)—N,N-diethyl-3-mercapto-2-propionamidopropanamide as yellow oil.

To a solution of (R)—N,N-diethyl-3-mercapto-2-propionamidopropanamide (400 mg, 0.800 mmol) in CH$_2$Cl$_2$ (10 mL) at 0° C. was added TFA (1 mL) and i-Pr3SiH (253 mg, 1.60 mmol). The mixture was warmed to room temperature and stirred for 2 hours. The solution was evaporated under reduced pressure. The residue was purified by preparative-HPLC (eluting with H$_2$O (0.5% TFA) and CH$_3$CN) to yield (R)—N,N-diethyl-3-mercapto-2-propionamidopropanamide as yellow oil.

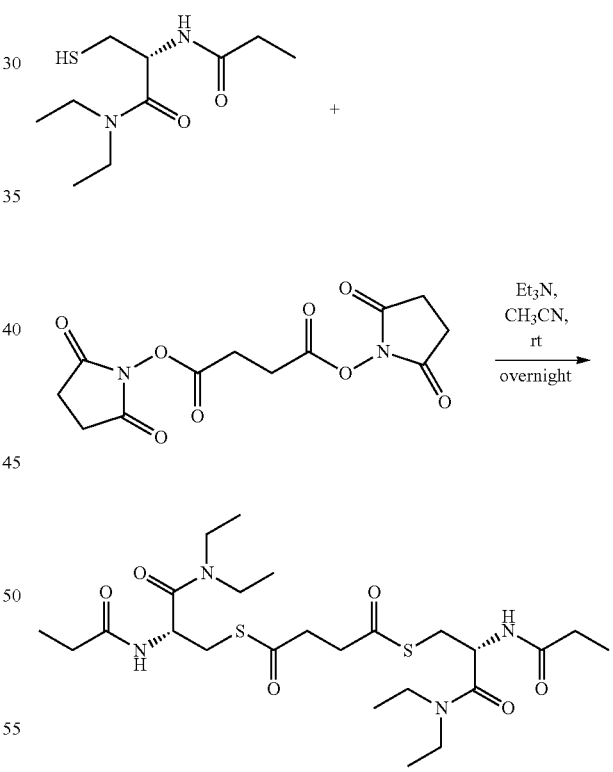

A mixture of (R)—N,N-diethyl-3-mercapto-2-propionamidopropanamide (150 mg, 0.600 mmol), Et$_3$N (242 mg, 2.40 mmol) and bis(2,5-dioxopyrrolidin-1-yl) succinate (94 mg, 0.30 mmol) in CH$_3$CN (100 mL) was stirred at room temperature overnight. The mixture was evaporated under reduced pressure. The residue was purified by preparative HPLC (eluting with H$_2$O (0.5% TFA) and CH$_3$CN) to yield S,S-bis((R)-3-(diethylamino)-3-oxo-2-propionamidopropyl) butanebis(thioate) (36% yield) as a yellow solid.

Example 12—The synthesis of 4-(2-(2-(diethylamino)-2-oxoethoxy)ethylthio)-4-oxobutanoic acid (NV193, 01-193)

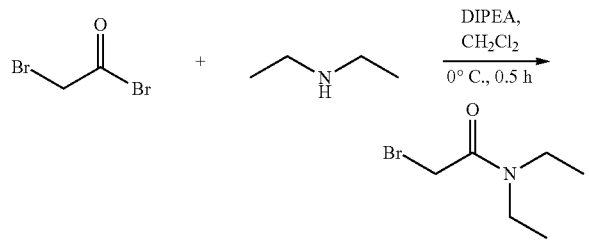

To a solution of 2-bromoacetyl bromide (4.00 g, 20.0 mmol) and DIPEA (2.60 g, 20 mmol) in CH$_2$Cl$_2$ (50 mL) was added dropwise diethylamine (1.60 g, 20.0 mmol) at 0° C. The mixture was stirred at 0° C. for 30 min. The solution was evaporated under reduced pressure to remove CH$_2$Cl$_2$. The residue was purified by silica gel column chromatography (EtOAc/petrol ether=1/5~1/2) to yield 2-bromo-N,N-diethylacetamide as yellow oil.

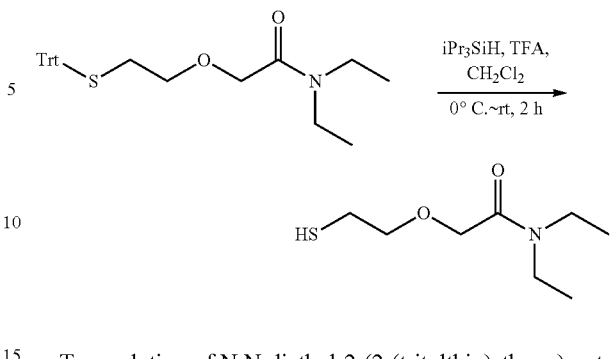

A solution of 2-mercaptoethanol (2.50 g, 32.0 mmol), triphenylmethyl chloride (10.7 g, 38.4 mmol) in 100 mL of THF was heated under reflux overnight. The reaction mixture was concentrated and the residue was purified by silica gel column chromatography (EtOAc/petrol ether=1/5~1/1) to yield 2-(2,2,2-triphenylethylthio)ethanol as a white solid.

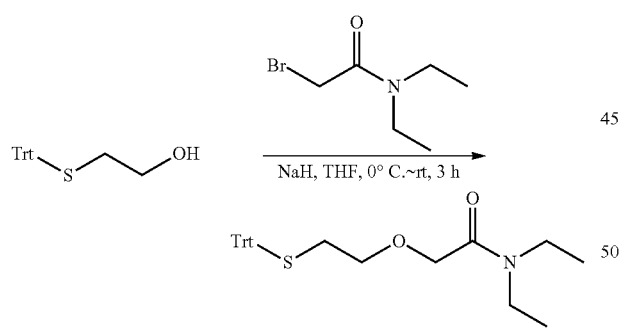

To a solution of 2-(2,2,2-triphenylethylthio)ethanol (3.50 g, 10.9 mmol) in THF (30 mL) was added NaH (0.500 g, 13.0 mmol, 60% in oil) in portions at 0° C. The reaction mixture was stirred at 0° C. for 1 hour. Then a solution of 2-bromo-N,N-diethylacetamide (2.1 g, 10.9 mmol) in THF (5 mL) was added dropwise. The resulting mixture was warmed to room temperature over 2 hours. The mixture was quenched with water and extracted with EtOAc twice. The combined organic layers were washed with brine, dried over Na$_2$SO$_4$ and concentrated under reduced pressure. The residue was purified by silica gel column chromatography (EtOAc/petrol ether=1/5~1/2) to yield N,N-diethyl-2-(2-(tritylthio)ethoxy)acetamide as a white solid.

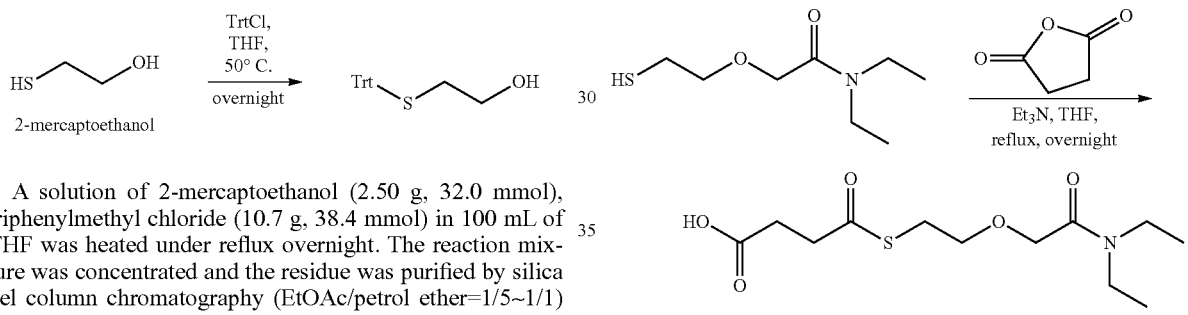

To a solution of N,N-diethyl-2-(2-(tritylthio)ethoxy)acetamide (2.70 g, 6.30 mmol) in CH$_2$Cl$_2$ (20 mL) was added TFA (2 mL) and i-Pr$_3$SiH (2.00 g, 12.6 mmol) at 0° C. The mixture was warmed to room temperature and stirred for 2 hours. The solution was evaporated under reduced pressure to remove CH$_2$Cl$_2$. The residue was purified by silica gel column chromatography (EtOAc/petrol ether=1/5~1/1) to yield N,N-diethyl-2-(2-mercaptoethoxy)acetamide as colorless oil.

A solution of N,N-diethyl-2-(2-mercaptoethoxy)acetamide (356 mg, 1.90 mmol), succinic anhydride (200 mg, 2.10 mmol) and Et$_3$N (300 mg, 2.90 mmol) in 10 mL of THF was stirred at reflux overnight. The reaction mixture was concentrated in vacuo and the residue was purified by preparative HPLC (eluting with H$_2$O (0.5% TFA) and CH$_3$CN) to yield 4-(2-(2-(diethylamino)-2-oxoethoxy)ethylthio)-4-oxobutanoic acid as colorless oil.

Example 13—The synthesis of (R)-methyl 3-(4-((R)-3-methoxy-3-oxo-2-propionamidopropylthio)-4-oxobutanoylthio)-2-propionamidopropanoate (NV205, 01-205)

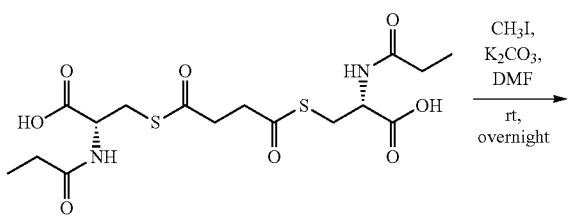

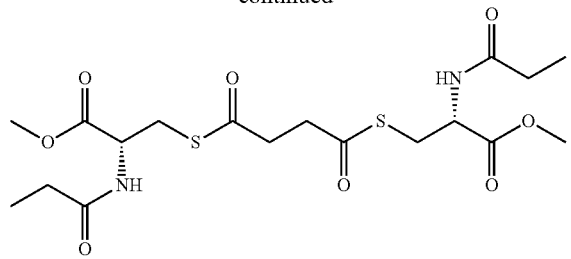

A mixture of (R)-3-(4-((R)-2-carboxy-2-propionamido-ethylthio)-4-oxobutanoylthio)-2-propionamidopropanoic acid (300 mg, 0.69 mmol), $CH_3I$ (293 mg, 2.06 mmol) and $K_2CO_3$ (475 mg, 3.44 mmol) in 4.0 mL of DMF was stirred at room temperature overnight. The reaction mixture was filtered and the filtrate was purified by preparative-HPLC (eluting with $H_2O$ (0.05% TFA) and $CH_3CN$) directly to yield (R)-methyl 3-(4-((R)-3-methoxy-3-oxo-2-propionami-dopropylthio)-4-oxobutanoylthio)-2-propionamidopropano-ate as an off-white solid.

Example 14—Synthesis of NV189

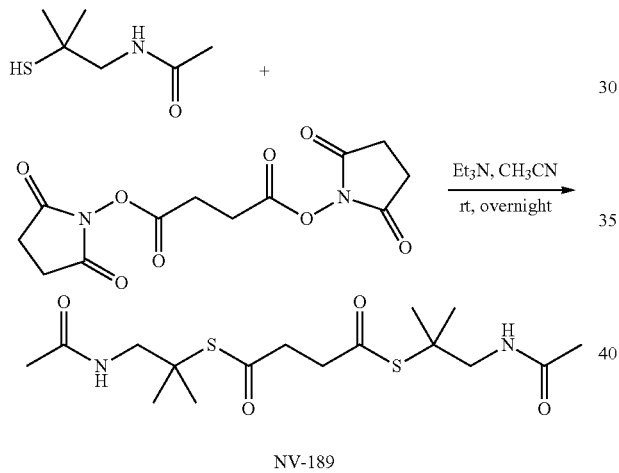

A mixture of N-(2-mercapto-2-methylpropyl)acetamide (400 mg, 2.72 mmol), bis(2,5-dioxopyrrolidin-1-yl) succinate (339 mg, 1.09 mmol) and $Et_3N$ (550 mg, 5.44 mmol) in 6 mL of $CH_3CN$ was stirred at room temperature overnight. The reaction mixture was concentrated and the residue was purified by preparative HPLC (eluting with $H_2O$ (0.05% TFA) and $CH_3CN$) to yield NV189 as an off-white solid.

Example 15—Synthesis of S,S-bis(2-(2-(diethyl-amino)-2-oxoethoxy)ethyl) butane-bis(thioate) (NV195, 01-195)

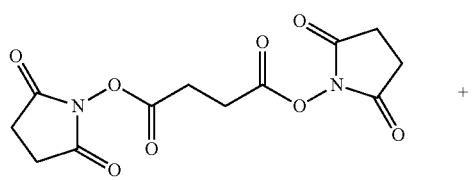

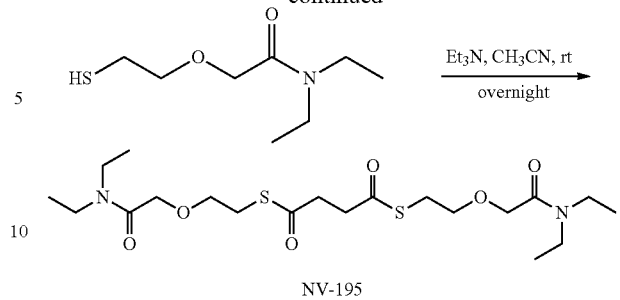

To a solution of N,N-diethyl-2-(2-mercaptoethoxy)acet-amide (438 mg, 2.3 mmol) in $CH_3CN$ (10 mL) was added bis(2,5-dioxopyrrolidin-1-yl) succinate (374 mg, 1.2 mmol) and $Et_3N$ (232 mg, 2.3 mmol). The mixture was stirred at room temperature overnight. The reaction mixture was concentrated in vacuo and the residue was purified by preparative HPLC (eluting with $H_2O$ (0.5% TFA) and $CH_3CN$) to yield S,S-bis(2-(2-(diethylamino)-2-oxoethoxy)ethyl) butanebis(thioate) as a colorless oil.

Example 16—Synthesis of NV206

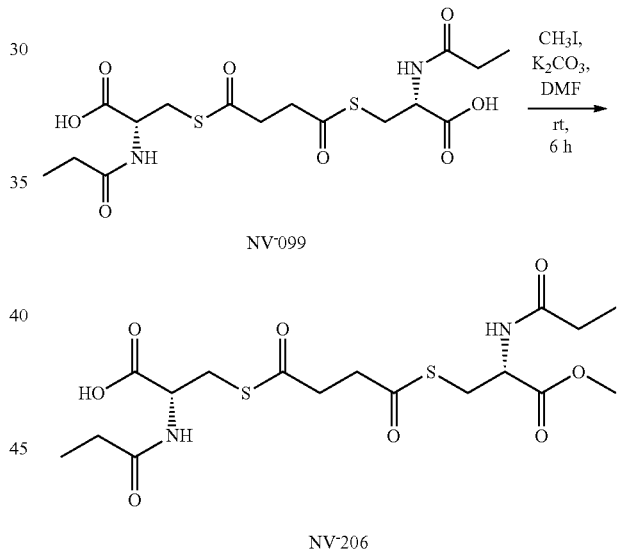

A mixture of (R)-3-(4-((R)-2-carboxy-2-propionamido-ethylthio)-4-oxobutanoylthio)-2-propionamidopropanoic acid (400 mg, 0.916 mmol), $CH_3I$ (156 mg, 1.1 mmol) and $K_2CO_3$ (190 mg, 1.37 mmol) in 4 mL of DMF was stirred at room temperature for 6 hours. The reaction mixture was filtered and the filtrate was purified by prep-HPLC (eluting with $H_2O$ (0.05% TFA) and $CH_3CN$) directly to yield NV206 as a colorless gum.

Example 17

Results of Biological Experiments

The compounds given in the following table were subject to the assays (1)-(4) mentioned under the heading I. Assay for evaluating enhancement and inhibition of mitochondrial energy producing function in intact cells. In the following table the results are shown, which indicate that all compounds tested have suitable properties. Importantly, all compounds show specific effect on CII-linked respiration as seen from screening protocols 1 and 4, as well as a convergent effect, with CI-substrates available, as seen in assay 2.

Results from screening protocols 1-4
Compound numbers as set out in Examples 1-16.

| Compound NV | Convergent (Routine) | Convergent (FCCP) | CII (plasma) | CII | Uncoupling | Toxicity |
|---|---|---|---|---|---|---|
| 01-193 | (++) | + | (+) | + | + | 5 mM |
| 01-188 | +++ | +++ | + | + | (+) | 5 mM |
| 01-185 | (+) | + | + | + | (+) | 2 mM |
| 01-205 | +++ | ++ | + | ++ | (+) | 5 mM |
| 01-114 | +++ | ++ | + | ++ | (+) | 10 mM |
| 01-041 | + | +++ | + | ++ | (+) | 5 mM |
| 01-108 | ++ | ++ | (+) | (++) | + | 10 mM |

Legend: Convergent (Routine) - the increase in mitochondrial oxygen consumption induced by the compound under conditions described in screening assay 3; Convergent (FCCP) - the increase in mitochondrial oxygen consumption induced by the compound under conditions described in screening assay 2 (uncoupled conditions); Convergent (plasma) - the increase in mitochondrial oxygen consumption induced by the compound in cells with inhibited complex I incubated in human plasma, as described in screening assay 4; CII - the increase in mitochondrial oxygen consumption induced by the compound in cells with inhibited complex I as described in screening assay 1; Uncoupling - the level of oxygen consumption after addition of oligomycin as described in screening assay 3. The response in each parameter is graded either +, ++ or +++ in increasing order of potency.
Brackets [( )] indicate an intermediate effect, i.e. (+++) is between ++ and +++.
Toxicity - the lowest concentration during compound titration at which a decrease in oxygen consumption is seen as described in screening assay 2.

Examples 18-20

Metformin Studies

In the metformin study the following compounds were used (and which are referred to in the figures). The compounds are described in WO 2014/053857.

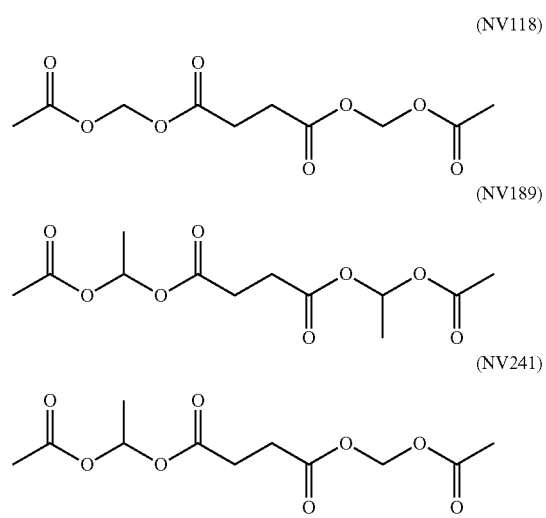

(NV118)

(NV189)

(NV241)

Sample Acquisition and Preparation

The study was performed with approval of the regional ethical review board of Lund University, Sweden (ethical review board permit no. 2013/181). Venous blood from 18 healthy adults (11 males and 7 females) was drawn in $K_2$EDTA tubes (BD Vacutainer® Brand Tube with dipotassium EDTA, BD, Plymouth, UK) according to clinical standard procedure after written informed consent was acquired. For platelet isolation the whole blood was centrifuged (Multifuge 1 S-R Heraeus, Thermo Fisher Scientifics, Waltham, USA) at 500 g at room temperature (RT) for 10 min. Platelet-rich plasma was collected to 15 mL falcon tubes and centrifuged at 4600 g at RT for 8 min. The resulting pellet was resuspended in 1-2 mL of the donor's own plasma. PBMCs were isolated using Ficol gradient centrifugation (Boyum, 1968). The blood remaining after isolation of platelets was washed with an equal volume of physiological saline and layered over 3 mL of Lymphoprep™. After centrifugation at 800 g at RT (room temperature) for 30 min the PBMC layer was collected and washed with physiological saline. Following a centrifugation at 250 g at RT for 10 min the pellet of PBMCs was resuspended in two parts of physiological saline and one part of the donor's own plasma. Cell count for both PBMCs and platelets were performed using an automated hemocytometer (Swelab Alfa, Boule Medical AB, Stockholm, Sweden).

Aim of Study Reported in Examples 18-19

Metformin Induces Lactate Production in Peripheral Blood Mononuclear Cells and Platelets Through Specific Mitochondrial Complex I Inhibition Metformin is a widely used anti-diabetic drug associated with the rare side-effect of lactic acidosis, which has been proposed to be linked to drug-induced mitochondrial dysfunction. Using respirometry, the aim of the study reported in Examples 1-2 below was to evaluate mitochondrial toxicity of metformin to human blood cells in relation to that of phenformin, a biguanide analog withdrawn in most countries due to a high incidence of lactic acidosis.

Aim of the Study Reported in Example 20

The aim is to investigate the ability of succinate prodrugs to alleviate or circumvent undesired effects of metformin and phenformin.

Example 18A

Effects of Metformin and Phenformin on Mitochondrial Respiration in Permeabilized Human Platelets In order to investigate the specific target of biguanide toxicity, a protocol was applied using digitonin permeabilization of the blood cells and sequential additions of respiratory complex-specific substrates and inhibitors in MiR05 medium. After stabilization of routine respiration, i.e. respiration of the cells with their endogenous substrate supply and ATP demand, metformin, phenformin or their vehicle (double-deionized water) were added. A wide concentration range of the drugs was applied; 0.1, 0.5, 1, and 10 mM metformin and 25, 100 and 500 µM phenformin. After incubation with the drugs for 10 min at 37° C., the platelets were permeabilized with digitonin at a previously determined optimal digitonin concentration (1 µg $10^{-6}$ platelets) to induce maximal cell membrane permeabilization without disruption of the mitochondrial function and allowing measurements of maximal respiratory capacities (Sjövall et al. 2013a). For evaluation of complex I-dependent oxidative phosphorylation capacity ($OXPHOS_{CI}$) first, the NADH-linked substrates pyruvate and malate (5 mM), then ADP (1 mM) and, at last, the additional complex I substrate glutamate (5 mM) were added sequentially. Subsequently the $FADH_2$-linked substrate succinate (10 mM) was given to determine convergent complex I- and II-dependent OXPHOS capacity ($OXPHOSc_{CI+II}$). $LEAK_{I+II}$ state, a respiratory state where oxygen consumption is compensating for the back-flux of protons across the mitochondrial membrane (Gnaiger, 2008), was assessed by addition of the ATP-synthase inhibitor oligomycin (1 µg mL$^{-1}$). Maximal uncoupled respiratory electron transport system capacity supported by convergent input through complex I and II (ETS$_{CI+II}$) was evaluated by subsequent titration with the protonophore carbonylcyanide p-(trifluoromethoxy) phenylhydrazone (FCCP). Addition of the complex I inhibitor rotenone (2 µM) revealed complex II-dependent maximal uncoupled respiration (ETS$_{CII}$). The complex III inhibitor antimycin (1 µg mL$^{-1}$) was then given to reveal residual oxygen consumption (ROX). Finally, the artificial complex IV substrate N,N,N',N'-tetramethyl-p-phenylenediamine dihydrochloride (TMPD, 0.5 mM) was added and the complex IV inhibitor sodium azide (10 mM) was given to measure complex IV activity and chemical background, respectively. Complex IV activity was calculated by subtracting the sodium azide value from the TMPD value. With exception of complex IV activity, all respiratory states were measured at steady-state and corrected for ROX. Complex IV activity was measured after ROX determination and not at steady-state. The integrity of the outer mitochondrial membrane was examined by adding cytochrome c (8 µM) during OXPHOS$_{CI+II}$ in presence of vehicle, 100 mM metformin or 500 µM phenformin.

Example 18B

Effect of Metformin on Mitochondrial Respiration in Permeabilized Human Peripheral Blood Mononuclear Cells and on Mitochondrial Respiration in Intact Human Platelets For analysis of respiration of permeabilized PBMCs in response to metformin (0.1, 1 and 10 mM) the same protocol as for permeabilized platelets was used, except the digitonin concentration was adjusted to 6 µg 10$^{-6}$ PBMCs (Sjövall et al., 2013b).
Results Respiration using complex I substrates was dose-dependently inhibited by metformin in both permeabilized human PBMCs and platelets (FIG. 1). OXPHOS$_{CI}$ capacity decreased with increasing concentrations of metformin compared to controls with near complete inhibition at 10 mM (−81.47%, P<0.001 in PBMCs and −92.04%, P<0.001 in platelets), resulting in an IC$_{50}$ of 0.45 mM for PBMCs and 1.2 mM for platelets. Respiratory capacities using both complex I- and complex II-linked substrates, OXPHOS$_{CI+II}$ and ETS$_{CI+II}$, were decreased similarly to OXPHOS$_{CI}$ by metformin as illustrated by the representative traces of simultaneously measured O$_2$ consumption of vehicle-treated and 1 mM metformin-treated permeabilized PBMCs (FIG. 5a). In contrast, ETS$_{CII}$ capacity and complex IV activity did not change significantly in presence of metformin compared to controls in either cell type (FIG. 5b, c) and neither did LEAK$_{I+II}$ respiration (the respiratory state where oxygen consumption is compensating for the back-flux of protons across the mitochondrial membrane, traditionally denoted state 4 in isolated mitochondria, data not shown). The mitochondrial inhibition of complex I induced by metformin did not seem to be reversible upon extra- and intracellular removal of the drug by washing and permeabilizing the cells, respectively. Although the severity of the insult of complex I inhibition was attenuated by removal (probably attributed to a shorter exposure time of the drug) platelets did not regain routine and maximal mitochondrial function comparable to control (data not shown). Phenformin likewise inhibited OXPHOS$_{CI}$ (FIG. 6), OXPHOS$_{CI+II}$ and ETS$_{CI+II}$ but not ETS$_{CII}$ or respiration specific to complex IV (data not shown). Phenformin demonstrated a 20-fold more potent inhibition of OXPHOS$_{CI}$ in permeabilized platelets than metformin (IC$_{50}$ 0.058 mM and 1.2 mM, respectively) (FIG. 2). Metformin and phenformin did not induce increased respiration following administration of cytochrome c and hence did not disrupt the integrity of the outer mitochondrial membrane.

After stabilization of routine respiration in MiR05 medium, either vehicle (double-deionized water) or 1, 10 and 100 mM metformin was added. Routine respiration was followed for 60 min at 37° C. before the ATP-synthase inhibitor oligomycin (1 µg mL$^{-1}$) was added to assess LEAK respiration. Maximal uncoupled respiratory electron transport system capacity supported by endogenous substrates (ETS) was reached by titration of FCCP. Respiration was sequentially blocked by the complex I inhibitor rotenone (2 µM), the complex III inhibitor antimycin (1 µg mL$^{-1}$) and the complex IV inhibitor sodium azide (10 mM) to assess ROX, which all respiration values were corrected for. In an additional experiment, whole blood was incubated in K$_2$EDTA tubes with different metformin concentrations (0.1, 0.5 and 1 mM) over a period of 18 h prior to isolation of platelets and analyses of respiration.
Results In intact human platelets, metformin decreased routine respiration in a dose- and time-dependent manner (FIG. 7a). When exposed to either metformin or vehicle the platelets showed a continuous decrease in routine respiration over time. After 60 min the routine respiration was reduced by −14.1% in control (P<0.05), by −17.27% at 1 mM (P<0.01), by −28.61% at 10 mM (P<0.001), and by −81.78% at 100 mM of metformin (P<0.001) compared to the first measurement after addition. Metformin at 100 mM decreased routine respiration significantly compared to control already after 15 min of exposure (−39.77%, P<0.01). The maximal uncoupled respiration of platelets (the protonophore-titrated ETS capacity) after 60 min incubation, was significantly inhibited by 10 mM (−23.86%, P<0.05) and 100 mM (−56.86%, P<0.001) metformin (FIG. 3b). LEAK respiration in intact cells was not significantly changed by metformin incubation (data not shown). When whole blood was incubated at a metformin concentrations of 1 mM over 18 h routine respiration of intact human platelets was reduced by 30.49% (P<0.05).

Example 19

Effect of Metformin and Phenformin on Lactate Production and pH of Intact Human Platelets Platelets were incubated for 8 h with either metformin (1 mM, 10 mM), phenformin (0.5 mM), rotenone (2 µM), or the vehicle for rotenone (DMSO). Lactate levels were determined every 2 h (n=5) using the Lactate Pro™ 2 blood lactate test meter (Arkray, Alere AB, Lidingö, Sweden) (Tanner et al. 2010). Incubation was performed at 37° C. at a stirrer speed of 750 rpm, and pH was measured at start, after 4 and after 8 h of incubation (n=4) using a PHM210 Standard pH Meter (Radiometer, Copenhagen, Denmark).
Results Lactate production increased in a time- and dose-dependent manner in response to incubation with metformin and phenformin in human platelets (FIG. 8a). Compared to control, metformin-(1 and 10 mM), phenformin-(0.5 mM), and rotenone-(2 µM) treated platelets all produced significantly more lactate over 8 h of treatment. At 1 mM metformin, lactate increased from 0.30±0.1 to 3.34±0.2 over 8 h and at 10 mM metformin, lactate increased from 0.22±0.1 to 5.76±0.7 mM. The corresponding pH dropped from 7.4±0.01 in both groups to 7.16±0.03 and 7.00±0.04 for 1 mM and 10 mM metformin, respectively. Phenformin-treated platelets (0.5 mM) produced similar levels of lactate as 10 mM metformin-treated samples. The level of lactate increase correlated with the decrease in pH for all treatment groups. The increased lactate levels in metformin-treated intact platelets also correlated with decreased absolute OXPHOS$_{CI}$ respiratory values seen in metformin-treated permeabilized platelets ($r^2$=0.60, P<0.001). A limited set of experiments further demonstrated that intact PBMCs also show increased lactate release upon exposure to 10 mM metformin (data not shown).

Discussion of the Results from Examples 18-19

This study demonstrates a non-reversible toxic effect of metformin on mitochondria specific for complex I in human platelets and PBMCs at concentrations relevant for the clinical condition of metformin intoxication. In platelets, we further have shown a correlation between decreased Complex I respiration and increased production of lactate. The mitochondrial toxicity we observed for metformin developed over time in intact cells. Phenformin, a structurally related compound now withdrawn in most countries due to a high incidence of LA, induced lactate release and pH decline in platelets through a complex I specific effect at substantially lower concentration.

In the present study, using a model applying high-resolution respirometry to assess integrated mitochondrial function of human platelets, we have demonstrated that the mitochondrial toxicity of both metformin and phenformin is specific to respiratory complex I and that a similar specific inhibition also is present in PBMCs. Complex I respiration of permeabilized PBMCs was 2.6-fold more sensitive to metformin than that of permeabilized platelets. However, due to the time-dependent toxicity of metformin (see below), the IC$_{50}$ is possibly an underestimation and could be lower if determined after longer exposure time. These findings further strengthen that the mitochondrial toxicity of metformin is not limited to specific tissues, as shown previously by others, but rather a generalized effect on a subcellular level. The metformin-induced complex IV inhibition in platelets reported by (Protti et al., 2012a, Protti et al. 2012b) has not been confirmed in this study or in an earlier study by Dykens et al. (2008) using isolated bovine mitochondria. Further, metformin and phenformin did not induce respiratory inhibition through any unspecific permeability changes of the inner or outer mitochondrial membranes as there were no evidence of uncoupling or stimulatory response following cytochrome c addition in presence of the drugs. High-resolution respirometry is a method of high sensitivity and allows O$_2$ measurements in the picomolar range. When applied to human blood cells ex vivo, it allows assessment of respiration in the fully-integrated state in intact cells, and permits exogenous supply and control of substrates to intact mitochondria in permeabilized cells. This is in contrast to enzymatic spectrophotometric assays which predominantly have been used in the research on mitochondrial toxicity of metformin, for instance by Dykens et al. (2008) and Owen et al. (2000). These assays measure the independent, not-integrated function of the single complexes and hence, are less physiological, which may contribute to the differences in results between our studies.

The results of the study demonstrated significant respiratory inhibition, lactate increase and pH decrease in intact platelet suspensions caused by metformin at concentrations relevant for intoxication already after 8-18 h. The time-dependent inhibition of mitochondrial respiration in combination with the lack of reversal following exchange of the extracellular buffer and dilution of intracellular content of soluble metformin by permeabilization of the cell point towards intramitochondrial accumulation being a key factor in the development of drug-induced mitochondrial dysfunction-related LA, as has been proposed by others (Chan et al., 2005, Lalau, 2010).

Phenformin's mitochondrial toxicity has been shown previously, for instance on HepG2 cells, a liver carcinoma cell line, and isolated mitochondria of rat and cow. Here we have demonstrated specific mitochondrial toxicity also using human blood cells. Compared to metformin, phenformin had a stronger mitochondrial toxic potency on human platelets (IC$_{50}$ 1.2 mM and 0.058 mM, respectively). Phenformin and metformin show a 10 to 15-fold difference in clinical dosing and 3 to 10-fold difference in therapeutic plasma concentration. In this study we have observed a 20-fold difference between phenformin and metformin in the potential to inhibit complex I. If translated to patients this difference in mitochondrial toxicity in relation to clinical dosing could potentially explain phenformin's documented higher incidence of phenformin-associated LA.

Standard therapeutic plasma concentrations of metformin are in the range of 0.6 and 6.0 µM and toxic concentrations lie between 60 µM and 1 mM. In a case report of involuntary metformin intoxication, prior to hemodialysis, a serum level of metformin over 2 mM was reported (Al-Abri et al., 2013). Tissue distribution studies have further demonstrated that the metformin concentration under steady-state is lower in plasma/serum than in other organs. It has been shown to accumulate in 7 to 10-fold higher concentrations in the gastrointestinal tract, with lesser but still significantly higher amounts in the kidney, liver, salivary glands, lung, spleen and muscle as compared to plasma levels. Under circumstances where the clearance of metformin is impaired, such as predisposing conditions affecting the cardiovascular system, liver or kidneys, toxic levels can eventually be reached. The toxic concentration of metformin seen in the present study (1 mM) is thus comparable to what is found in the blood of metformin-intoxicated patients. Although metformin is toxic to blood cells, as shown in this study, it is unlikely that platelets and PBMCs are major contributors to the development of LA. As metformin is accumulated in other organs and additionally these organs are more metabolically active, increased lactate production is likely to be seen first in other tissues. Our results therefore strengthen what has been suggested by others (Brunmair et al. 2004, Protti et al 2012b, Dykens et al, 2008), that systemic mitochondrial inhibition is the cause of metformin-induced LA.

Based on earlier studies and the present findings it is intriguing to speculate on the possibility that metformin's anti-diabetic effect may be related to inhibition of aerobic respiration. The decreased glucose levels in the liver and decreased uptake of glucose to the blood in the small intestine in metformin-treated diabetic patients might be due to partial complex I inhibition. Complex I inhibition causes reduced production of ATP, increased amounts of AMP, activation of the enzyme AMP-activated protein kinase (AMPK), and accelerated glucose turnover by increased glycolysis, trying to compensate for the reduced ATP production.

Until now, treatment measures for metformin-associated LA consist of haemodialysis and haemofiltration to remove the toxin, correct for the acidosis and increase renal blood flow.

Example 20

Intervention on Metformin-Induced Increase in Lactate Production with Cell-Permeable Succinate Prodrugs Intervention of metformin-induced increase in lactate production in intact human platelets with newly developed and synthesized cell-permeable succinate prodrugs was done in PBS containing 10 mM glucose. The platelets were exposed to either rotenone alone (2 µM), rotenone (2 µM) and antimycin (1 µg/mL, only for cells treated with NV 189), or 10 mM metformin and after 60 min either vehicle (DMSO, control), either of the cell-permeable succinate prodrugs (NV118, NV189 and NV241), or succinate were added at a concentration of 250 µM each 30 minutes. Lactate levels were measured in intervals of 30 min with the onset of the experiment. Additionally, pH was measured prior to the first addition of vehicle (dmso, control), the different cell-permeable succinate prodrugs (NV118, NV189, NV241) or succinate and at the end of the experiment. The rate of lactate production was calculated with a nonlinear fit with a 95% Confidence interval (CI) of the lactate-time curve slope (FIGS. 9, 10, 11 and 12).

Results relating to Example 20 are based on the assays described herein.

Lactate Production Due to Rotenone and Metformin Incubation in Thrombocytes is Attenuated by the Addition of Cell-Permeable Succinate Prodrugs The rate of lactate production in thrombocytes incubated with 2 µM Rotenone was 0.86 mmol lactate $(200 \cdot 10^6 \text{ trc} \cdot \text{h})^{-1}$ (95% Confidence Intervall [CI] 0.76-0.96) which was attenuated by NV118 (0.25 mmol [95% CI 0.18-0.33]), NV189 (0.42 mmol [95% CI 0.34-0.51]) and NV241 (0.34 mmol [95% CI 0.17-0.52]), which was not significantly different from cells not receiving rotenone (0.35 mmol [95% CI 0.14-0.55]) (FIGS. 9, 10 and 11). Cells incubated with antimycin in addition to rotenone and NV189 had a lactate production comparable to rotenone-treated cell (0.89 mmol [0.81-0.97]), demonstrating the specific mitochondrial effect of the cell-permeable succinate prodrugs (FIG. 10).

Cells incubated with 10 mM Metformin produce lactate at a rate of 0.86 mmol lactate $(200 \cdot 10^9 \text{ trc} \cdot \text{h})^{-1}$ (95% CI 0.69-1.04) compared 0.22 mmol (95% CI 0.14-0.30) in vehicle (water) treated cells (FIG. 12). Co-incubating with either of the three succinate prodrugs attenuate the metformin effect resulting in 0.43 mmol production (95% CI 0.33-0.54) for NV118 (FIG. 9), 0.55 mmol (95% CI 0.44-0.65) for NV189 (FIG. 10), and 0.43 mmol (95% CI 0.31-0-54) for NV241 (FIG. 11).

All references referred to in this application, including patent and patent applications, are incorporated herein by reference to the fullest extent possible.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims:

All references referred to in this application, including patent and patent applications, are incorporated herein by reference to the fullest extent possible.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps. The word "comprise" includes "contain" and "consist of".

General Description of the Class of Compounds to which the Compounds According to the Invention Belong and Specific Embodiments The class of compounds may be defined by formula (IB) below,

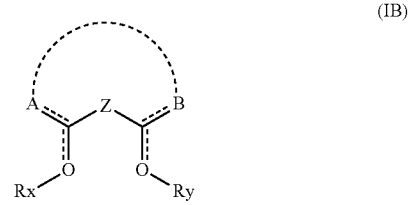

or a pharmaceutically acceptable salt thereof. Where the dotted bond between A and B denotes an optional bond so as to form a ring closed structure, wherein Z is selected from —CH$_2$—CH$_2$— or >CH(CH$_3$), —O, S, A and B are independently different or identical and are selected from —O—R', —NHR", —SR''' or —OH, with the proviso that both A and B cannot be H, R', R" and R''' are independently different or identical and selected from the formula (IIB) to (IXB) below:

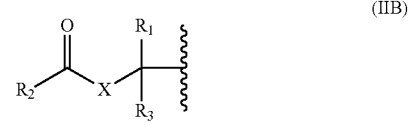

(IIB)

(IIIB)

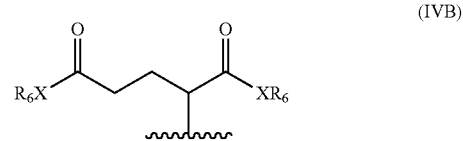

(IVB)

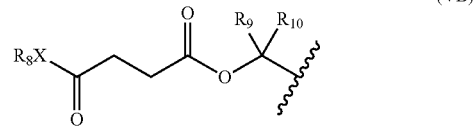

(VB)

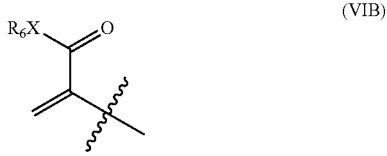

(VIB)

-continued (VIIB)

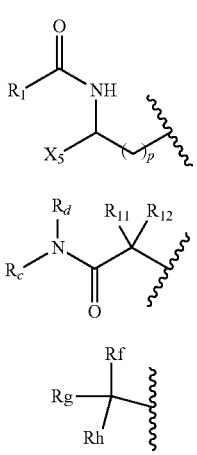

(VIIIB)

Rd  R11  R12
\\N—C—
Rc      ||
        O (IXB)

Rf
|
Rg—C—
|
Rh

R₁=H, Me, Et, propyl, i-propyl, butyl, iso-butyl, t-butyl, O-acyl, O-alkyl, N-acyl, N-alkyl, Xacyl, CH₂Xalkyl, CH₂X-acyl, F, CH₂COOH, CH₂CO₂alkyl or any of the below formulas (a)-(f)

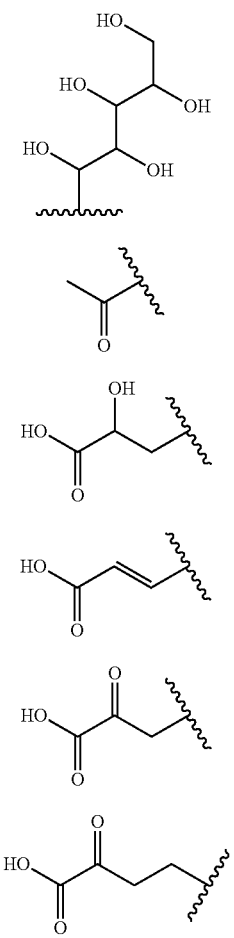

(a)

(b)

(c)

(d)

(e)

(f)

In preferred structures, R₁=H, Me, Et, propyl, i-propyl, butyl, iso-butyl, t-butyl, O-acyl, O-alkyl, N-acyl, N-alkyl, Xacyl, CH₂Xalkyl, CH₂X-acyl, F, CH₂COOH.

X=O, NH, NR₆, S

R₂=Me, Et, propyl, i-propyl, butyl, iso-butyl, t-butyl, —C(O)CH₃, —C(O)CH₂C(O)CH₃, —C(O)CH₂CH(OH)CH₃, R₃=R₁, i.e. is the same or different groups as mentioned under R₁

X₁=CR'₃R'₃, NR₄ n=1-4, p=1-2

X₂=OR₅, NR₁R'₂

R'₃=H, Me, Et, F

R₄=H, Me, Et, i-Pr

R₅=acetyl, propionyl, benzoyl, benzylcarbonyl

R'₂=H.HX₃, acyl, acetyl, propionyl, benzoyl, benzylcarbonyl

X₃=F, Cl, Br and I

R₆=H, or alkyl such as e.g. Me, Et, n-propyl, i-propyl, butyl, iso-butyl, t-butyl, or acetyl, such as e.g. acyl, propionyl, benzoyl, or formula (IIB), formula (IIBI) or formula (VIIIB)

X₅=—H, —COOH, —C(=O)XR₆,

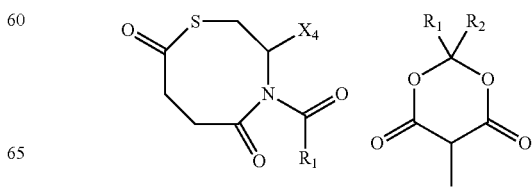

X₅ may also be CONR₁R₃.

R₉=H, Me, Et or O₂CCH₂CH₂COXR₈

R₁₀=Oacyl, NHalkyl, NHacyl, or O₂CCH₂CH₂COX₆R₈

X₆=O, NR₈

R₈=H, alkyl, Me, Et, propyl, i-propyl, butyl, iso-butyl, t-butyl, acetyl, acyl, propionyl, benzoyl or formula (IIB), R₁₁ and R₁₂ are independently H, alkyl, Me, Et, propyl, i-propyl, butyl, iso-butyl, t-butyl, acetyl, acyl, propionyl, benzoyl, acyl, —CH₂Xalkyl, —CH₂Xacyl, where X=O, NR₆ or S, R_c and R_d are independently CH₂Xalkyl, CH₂Xacyl, where X=O, NR₆ or S, Rf, Rg and Rh are independently selected from Xacyl, —CH₂Xalkyl, —CH₂X-acyl and R₉, wherein alkyl is e.g. methyl, ethyl, propyl, isopropyl, n-butyl, isobutyl, sec-butyl, tert-butyl, n-pentyl, neopentyl, isopentyl, hexyl, isohexyl, heptyl, octyl, nonyl or decyl and acyl is e.g. formyl, acetyl, propionyl, butyryl pentanoyl, benzoyl and the like, and wherein the acyls and alkyls may be optionally substituted, the dotted bond between A and B denotes an optional bond to form a cyclic structure of formula (I) and with the proviso that when such a cyclic bond is present, the compound according to formula (I) is selected from wherein $X_4$ is selected from —COOH, —C(=O)$XR_6$, and wherein $R_x$ and $R_y$ are independently selected from $R_1$, $R_2$, $R_6$ or R', R" or R''' with the proviso that $R_x$ and $R_y$ cannot both be —H.

In preferred aspect, R', R" and R''' are independently different or identical and selected from the formula (IIB), (VB), (VIIB) or VIIIB) below:

Preferably, and with respect to formula (IIB), at least one of $R_1$ and $R_3$ is —H, such that formula II is:

Preferably, and with respect to formula (VII), p is 1 or 2, preferably p is 1 and $X_5$ is —H such that formula (VIIB) is Preferably, and with respect to formula (IXB), at least one of $R_f$, $R_g$, $R_h$ is —H or alkyl, with alkyl as defined herein. Moreover, it is also preferable with respect to Formula (IXB) that at least one of Rf, Rg, Rh is —CH$_2$Xacyl, with acyl as defined herein.

An interesting subclass of the class mentioned above relates to the compounds of Formula (I)

or a pharmaceutically acceptable salt thereof. The dotted bond between A and B denotes an optional bond so as to form a ring closed structure.

In formula (IC) Z is selected from —CH$_2$—CH$_2$— or >CH(CH$_3$),

A is selected from —SR, —OR and NHR, and wherein R is

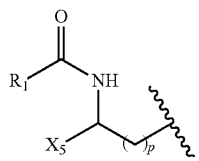

B is selected from —O—R', —NHR", —SR'" or —OH; R' is selected from the formula (IIC) to (IXC) below:

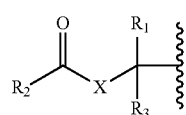
(IIC)

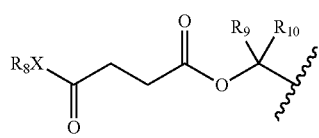
(VC)

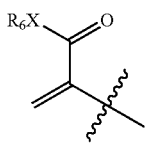
(VIC)

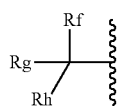
(IXC)

Preferably, R' is selected from the formula (IIC), (VC), to (IXC) below:

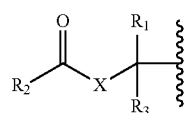
(IIC)

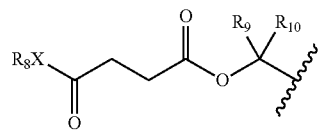
(VC)

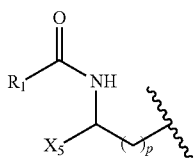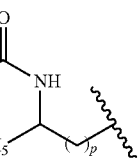
(VIIC)

R', R" and R'" are independently different or identical and is selected from formula (IVC-VIIIC) below:

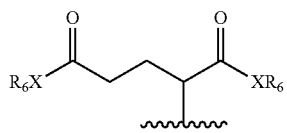
(IVC)

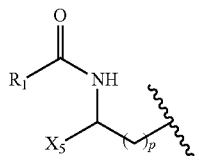
(VIIC)

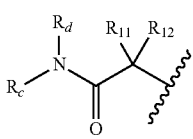
(VIIIC)

R$_1$=H, Me, Et, propyl, i-propyl, butyl, iso-butyl, t-butyl, O-acyl, O-alkyl, N-acyl, N-alkyl, Xacyl, CH$_2$Xalkyl, CH$_2$X-acyl, F, CH$_2$COOH, CH$_2$CO$_2$alkyl or any of formulae (a)-(f)

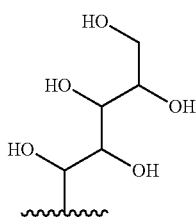
a)

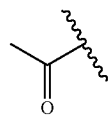
(b)

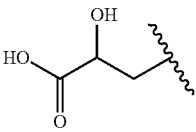
(c)

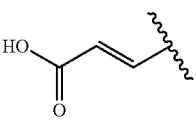
(d)

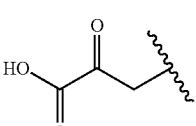
(e)

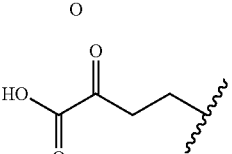
(f)

Preferably, R$_1$=H, Me, Et, propyl, i-propyl, butyl, iso-butyl, t-butyl, O-acyl, O-alkyl, N-acyl, N-alkyl, Xacyl, CH$_2$Xalkyl, CH$_2$X-acyl, F, CH$_2$COOH, CH$_2$CO$_2$alkyl,

X=O, NH, NR$_6$, S $R_2$=Me, Et, propyl, i-propyl, butyl, iso-butyl, t-butyl, $C(O)CH_3$, $C(O)CH_2C(O)CH_3$, $C(O)CH_2CH(OH)CH_3$, $R_3$=$R_1$, i.e. may be the same or a different group as defined under $R_1$, $X_1$=$CR'_3R'_3$, $NR_4$ n=1-4, p=1-2

$X_2$=$OR_5$, $NR_1R'_2$ $R'_3$=H, Me, Et, F $R_4$=H, Me, Et, i-Pr $R_5$=acetyl, propionyl, benzoyl, benzylcarbonyl $R'_2$=H.$HX_3$, acyl, acetyl, propionyl, benzoyl, benzylcarbonyl $X_3$=F, Cl, Br and I $R_6$=H, alkyl, Me, Et, propyl, i-propyl, butyl, iso-butyl, t-butyl, acetyl, acyl, propionyl, benzoyl, or formula (IIC), formula (IIIC) or formula (VIIIC)

$X_5$=—H, —COH, —C(=O)$XR_6$,

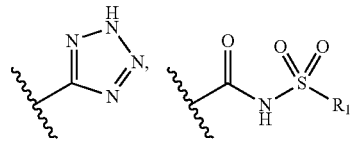

$X_5$ may also be $CONR_1R_3$ $R_9$=H, Me, Et or $O_2CCH_2CH_2COXR_8$ $R_{10}$=Oacyl, NHalkyl, NHacyl, or $O_2CCH_2CH_2COX_6R_8$ $X_6$=O, $NR_8$ $R_8$=H, alkyl, Me, Et, propyl, i-propyl, butyl, iso-butyl, t-butyl, acetyl, acyl, propionyl, benzoyl, or formula (IIC), formula (IIIC) or formula (VIIIC)

$R_{11}$ and $R_{12}$ are independently H, alkyl, Me, Et, propyl, i-propyl, butyl, iso-butyl, t-butyl, acetyl, acyl, propionyl, benzoyl, acyl, —$CH_2$Xalkyl, —$CH_2$Xacyl, where X=O, $NR_6$ or S $R_c$ and $R_d$ are independently $CH_2$Xalkyl, $CH_2$Xacyl, where X=O, $NR_6$ or S, $R_f$, $R_g$ and $R_h$ are independently selected from Xacyl, —$CH_2$Xalkyl, —$CH_2$X-acyl and $R_9$ alkyl is e.g. Me, Et, propyl, i-propyl, butyl, iso-butyl, t-butyl and acyl is e.g. formyl, acetyl, propionyl, isopropionyl, byturyl, tert-butyryl, pentanoyl, benzoyl and the likes and wherein the acyls and alkyls may be optionally substituted, and when the dotted bond between A and B is present, the compound according to formula (I) is

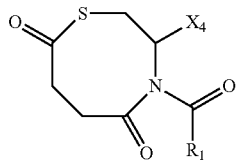

wherein $X_4$ is selected from —COOH, —C(=O)$XR_6$,

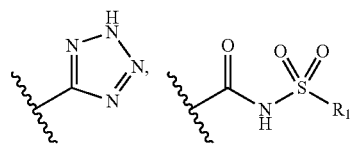

Preferably, and with respect to formula (IIC), at least one of $R_1$ and $R_3$ is —H, such that formula II is:

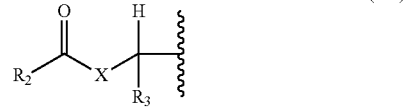

(IIC)

Preferably, and with respect to formula (VIIC), p is 1 or 2, preferably p is 1 and $X_5$ is —H such that formula (VIIC) is

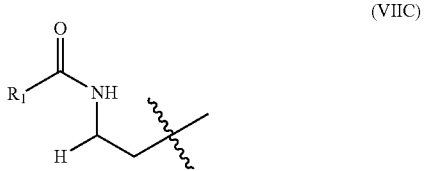

(VIIC)

Preferably, and with respect to formula (IXC), at least one of $R_f$, $R_g$, $R_h$ is —H or alkyl, with alkyl as defined herein. Moreover, it is also preferable with respect to Formula (IXC) that at least one of $R_f$, $R_g$, $R_h$ is —$CH_2$Xacyl, with acyl as defined herein.

Interesting compounds according to formula (IC) are:

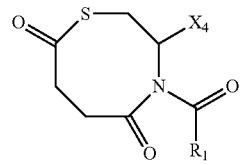

wherein $X_4$ is selected from —COOH, —C(=O)$XR_6$,

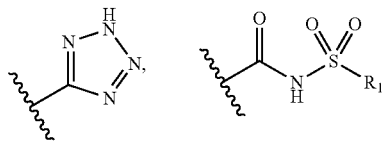

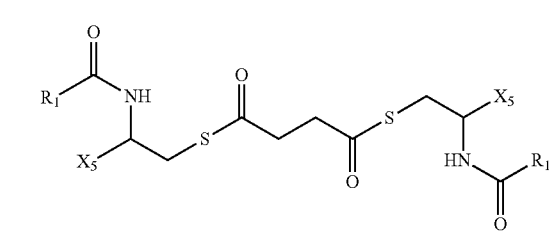

wherein $R_1$ and $X_5$ is as defined herein. Preferably $X_5$ is —H.

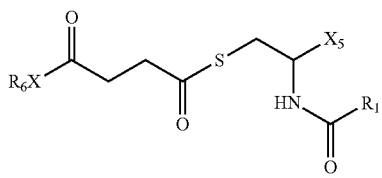

wherein $R_6$, $X_5$ and $R_1$ are as defined herein. Preferably $X_5$ is —H.

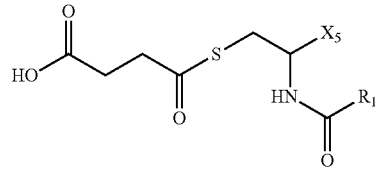

wherein $X_5$ and $R_1$ are as defined herein. Preferably $X_5$ is —H.

SPECIFIC EMBODIMENTS

1. A compound according to Formula (I)

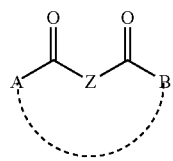
(I)

or a pharmaceutically acceptable salt thereof, wherein the dotted bond between A and B denotes an optional bond so as to form a ring closed structure, and wherein Z is selected from —CH$_2$—CH$_2$— or >CH(CH$_3$),
A is selected from —SR, —OR and NHR and R is

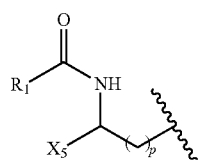

B is selected from —O—R', —NHR'', —SR''' or —OH; and R' is selected from the formula (II) to (IX) below:

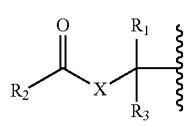
(II)

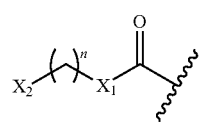
(III)

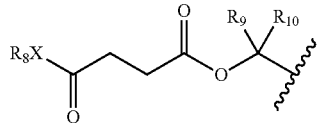
(V)

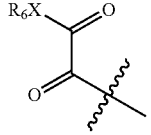
(VI)

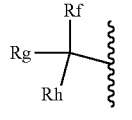
(IX)

R', R'' and R''' are independently different or identical and is selected from formula (IV-VIII) below:

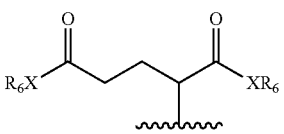
(IV)

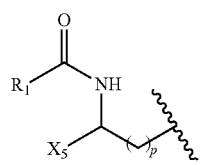
(VII)

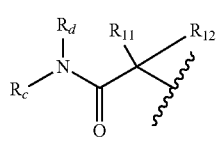
(VIII)

$R_1$=H, Me, Et, propyl, i-propyl, butyl, iso-butyl, t-butyl, O-acyl, O-alkyl, N-acyl, N-alkyl, Xacyl, CH$_2$Xalkyl, CH$_2$X-acyl, F, CH$_2$COOH, CH$_2$CO$_2$alkyl or any of the below formulae (a)-(f)

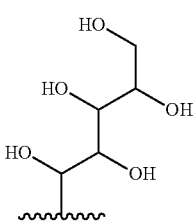
(a)

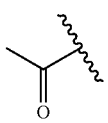
(b)

(c)
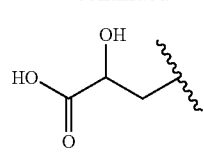

(d)
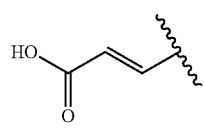

(e)
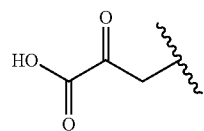

(f)
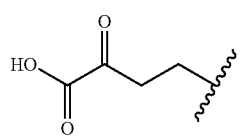

X=O, NH, NR$_6$, S

R$_2$=Me, Et, propyl, i-propyl, butyl, iso-butyl, t-butyl, C(O)CH$_3$, C(O)CH$_2$C(O)CH$_3$, C(O)CH$_2$CH(OH)CH$_3$, R$_3$=R$_1$, i.e. different or identical with the groups mentioned under R$_1$,

X$_1$=CR'$_3$R'$_3$, NR$_4$ n=1-4, p=1-2

X$_2$=OR$_5$, NR$_1$R'$_2$

R'$_3$=H, Me, Et, F

R$_4$=H, Me, Et, i-Pr

R$_5$=acetyl, propionyl, benzoyl, benzylcarbonyl

R'$_2$=H.HX$_3$, acyl, acetyl, propionyl, benzoyl, benzylcarbonyl

X$_3$=F, Cl, Br and I

R$_6$=H, alkyl, Me, Et, propyl, i-propyl, butyl, iso-butyl, t-butyl, acetyl, acyl, propionyl, benzoyl, or formula (II), formula (III) or formula (VIII)

X$_5$=—H, —COOH, —C(=O)XR$_6$,

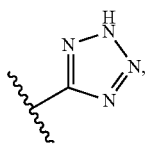 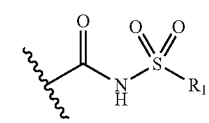

R$_9$=H, Me, Et or O$_2$CCH$_2$CH$_2$COXR$_8$

R$_{10}$=Oacyl, NHalkyl, NHacyl, or O$_2$CCH$_2$CH$_2$CO X$_6$R$_8$

X$_6$=O, NR$_8$

R$_8$=H, alkyl, Me, Et, propyl, i-propyl, butyl, iso-butyl, t-butyl, acetyl, acyl, propionyl, benzoyl, or formula (II), formula (III) or formula (VIII)

R$_{11}$ and R$_{12}$ are independently H, alkyl, Me, Et, propyl, i-propyl, butyl, iso-butyl, t-butyl, acetyl, acyl, propionyl, benzoyl, acyl, —CH$_2$Xalkyl, —CH$_2$Xacyl, where X=O, NR$_6$ or S R$_c$ and R$_d$ are independently CH$_2$Xalkyl, CH$_2$Xacyl, where X=O, NR$_6$ or S, R$_f$, R$_g$ and R$_h$ are independently selected from Xacyl, —CH$_2$Xalkyl, —CH$_2$X-acyl and R$_9$ alkyl is e.g. Me, Et, propyl, i-propyl, butyl, iso-butyl, t-butyl and acyl is e.g. formyl, acetyl, propionyl, isopropionyl, byturyl, tert-butyryl, pentanoyl, benzoyl and the likes and wherein the acyls or alkyls may be optionally substituted, and when the dotted bond between A and B is present, the compound according to formula (I) is

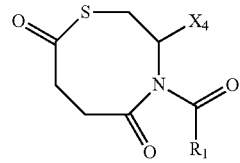

wherein X$_4$ is selected from —COOH, —C(=O)XR$_6$,

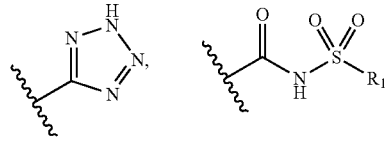

and with the further proviso that the compound is not any of the below compounds

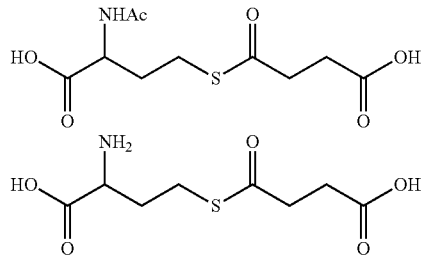

2. A compound according to embodiment 1, wherein formula (II) is such that at least one of R1 and R$_3$ is —H such that formula II is:

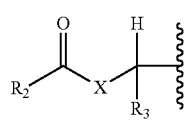

(II)

3. A compound according to embodiment 1, wherein formula (III) is such that R$_4$ is —H and formula (III) is

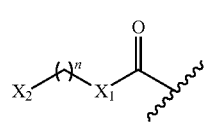

(III)

and X$_1$ is NH

4. A compound according to embodiment 1, wherein formula (VII) is such that, p=2 and X$_5$ is —H and formula (VII) is (VII)

5. A compound according to embodiment 1, wherein formula (IX) is such that at least one of $R_f$, $R_g$, $R_h$ is —H or alkyl, with alkyl as defined herein.

6. A compound according to embodiment 1 or 5, wherein formula (IX) is such that at least one of Rf, Rg, Rh is —CH$_2$Xacyl, with acyl as defined herein.

7. A compound according to any of embodiments 1-6, wherein Formula (I) is (I)

wherein $X_4$ is selected from —COOH, —C(=O)$XR_6$,

8. A compound according to any of embodiments 1-6, wherein Formula (I) is (I)

Wherein $X_5$ and $R_1$ is as defined in claim 1 and wherein $X_5$ is preferably —H 9. A compound according to any of embodiments 1-6, wherein Formula (I) is wherein $X_5$ and $R_1$ is as defined in embodiment 1 and wherein $X_5$ is preferably —H 10. A compound according to any of embodiments 1-6, wherein Formula (I) is (I)

Wherein $X_5$, $R_1$ and $R_6$ is as defined in embodiment 1 and wherein $X_5$ is preferably —H.

11. A compound according to any of embodiments 1-10 for use in medicine

12. A compound according to any of embodiments 1-10, for use in cosmetics

13. A compound according to any of embodiments 1-10 for use in the treatment of or prevention of metabolic diseases, or in the treatment of diseases of mitochondrial dysfunction or disease related to mitochondrial dysfunction, treating or suppressing of mitochondrial disorders, stimulation of mitochondrial energy production, treatment of cancer and following hypoxia, ischemia, stroke, myocardial infarction, acute angina, an acute kidney injury, coronary occlusion and atrial fibrillation, or to avoid or counteract reperfusion injuries.

14. A compound according for use according to embodiment 11, wherein the medical use is prevention or treatment of drug-induced mitochondrial side-effects.

15. A compound for use according to embodiment 14, wherein the prevention or drug-induced mitochondrial side-effects relates to drug interaction with Complex I, such as e.g. metformin-Complex I interaction.

16. A compound according to embodiment 13, wherein diseases of mitochondrial dysfunction involves e.g. mitochondrial deficiency such as a Complex I, II, III or IV deficiency or an enzyme deficiency like e.g. pyruvate dehydrogenase deficiency.

17. A compound for use according to any of embodiments 13-16, wherein the diseases of mitochondrial dysfunction or disease related to mitochondrial dysfunction are selected from Alpers Disease (Progressive Infantile Poliodystrophy, Amyotrophic lateral sclerosis (ALS), Autism, Barth syndrome (Lethal Infantile Cardiomyopathy), Beta-oxidation Defects, Bioenergetic metabolism deficiency, Carnitine-Acyl-Carnitine Deficiency, Carnitine Deficiency, Creatine Deficiency Syndromes (Cerebral Creatine Deficiency Syndromes (CCDS) includes: Guanidinoaceteate Methyltransferase Deficiency (GAMT Deficiency), L-Arginine:Glycine Amidinotransferase Deficiency (AGAT Deficiency), and SLC6A8-Related Creatine Transporter Deficiency (SLC6A8

Deficiency), Co-Enzyme Q10 Deficiency, Complex I Deficiency (NADH dehydrogenase (NADH-CoQ reductase deficiency), Complex II Deficiency (Succinate dehydrogenase deficiency), Complex III Deficiency (Ubiquinone-cytochrome c oxidoreductase deficiency), Complex IV Deficiency/COX Deficiency (Cytochrome c oxidase deficiency is caused by a defect in Complex IV of the respiratory chain), Complex V Deficiency (ATP synthase deficiency), COX Deficiency, CPEO (Chronic Progressive External Ophthalmoplegia Syndrome), CPT I Deficiency, CPT II Deficiency, Friedreich's ataxia (FRDA or FA), Glutaric Aciduria Type II, KSS (Kearns-Sayre Syndrome), Lactic Acidosis, LCAD (Long-Chain Acyl-CoA Dehydrogenase Deficiency), LCHAD, Leigh Disease or Syndrome (Subacute Necrotizing Encephalomyelopathy), LHON (Leber's hereditary optic neuropathy), Luft Disease, MCAD (Medium-Chain Acyl-CoA Dehydrogenase Deficiency), MELAS (Mitochondrial Encephalomyopathy Lactic Acidosis and Stroke-like Episodes), MERRF (Myoclonic Epilepsy and Ragged-Red Fiber Disease), MIRAS (Mitochondrial Recessive Ataxia Syndrome), Mitochondrial Cytopathy, Mitochondrial DNA Depletion, Mitochondrial Encephalopathy including: Encephalomyopathy and Encephalomyelopathy, Mitochondrial Myopathy, MNGIE (Myoneurogastointestinal Disorder and Encephalopathy, NARP (Neuropathy, Ataxia, and Retinitis Pigmentosa), Neurodegenerative disorders associated with Parkinson's, Alzheimer's or Huntington's disease, Pearson Syndrome, Pyruvate Carboxylase Deficiency, Pyruvate Dehydrogenase Deficiency, POLG Mutations, Respiratory Chain Deficiencies, SCAD (Short-Chain Acyl-CoA Dehydrogenase Deficiency), SCHAD, VLCAD (Very Long-Chain Acyl-CoA Dehydrogenase Deficiency).

18. A compound for use according to embodiment 17, wherein the mitochondrial dysfunction or disease related to mitochondrial dysfunction is attributed to complex I dysfunction and selected from Leigh Syndrome, Leber's hereditary optic neuropathy (LHON), MELAS (mitochondrial encephalomyopathy, lactic acidosis, and stroke-like episodes) and MERRF (myoclonic epilepsy with ragged red fibers).

19. A composition comprising a compound of Formula (I) as defined according any of embodiments 1-10 and one or more pharmaceutically or cosmetically acceptable excipients.

20. A method of treating a subject suffering from diseases of mitochondrial dysfunction or disease related to mitochondrial dysfunction as defined in any of embodiments 16-18, the method comprising administering to the subject an efficient amount of a composition as defined in embodiment 19.

21. A method according to embodiment 20, wherein the composition is administered parenterally, orally, topically (including buccal, sublingual or transdermal), via a medical device (e.g. a stent), by inhalation or via injection (subcutaneous or intramuscular)

22. A method according to any of embodiments 20-21, wherein the composition is administered as a single dose or a plurality of doses over a period of time, such as e.g. one daily, twice daily or 3-5 times daily as needed.

23. A compound according to any of embodiments 1-10 for use in the treatment or prevention of lactic acidosis.

24. A compound according to any of embodiments 1-10 for use in the treatment or prevention of a drug-induced side-effect selected from lactic acidosis and side-effects related to Complex I defect, inhibition or malfunction.

25. A compound according to any of embodiments 1-10 for use in the treatment or prevention of a drug-induced side-effect selected from lactic acidosis and side-effects related to defect, inhibition or mal-function in aerobic metabolism upstream of complex I (indirect inhibition of Complex I, which would encompass any drug effect that limits the supply of NADH to Complex I, e.g. effects on Krebs cycle, glycolysis, beta-oxidation, pyruvate metabolism and drugs that affect the levels of glucose or other Complex I-related substrates).

26. A combination of a drug substance and a compound according to any of embodiments 1-10 for use in the treatment and/or prevention of a drug-induced side-effect selected from i) lactic acidosis, ii) and side-effects related to a Complex I defect, inhibition or malfunction, and iii) side-effects related to defect, inhibition or malfunction in aerobic metabolism upstream of complex I (indirect inhibition of Complex I, which would encompass any drug effect that limits the supply of NADH to Complex I, e.g. effects on Krebs cycle, glycolysis, beta-oxidation, pyruvate metabolism and drugs that affect the levels of glucose or other Complex-I-related substrates), wherein
i) the drug substance is used for treatment of a disease for which the drug substance is indicated, and
ii) the succinate prodrug is used for prevention or alleviation of the side effects induced or inducible by the drug substance, wherein the side-effects are selected from lactic acidosis and side-effects related to a Complex I defect, inhibition or malfunction.

27. A composition comprising a drug substance and a compound according to any of embodiments 1-10, wherein the drug substance has a potential drug-induced side-effect selected from i) lactic acidosis, ii) side-effects related to a Complex I defect, inhibition or malfunction, and iii) side-effects related to defect, inhibition or malfunction in aerobic metabolism upstream of complex I (indirect inhibition of Complex I, which would encompass any drug effect that limits the supply of NADH to Complex I, e.g. effects on Krebs cycle, glycolysis, beta-oxidation, pyruvate metabolism and even drugs that affect the levels of glucose or other Complex-I-related substrates).

28. A kit comprising
i) a first container comprising a drug substance, which has a potential drug-induced side-effect selected i) from lactic acidosis, ii) and side-effects related to a Complex I defect, inhibition or malfunction, and iii) side-effects related to defect, inhibition or malfunction in aerobic metabolism upstream of complex I (indirect inhibition of Complex I, which would encompass any drug effect that limits the supply of NADH to Complex I, e.g. effects on Krebs cycle, glycolysis, beta-oxidation, pyruvate metabolism and even drugs that affect the levels of glucose or other substrates), and
ii) a second container comprising a compound according to any of embodiments 1-10, which has the potential for prevention or alleviation of the side effects induced or inducible by the drug substance, wherein the side-effects are selected from i) lactic acidosis, ii) side-effects related to a Complex I defect, inhibition or malfunction, and iii) side-effects related to defect, inhibition or malfunction in aerobic metabolism upstream of complex I (indirect inhibition of Complex I, which would encompass any drug effect that limits the supply of NADH to Complex I, e.g. effects on Krebs cycle, glycolysis, beta-oxidation, pyruvate metabolism and even drugs that affect the levels of glucose or other substrates).

29. A method for treating a subject suffering from a drug-induced side-effect selected from i) lactic acidosis, ii) side-effect related to a Complex I defect, inhibition or malfunction, and iii) side-effects related to defect, inhibition or malfunction in aerobic metabolism upstream of complex I (indirect inhibition of Complex I, which would encompass any drug effect that limits the supply of NADH to Complex I, e.g. effects on Krebs cycle, glycolysis, beta-oxidation, pyruvate metabolism and even drugs that affect the levels of glucose or other substrates, the method comprises administering an effective amount of a compound according to any of embodiments 1-10 to the subject.

30. A method for preventing or alleviating a drug-induced side-effect selected from i) lactic acidosis, ii) side-effect related to a Complex I defect, inhibition or malfunction, and iii) side-effects related to defect, inhibition or malfunction in aerobic metabolism upstream of complex I (indirect inhibition of Complex I, which would encompass any drug effect that limits the supply of NADH to Complex I, e.g. effects on Krebs cycle, glycolysis, beta-oxidation, pyruvate metabolism and even drugs that affect the levels of glucose or other substrates) in a subject, who is suffering from a disease that is treated with a drug substance, which potentially induce a side-effect selected from i) lactic acidosis, ii) side-effect related to a Complex I defect, inhibition or malfunction, and iii) side-effects related to defect, inhibition or malfunction in aerobic metabolism upstream of Complex I, such as in dehydrogenases of Kreb's cycle, pyruvate dehydrogenase and fatty acid metabolism, the method comprises administering an effective amount of a compound according to any of embodiments 1-10 to the subject.

31. A method according to any one of embodiments 29-30, wherein the drug substance is an anti-diabetic substance.

32. A method according to any one of embodiments 29-31, wherein the anti-diabetic substance is metformin.

33. A compound according to any of embodiments 1-10, for use in the treatment of absolute or relative cellular energy deficiency.

The invention claimed is:
1. A compound according to Formula (IA)

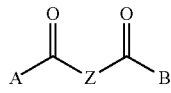
(IA)

or a pharmaceutically acceptable salt thereof, wherein
Z is —CH$_2$—CH$_2$—,
A is —SR, and R is

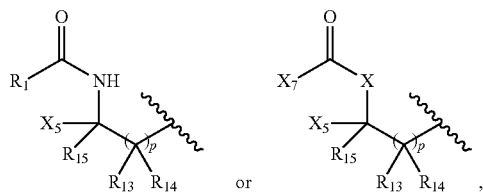

B is selected from the group consisting of —O—R', —SR''' and —OH; and R' is selected from the group consisting of:

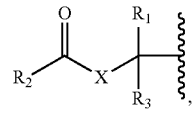
(II)

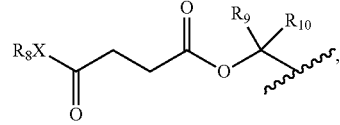
(V)

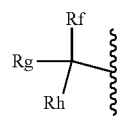
(IX)

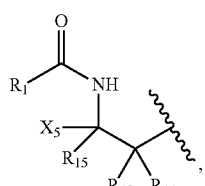
(VII)

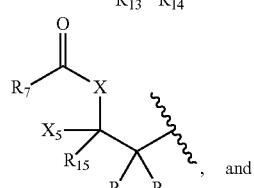
, and
(VIII)

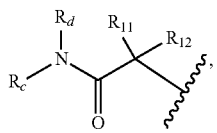

R''' is selected from the group consisting of:

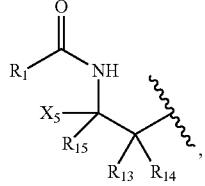
(VII)

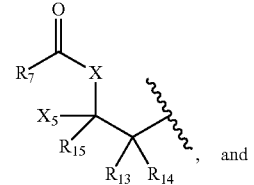
, and
(VIII)

R$_1$ and R$_3$ are independently different or identical and are selected from the group consisting of H, Me, Et, propyl, i-propyl, butyl, iso-butyl, O-acyl, O-alkyl, N-acyl, N-alkyl, Xacyl, CH$_2$Xalkyl, CH$_2$X-acyl, F, CH$_2$COOH, and CH$_2$CO$_2$alkyl, X is selected from the group consisting of O, NR$_6$, and S, R$_2$ is selected from the group consisting of Me, Et, propyl, i-propyl, butyl, iso-butyl, t-butyl, C(O)CH$_3$, C(O)CH$_2$C(O)CH$_3$, and C(O)CH$_2$CH(OH)CH$_3$, R$_6$ is selected from the group consisting of H, Me, Et, propyl, i-propyl, butyl, iso-butyl, t-butyl, acetyl, acyl, propionyl, benzoyl, formula (II), and formula (VIII), X$_5$ is selected from the group consisting of Me, Et, propyl, i-propyl, butyl, iso-butyl, t-butyl, —COOH, —C(=O)XR$_6$,

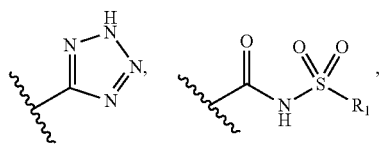

and CONR$_1$R$_3$,

X$_7$ is R$_1$ or —NR$_1$R$_3$,

R$_9$ is selected from the group consisting of H, Me, Et and O$_2$CCH$_2$CH$_2$COX$_6$R$_8$, R$_{10}$ is selected from the group consisting of Oacyl, NHalkyl, NHacyl, and O$_2$CCH$_2$CH$_2$COX$_6$R$_8$, X$_6$ is selected from the group consisting of 0, NR$_8$, and NR$_6$R$_8$, wherein R$_6$ and R$_8$ are independently different or identical and R$_8$ is selected from the group consisting of H, alkyl, Me, Et, propyl, i-propyl, butyl, iso-butyl, t-butyl, acetyl, acyl, propionyl, benzoyl, formula (II), and formula (VIII), R$_{11}$ and R$_{12}$ are independently different or identical and are selected from the group consisting of H, Me, Et, propyl, i-propyl, butyl, iso-butyl, t-butyl, acetyl, propionyl, benzoyl, —CH$_2$Xalkyl, and —CH$_2$Xacyl, R$_c$ and R$_d$ are independently different or identical and are CH$_2$Xalkyl or CH$_2$Xacyl, R$_{13}$, R$_{14}$ and R$_{15}$ are independently different or identical and are selected from the group consisting of H, Me, Et, propyl, i-propyl, butyl, iso-butyl, t-butyl, —COOH, O-acyl, O-alkyl, N-acyl, N-alkyl, Xacyl, and CH$_2$Xalkyl;

Substituents on R$_{13}$ and R$_{14}$ or R$_{13}$ and R$_{15}$ may bridge to form a cyclic system, R$_f$, R$_g$ and R$_h$ are independently different or identical and are selected from the group consisting of Xacyl, —CH$_2$Xalkyl, —CH$_2$X—acyl and R$_9$, alkyl is selected from the group consisting of Me, Et, propyl, i-propyl, butyl, and iso-butyl, acyl is selected from the group consisting of formyl, acetyl, propionyl, isopropionyl, byturyl, tert-butyryl, pentanoyl, and benzoyl, acyl and/or alkyl may be optionally substituted, with the proviso that the compound is not

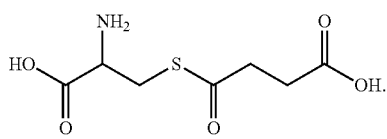 [SMILES: NC(CSC(=O)CCC(=O)O)C(=O)O]

2. A compound according to Formula (IA)

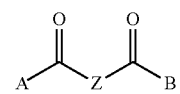

or a pharmaceutically acceptable salt thereof, wherein

Z is —CH$_2$CH$_2$—,

A is —SR, and R is

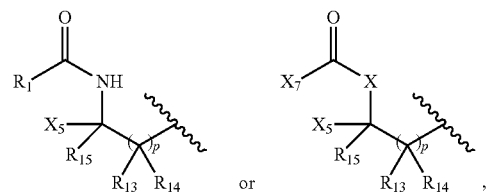

B is selected from the group consisting of —O—R', —SR''' and —OH; and

R' and R''' are independently different or identical and are:

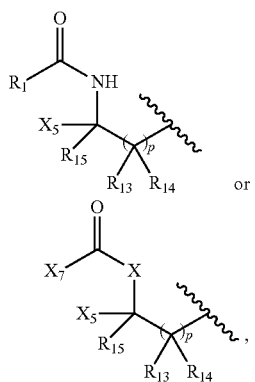

R$_1$ and R$_3$ are independently different or identical and are selected from the group consisting of H, Me, Et, propyl, O—Me, O—Et, and O-propyl, X is selected from the group consisting of O, NH, and S, R$_6$ is selected from the group consisting of H, Me, and Et, X$_5$ is selected from the group consisting of —H, Me, Et, —COOH, —C(=O)XR$_6$, and CONR$_1$R$_3$ X$_7$ is R$_1$ or —NR$_1$R$_3$, and R$_{13}$, R$_{14}$ and R$_{15}$ are independently different or identical and are selected from the group consisting of H, Me, Et, propyl, i-propyl, butyl, iso-butyl, t-butyl, —COOH, O-acyl, O-alkyl, N-acyl, N-alkyl, Xacyl, and CH$_2$Xalkyl, Substituents on R$_{13}$ and R$_{14}$ or R$_{13}$ and R$_{15}$ may bridge to form a cyclic system, alkyl is selected from the group consisting of Me, Et, propyl, i-propyl, butyl, and iso-butyl, acyl is selected from the group consisting of formyl, acetyl, propionyl, isopropionyl, byturyl, tert-butyryl, pentanoyl, and benzoyl, acyl and/or alkyl may be optionally substituted, with the proviso that the compound is not

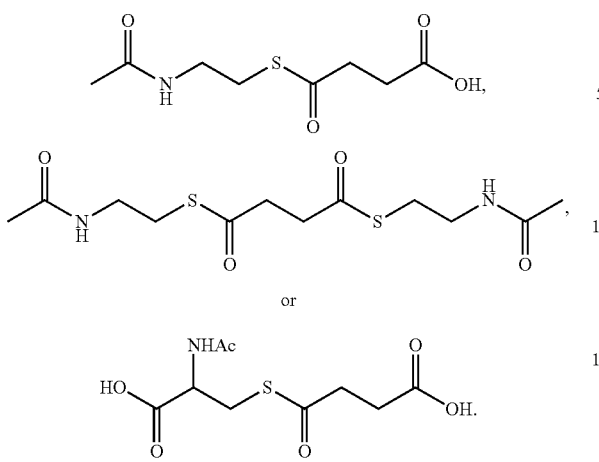

3. A compound according to Formula (IA)

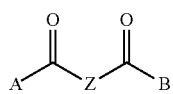

or a pharmaceutically acceptable salt thereof, wherein
Z is —CH$_2$—CH$_2$—,
A is —SR, and R is

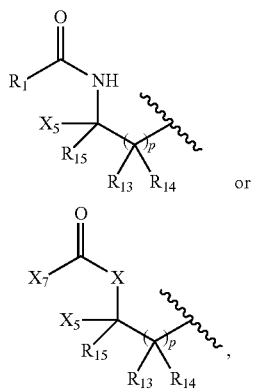

B is selected from the group consisting of —O—R', —SR''' and —OH; and
R' and R''' are independently different or identical and are selected from:

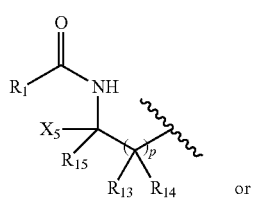

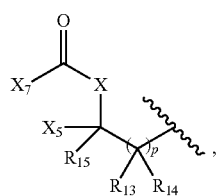

R$_1$ and R$_3$ are independently different or identical and are selected from the group consisting of H, Me, Et, propyl, O-Me, O-Et, and O-propyl, X is selected from the group consisting of O, NH, and S, R$_6$ is selected from the group consisting of H, Me, and Et, X$_5$ is selected from the group consisting of —H, Me, Et, —COOH, —C(=O)OR$_6$, and CONR$_1$R$_3$, X$_7$ is R$_1$ or —NR$_1$R$_3$, and R$_{13}$, R$_{14}$ and R$_{15}$ are independently different or identical and are selected from the group consisting of H, Me, Et, and —COOH, Substituents on R$_{13}$ and R$_{14}$ or R$_{13}$ and R$_{15}$ may bridge to form a cyclic system, with the proviso that the compound is not

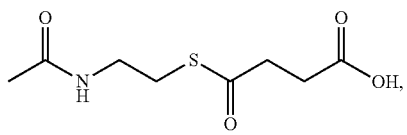

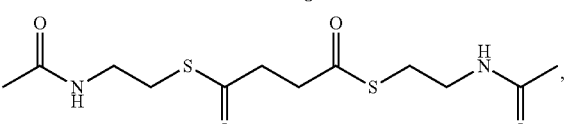

or

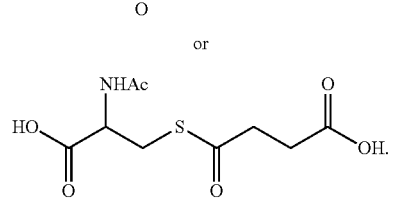

4. The compound according to claim 1, wherein B is OH or SR'''.

5. The compound according to claim 1, wherein B is OH or SR''' and, where R''' is

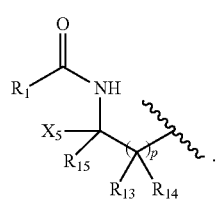

6. The compound according to claim 1, wherein B is OH.

7. The compound according to claim 1, wherein B is OH and R is

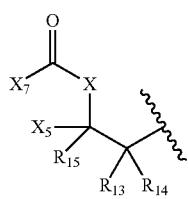
and X is S.
8. The compound according to claim 1, wherein R and/or R''' is
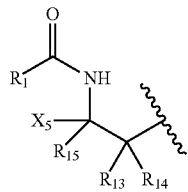
9. The compound according to claim 1, wherein R and/or R''' is
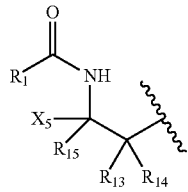
and $X_5$ is C(=O)$XR_6$ such that formula (VII) is
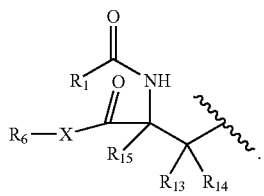
10. The compound according to claim 1, wherein R and/or R''' is
(VII)
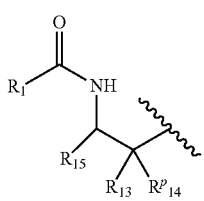
and $X_5$ is $CONR_1R_3$ such that formula (VII) is
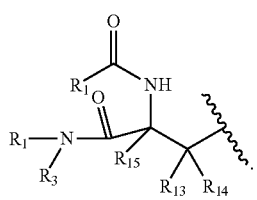
11. A compound, wherein the compound is selected from the group consisting of:
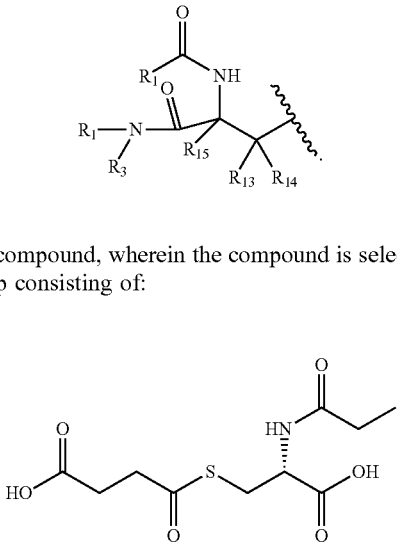
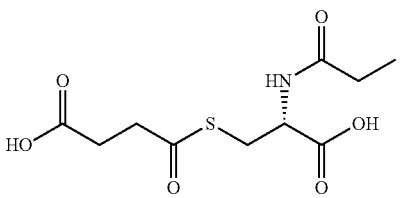
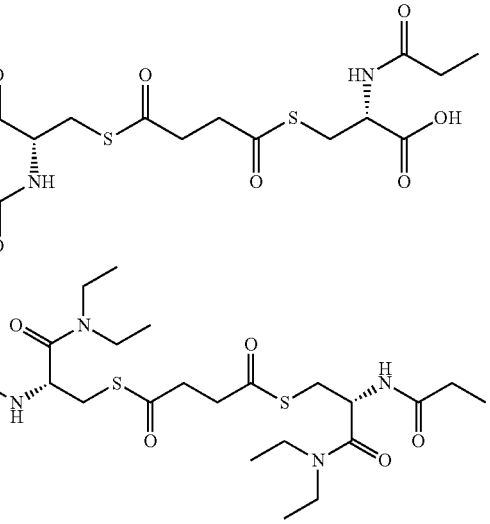
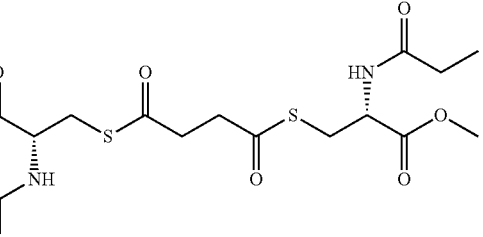
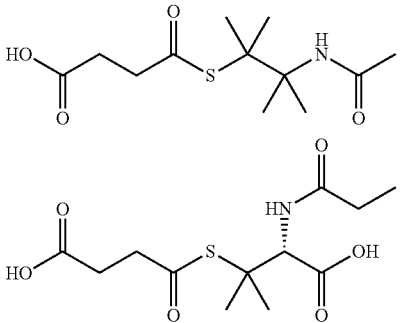

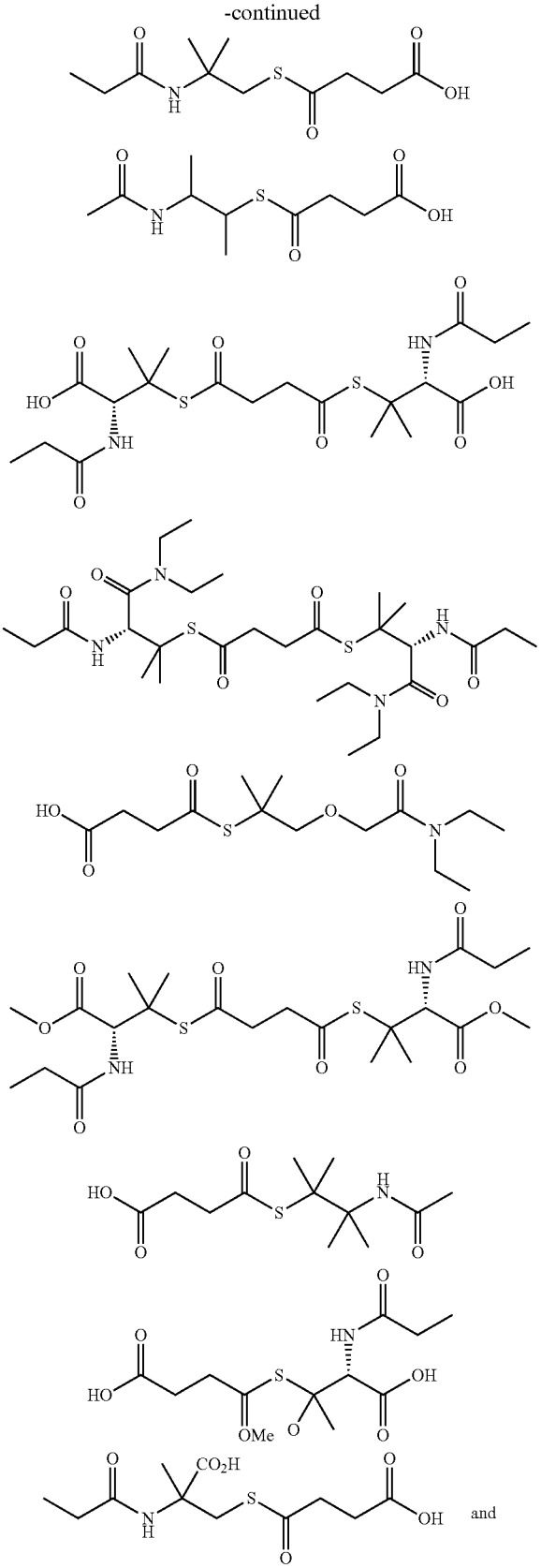

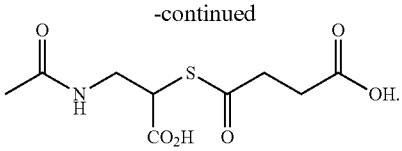

12. A composition comprising a compound according to claim 1 and one or more pharmaceutically or cosmetically acceptable excipients.

13. A combination of a drug substance and a compound according to claim 1.

14. A composition comprising a drug substance and a compound according to claim 1, wherein the drug substance has a potential drug-induced side-effect selected from i) lactic acidosis, ii) side-effects related to a Complex I defect, inhibition or malfunction, and iii) side-effects related to defect, inhibition or malfunction in aerobic metabolism upstream of complex I.

15. A kit comprising
   i) a first container comprising a drug substance, which has a potential drug-induced side-effect selected i) from lactic acidosis, ii) side-effects related to a Complex I defect, inhibition or malfunction, and iii) side-effects related to defect, inhibition or malfunction in aerobic metabolism upstream of complex I, and
   ii) a second container comprising a compound according to claim 1.

16. A combination of a drug substance and a compound according to claim 2.

17. A composition comprising a drug substance and a compound according to claim 2, wherein the drug substance has a potential drug-induced side-effect selected from i) lactic acidosis, ii) side-effects related to a Complex I defect, inhibition or malfunction, and iii) side-effects related to defect, inhibition or malfunction in aerobic metabolism upstream of complex I.

18. A kit comprising
   i) a first container comprising a drug substance, which has a potential drug-induced side-effect selected i) from lactic acidosis, ii) side-effects related to a Complex I defect, inhibition or malfunction, and iii) side-effects related to defect, inhibition or malfunction in aerobic metabolism upstream of complex I, and
   ii) a second container comprising a compound according to claim 2.

19. A combination of a drug substance and a compound according to claim 3.

20. A composition comprising a drug substance and a compound according to claim 3, wherein the drug substance has a potential drug-induced side-effect selected from i) lactic acidosis, ii) side-effects related to a Complex I defect, inhibition or malfunction, and iii) side-effects related to defect, inhibition or malfunction in aerobic metabolism upstream of complex I.

21. A kit comprising
   i) a first container comprising a drug substance, which has a potential drug-induced side-effect selected i) from lactic acidosis, ii) side-effects related to a Complex I defect, inhibition or malfunction, and iii) side-effects related to defect, inhibition or malfunction in aerobic metabolism upstream of complex I, and
   ii) a second container comprising a compound according to claim 3.

\* \* \* \* \*

UNITED STATES PATENT AND TRADEMARK OFFICE
CERTIFICATE OF CORRECTION

PATENT NO. : 11,147,789 B2
APPLICATION NO. : 15/128480
DATED : October 19, 2021
INVENTOR(S) : Eskil Elmer et al.

It is certified that error appears in the above-identified patent and that said Letters Patent is hereby corrected as shown below:

In the Claims

At Column 83, Line 60:
Please delete "( )p" from both formulas.

At Column 84, Line 28:
Please delete "R7" from the formula and insert therefor --X7--.

At Column 84, Line 53:
Please delete "R7" from the formula and insert therefor --X7--.

At Column 85, Line 30:
Please delete "0" and insert therefor --O--.

At Column 85, Line 61:
Please delete "NH2" from the formula and insert therefor --NHAc--.

At Column 86, Line 20:
Please delete "( )p" from both formulas.

At Column 86, Line 34:
Please delete "( )p" from the formula.

At Column 86, Line 41:
Please delete "( )p" from the formula.

At Column 87, Line 40:
Please delete "( )p" from the formula.

Signed and Sealed this
Eighteenth Day of January, 2022

Drew Hirshfeld
*Performing the Functions and Duties of the*
*Under Secretary of Commerce for Intellectual Property and*
*Director of the United States Patent and Trademark Office*

At Column 87, Line 49:
Please delete "( )p" from the formula.

At Column 87, Line 65:
Please delete "( )p" from the formula.

At Column 88, Line 8:
Please delete "( )p" from the formula.

At Column 88, Line 60:
Please delete "( )p" from the formula.

At Column 89, Line 65:
Please delete "p" from the formula.